United States Patent
Ogawa et al.

(10) Patent No.: US 11,536,656 B2
(45) Date of Patent: Dec. 27, 2022

(54) INFORMATION PROCESSING DEVICE, INFORMATION PROCESSING METHOD, AND PROGRAM

(71) Applicant: Sony Group Corporation, Tokyo (JP)

(72) Inventors: Tetsu Ogawa, Tokyo (JP); Masatoshi Takashima, Tokyo (JP)

(73) Assignee: Sony Group Corporation, Tokyo (JP)

( * ) Notice: Subject to any disclaimer, the term of this patent is extended or adjusted under 35 U.S.C. 154(b) by 1004 days.

(21) Appl. No.: 16/301,607

(22) PCT Filed: Jun. 2, 2017

(86) PCT No.: PCT/JP2017/020635
§ 371 (c)(1),
(2) Date: Nov. 14, 2018

(87) PCT Pub. No.: WO2017/217258
PCT Pub. Date: Dec. 21, 2017

(65) Prior Publication Data
US 2019/0293559 A1 Sep. 26, 2019

(30) Foreign Application Priority Data

Jun. 16, 2016 (JP) .............................. JP2016-119879

(51) Int. Cl.
*G05B 23/02* (2006.01)
*G01N 21/55* (2014.01)
(Continued)

(52) U.S. Cl.
CPC .............. *G01N 21/55* (2013.01); *A01G 7/00* (2013.01); *G01N 21/47* (2013.01); *G01N 21/75* (2013.01);
(Continued)

(58) Field of Classification Search
CPC .......... A01G 7/00; G01N 21/47; G01N 21/55; G01N 21/75; G01N 21/6428;
(Continued)

(56) References Cited

U.S. PATENT DOCUMENTS 11,231,367 B2 * 1/2022 Ogawa ................. G01N 21/648
2012/0316820 A1 12/2012 Nakazato et al.
(Continued)

FOREIGN PATENT DOCUMENTS

CN 1293359 A 5/2001
CN 104884937 A 9/2015
(Continued)

OTHER PUBLICATIONS

Chinese Office Action dated Jul. 19, 2021 for corresponding Chinese Application No. 201780035402.7.
(Continued)

*Primary Examiner* — Hoa Q Pham
(74) *Attorney, Agent, or Firm* — Michael Best & Friedrich LLP

(57) ABSTRACT

The present technology relates to an information processing device capable of obtaining an index effective for a measurement target as an index related to light incident on the measurement target, an information processing method, and a program. The information processing device can obtain an index effective for a measurement target as an index regarding light incident on the measurement target by calculating an effective index representing the degree of light effectively utilized for the measurement target in incident light as an index regarding the light incident on the measurement target, on the basis of a measured value regarding the measurement target which is obtained by sensing performed by a sensor. The present technology can be applied to, for example, an apparatus calculating an index of plants.

18 Claims, 29 Drawing Sheets

(51) Int. Cl.
*A01G 7/00* (2006.01)
*G01N 21/75* (2006.01)
*G01N 33/00* (2006.01)
*G01N 21/47* (2006.01)
*G01N 21/17* (2006.01)

(52) U.S. Cl.
CPC . *G01N 33/0098* (2013.01); *G01N 2021/1789* (2013.01); *G01N 2201/123* (2013.01)

(58) Field of Classification Search
CPC .. G01N 21/648; G01N 21/27; G01N 21/6408; G01N 21/6486; G01N 21/251; G01N 33/483; G01N 33/0098; G01N 2021/1789; G01N 2021/635; G01N 2021/8466; G05B 23/0216; G05B 23/021; G06F 16/9017; G06K 9/00657; G06K 9/60; G06K 9/4652
USPC .................. 356/432–440, 128–137; 702/19
See application file for complete search history.

(56) References Cited

U.S. PATENT DOCUMENTS

| | | | |
|---|---|---|---|
| 2015/0339540 A1 | 11/2015 | Sato | |
| 2019/0369609 A1* | 12/2019 | Takashima | G01N 21/31 |

FOREIGN PATENT DOCUMENTS

| | | |
|---|---|---|
| CN | 105579816 A | 5/2016 |
| EP | 2995915 A1 | 3/2016 |
| JP | 0534199 A | 2/1993 |
| JP | 2004097082 A | 4/2004 |
| JP | 2005214470 A | 8/2005 |
| JP | 2012-163482 A | 8/2012 |
| JP | 2013153691 A | 8/2013 |
| JP | 5575951 B1 | 8/2014 |
| JP | 2015214470 A | 12/2015 |
| JP | 2016102239 A | 6/2016 |
| WO | 2004/077935 A1 | 9/2004 |

OTHER PUBLICATIONS

Zhao Yuminet et al., "Research Progress of Light Use Efficiency of Vegetation", Chinese Journal of Ecology, vol. 26, No. 09 Sep. 30, 2007, pp. 1471-1477.

Japanese Office Action dated Jun. 8, 2021 for corresponding Japanese Application No. 2018-523661.

European Patent Office Communication Pursuant to Article 94(3) dated Dec. 7, 2020 for corresponding European Application No. 17813160.3.

Wiegand C.L. et al., "Multisite Analyses of Spectral-Biophysical Data for Wheat", Database accession No. EIX93010648012, & Remote Sensing of Environment Oct. 1992, vol. 42, No. 1, Oct. 1992 (Oct. 1992), pp. 1-21, DOI: 10.1016/0034-4257(92)90064-Q, Database Compendex [Online] Engineering Information, Inc., New York, NY, US; Oct. 1992 (Oct. 1992).

Gower S. T. et al., "Direct and Indirect Estimation of Leaf Area Index, f(APAR), and Net Primary Production of Terrestrial Ecosystems", Database accession No. E2000275176786 ; & Remote Sensing of Environment Oct. 1999 Elsevier Inc. US, vol. 70, No. 1, Oct. 1999 (Oct. 1999), pp. 29-51, DOI: 10.1016/S0034-4257(99)00056-5, Database Compendex [Online] Engineering Information, Inc., New York, NY, US; Oct. 1999.

Uwe Raschere et al., "Altered Physiological Function, Not Structure, Drives Increased Radiation-Use Efficiency of Soybean Grown at Elevated CO2" Photosynthesis Research: Official Journal of the International Society of Photosynthesis Research, Springer Berlin, DE, vol. 105, No. 1, Apr. 21, 2010, pp. 15-25, XP019828852, ISSN: 1573-5079.

Extended European Search Report dated May 20, 2019 for European Application No. 17813160.3.

* cited by examiner

INFORMATION PROCESSING DEVICE, INFORMATION PROCESSING METHOD, AND PROGRAM

TECHNICAL FIELD

The present technology relates to an information processing device, an information processing method, and a program, and more particularly, to an information processing device capable of obtaining an index effective for a measurement target as an index related to light incident on the measurement target, an information processing method, and a program.

BACKGROUND ART

It is known that photosynthesis of plants is affected by the number of photons which are particles of light rather than by light energy. In addition, Patent Literature 1 discloses technology related to a light quantum meter for measuring a photon flux density effective in photosynthesis of plants.

CITATION LIST

Patent Literature

Patent Literature 1: JP 2012-163482A

DISCLOSURE OF INVENTION

Technical Problem

Incidentally, the light quantum meter disclosed in Patent Literature 1 measures a photon flux density effective in photosynthesis of plants, but a measured index is not limited to being an index effective for plants. For this reason, it is desirable to obtain an index effective for a measurement target as an index related to light incident on any measurement target.

The present technology is contrived in view of such circumstances, and makes it possible to obtain an index effective for a measurement target as an index related to light incident on the measurement target.

Solution to Problem

An information processing device according to an aspect of the present technology is an information processing device including a calculation unit that calculates an effective index representing a degree of light effectively utilized for a measurement target in light incident on the measurement target, as an index regarding the light incident on the measurement target on the basis of a measured value regarding the measurement target obtained by sensing performed by a sensor.

The information processing device according to the aspect of the present technology may be an independent device, or may be an internal block constituting one device. In addition, an information processing method or a program according to another aspect of the present technology is an information processing method or a program which corresponds to the above-described information processing device according to the aspect of the present technology.

In the information processing device, the information processing method, and the program according to the aspects of the present technology, an effective index representing a degree of light effectively utilized for a measurement target in light incident on the measurement target is calculated as an index regarding the light incident on the measurement target on the basis of a measured value regarding the measurement target obtained by sensing performed by a sensor.

Advantageous Effects of Invention

According to an aspect of the present technology, it is possible to obtain an index effective for a measurement target as an index related to light incident on the measurement target.

Moreover, the advantageous effects mentioned here are not necessarily limited and any advantageous effect described in the present disclosure may be obtained.

MODE(S) FOR CARRYING OUT THE INVENTION

Figure 1:
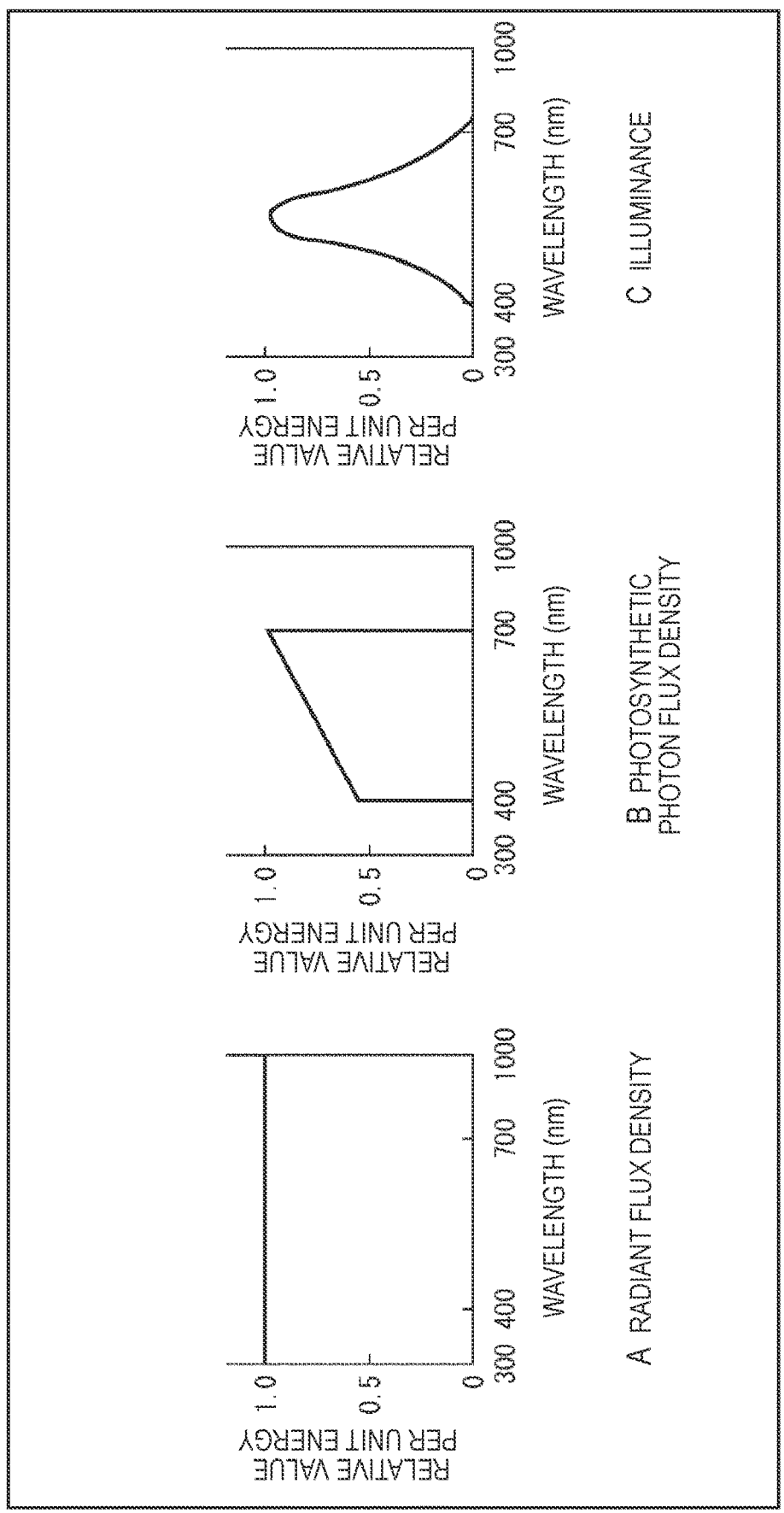
FIG. 1 is a diagram illustrating units related to light.

Hereinafter, embodiments of the present technology will be described with reference to the drawings. Moreover, the description will be made in the following order.
1. Outline of the present technology
2. Configuration of system
3. Procedure of calculation of effective PPFD value
(1) Effective PPFD value calculation process
(2) Example of measurement of sensing device
(3) Photochemical system reaction maximum ETR calculation process
(4) Carbon reduction reaction maximum ETR calculation process
(5) Example of presentation of effective PPFD value and the like
4. Modification example
5. Configuration of computer 1. Outline of the Present Technology FIG. 1 is a diagram illustrating units related to light.

A of FIG. 1 is a diagram illustrating a relative value per unit energy at each wavelength of a radiant flux density. The radiant flux density is the sum of energy intensities for respective wavelengths. Therefore, the same value is obtained at all wavelength, and the overall characteristics are flat. Note that a radiant flux density measured using a filter that passes only a wavelength range of 400 nm to 700 nm effective in photosynthesis is referred to as a photosynthesis radiant flux density.

B of FIG. 1 is a diagram illustrating a relative value per unit energy at each wavelength of a photosynthetic photon flux density. Here, photosynthesis of plants is affected by the number of photons which are particles of light rather than by the energy of light. A photosynthetic photon flux density (PPFD) is indicated by the number of photons incident per unit area in a unit time at a wavelength of 400 nm to 700 nm corresponding to an absorption wavelength of chlorophyll. That is, the photosynthetic photon flux density (PPFD) is a unit expressed by the number of photons which are particles of light rather than by the energy of light.

C of FIG. 1 is a diagram illustrating a relative value per unit energy at each wavelength of illuminance. Illuminance has characteristics matching the sensitivity of human eyes. Therefore, in a case in which light having a constant energy as illustrated in A of FIG. 1 is emitted, there is a characteristic that the energy is set to zero at wavelengths equal to or less than 400 nm and equal to or greater than 700 nm as illustrated in C of FIG. 1. That is, the illuminance is a unit not related to photosynthesis of plants, and it is not possible to evaluate the light environment of plants using this unit.

In plants, light is a very important element in environmental conditions affecting growth, but it is important to consider light as particles here. For this reason, the photosynthetic photon flux density (PPFD) illustrated in B of FIG. 1 is defined as an index indicating how much light incident on plants is effective in photosynthesis. Hereinafter, the photosynthetic photon flux density (PPFD) will also be referred to as a PPFD value.

In addition, the number of photons allowing plants to effectively utilize light is greatly affected by environmental conditions such as temperature, humidity, carbon dioxide ($CO_2$), and nutrients, and the types and states of the plants.

For example, a case in which effective for 500 umol/m$^2$ of light is effective for plants may be considered. A case in which plants are irradiated with 2000 umol/m$^2$ of light for three hours around noon one day and then the sun hardly appears may be assumed. In this case, the total amount of photons is 6000 umol/m$^2$ (2000 umol/m$^2$×3 h), but the amount of photons actually effective for the plants is 1500 umol/m$^2$ (500 umol/m$^2$×3 h).

On the other hand, when a case in which plants are irradiated with 500 umol/m$^2$ of light for six hours is assumed, the total amount of photons is 3000 umol/m$^2$ (500 umol/m$^2$×6 h). In this case, the amount of photons effective for the plants is also 3000 umol/m$^2$ (500 umol/m$^2$×6 h).

Here, comparing the former case and the latter case with each other, it can be said that more effective sunshine is obtained in the latter case in which the amount of effective photons is increased. In this manner, even when a photosynthetic photon flux density (PPFD) of light emitted to the plants can be measured, the measured photosynthetic photon flux density (PPFD) is not always actually effectively utilized for the plants.

(Photochemical System Reaction and Carbon Reduction Reaction of Photosynthesis)

Figure 2:
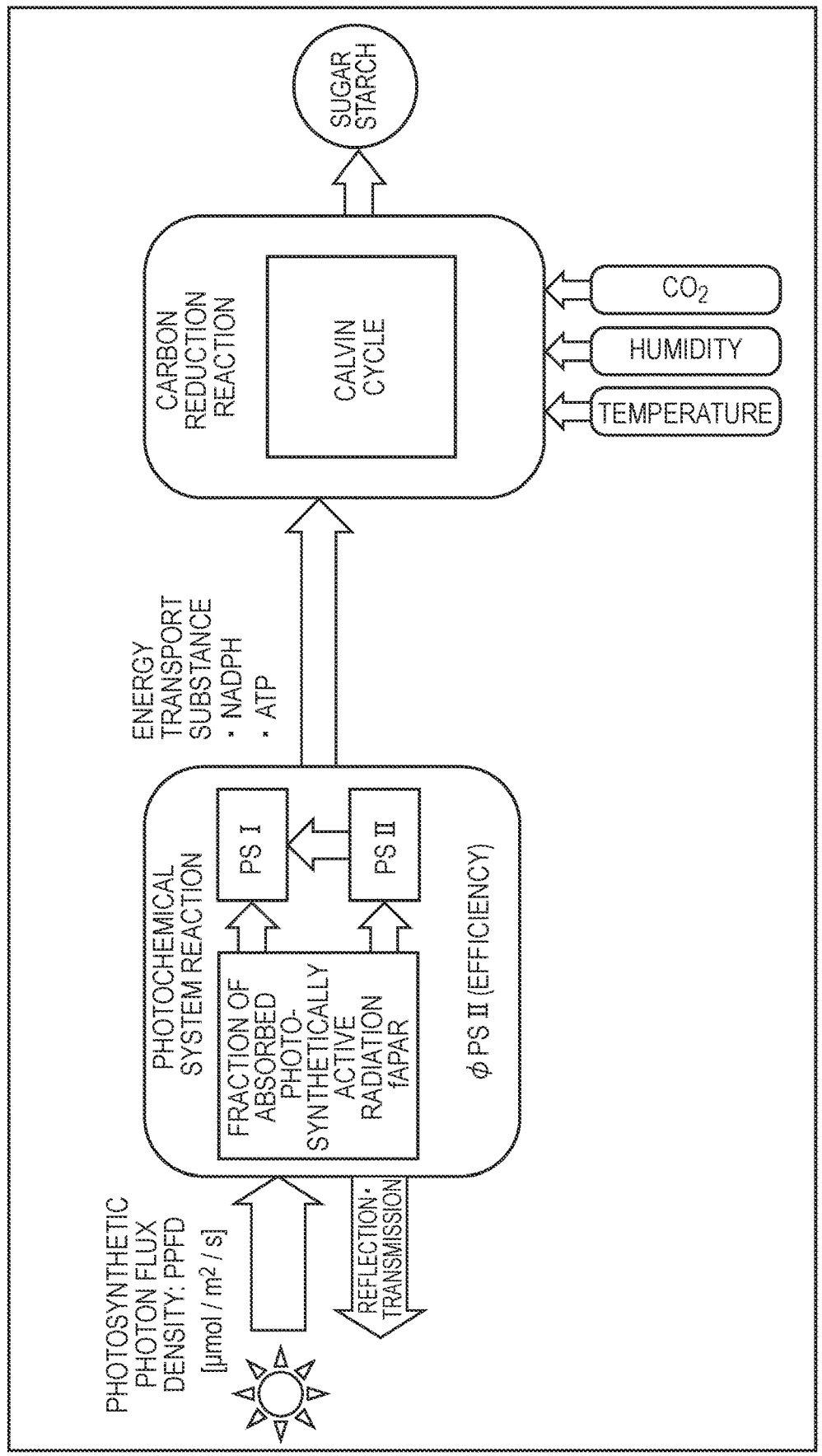
FIG. 2 is a diagram illustrating a photochemical system reaction and a carbon reduction reaction of photosynthesis.

FIG. 2 is a diagram illustrating a photochemical system reaction and a carbon reduction reaction of photosynthesis.

As illustrated in FIG. 2, photosynthesis is broadly classified into two stages which are a photochemical system reaction and a carbon reduction reaction.

The photochemical system reaction (photochemical reaction) in a former stage is a system that converts optical energy into chemical energy. When plants are irradiated with sunlight having a certain PPFD value, reflection and transmission of the light occur in the plants, and thus the amount of light actually absorbed is limited. In addition, a fraction of photosynthetically active radiation (PAR) which is absorbed into plants is referred to as a fraction of absorbed photosynthetically active radiation (fAPAR).

The absorbed light is further separated into a photochemical system I (PSI) and a photochemical system II (ΦPSII), and nicotinamide adenine dinucleotide phosphate (NADPH) and adenosine triphosphate (ATP) as energy transport substances are generated in a quantum yield (ΦPSII) of a photochemical system reaction and transported as energy sources of the carbon reduction reaction in a latter stage.

Here, the quantum yield (ΦPSII) of the photochemical system reaction means an electron transport rate per photoelectron absorbed by chlorophyll of the photochemical system II ΦPSII).

In addition, nicotinamide adenine dinucleotide phosphate (NADPH) present everywhere in a living body is classified into "a reduced type" or "an oxidized type", and has a role of carrying electrons and hydrogen. Adenosine triphosphate (ATP) is widely distributed in a living body, and has an important role in release and storage of energy through the separation and coupling of one molecule of phosphoric acid or in metabolism and synthesis of substances.

The carbon reduction reaction in the latter stage includes a circuit called the Calvin cycle (Calvin circuit). In the Calvin cycle, carbon dioxide ($CO_2$) and water ($H_2O$) are taken in, and nicotinamide adenine dinucleotide phosphate (NADPH) and adenosine triphosphate (ATP) produced in the photochemical system reaction in the latter stage are used as energy by using the carbon dioxide and the water as raw materials, such that sugar and starch are produced.

Here, photosynthesis is a phenomenon in which a photochemical system reaction and a carbon reduction reaction occur in series, and has a structure in which a decrease in the rate of any one of the photochemical system reaction and the carbon reduction reaction causes a bottleneck in any one of the photochemical system reaction and the carbon reduction reaction, according to which the overall rate of photosynthesis is determined.

Figure 3:
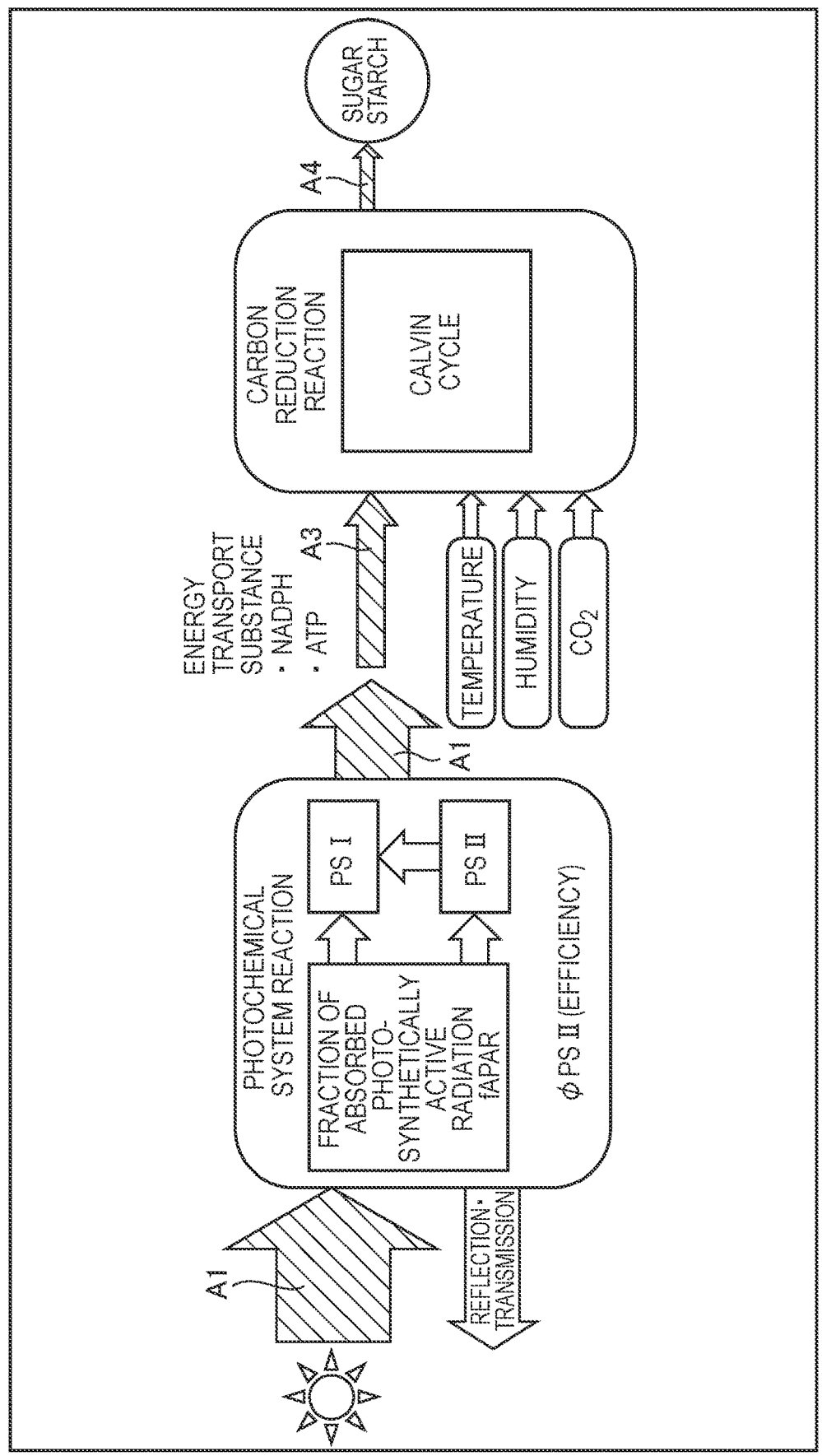
FIG. 3 is a diagram illustrating an example of comparison between a photochemical system reaction and a carbon reduction reaction.

Specifically, in a case in which light effective for plants is 500 umol/m$^2$ as described above, a case in which plants are irradiated with 2000 umol/m$^2$ of light for three hours can be represented by a relationship illustrated in FIG. 3. On the other hand, in a case in which light effective for plants is 500 umol/m$^2$, a case in which plants are irradiated with 500 umol/m$^2$ of light for six hours can be represented by a relationship illustrated in FIG. 4.

Figure 4:
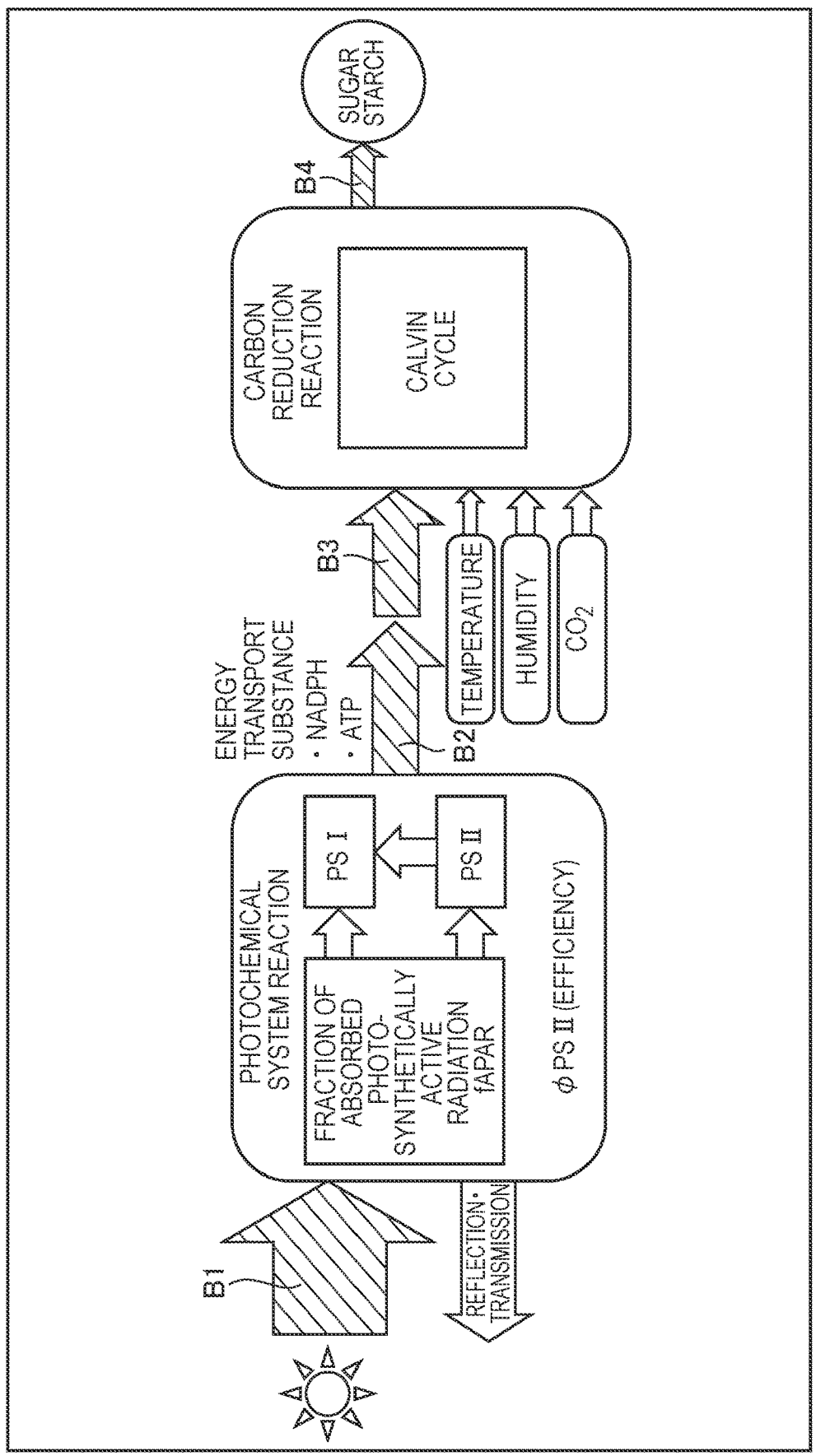
FIG. 4 is a diagram illustrating an example of comparison between a photochemical system reaction and a carbon reduction reaction.

That is, comparing the case illustrated in FIG. 3 and the case illustrated in FIG. 4 with each other, the width of each of arrows A1 to A4 gradually decreases in the case illustrated in FIG. 3, while the width of each of arrows B1 to B4 changes little in the case illustrated in FIG. 4. In this case, the amount of effective photons becomes larger in the case illustrated in FIG. 4 than in the case illustrated in FIG. 3, and thus more effective sunshine is obtained.

In the present technology, it is possible to calculate a photosynthetic photon flux density (PPFD) effective for plants by determining where a bottleneck in a photochemical system reaction and a carbon reduction reaction of photosynthesis occurs. Hereinafter, such a PPFD value is called an effective PPFD value. That is, the effective PPFD value represents the amount of photons considered to have actually contributed to the growth of plants among photons emitted to the plants. Note that umol/m$^2$/s, umol/m$^2$/day, or the like can be used as the unit of the effective PPFD value, similar to a case of the effective PPFD value.

Figure 5:
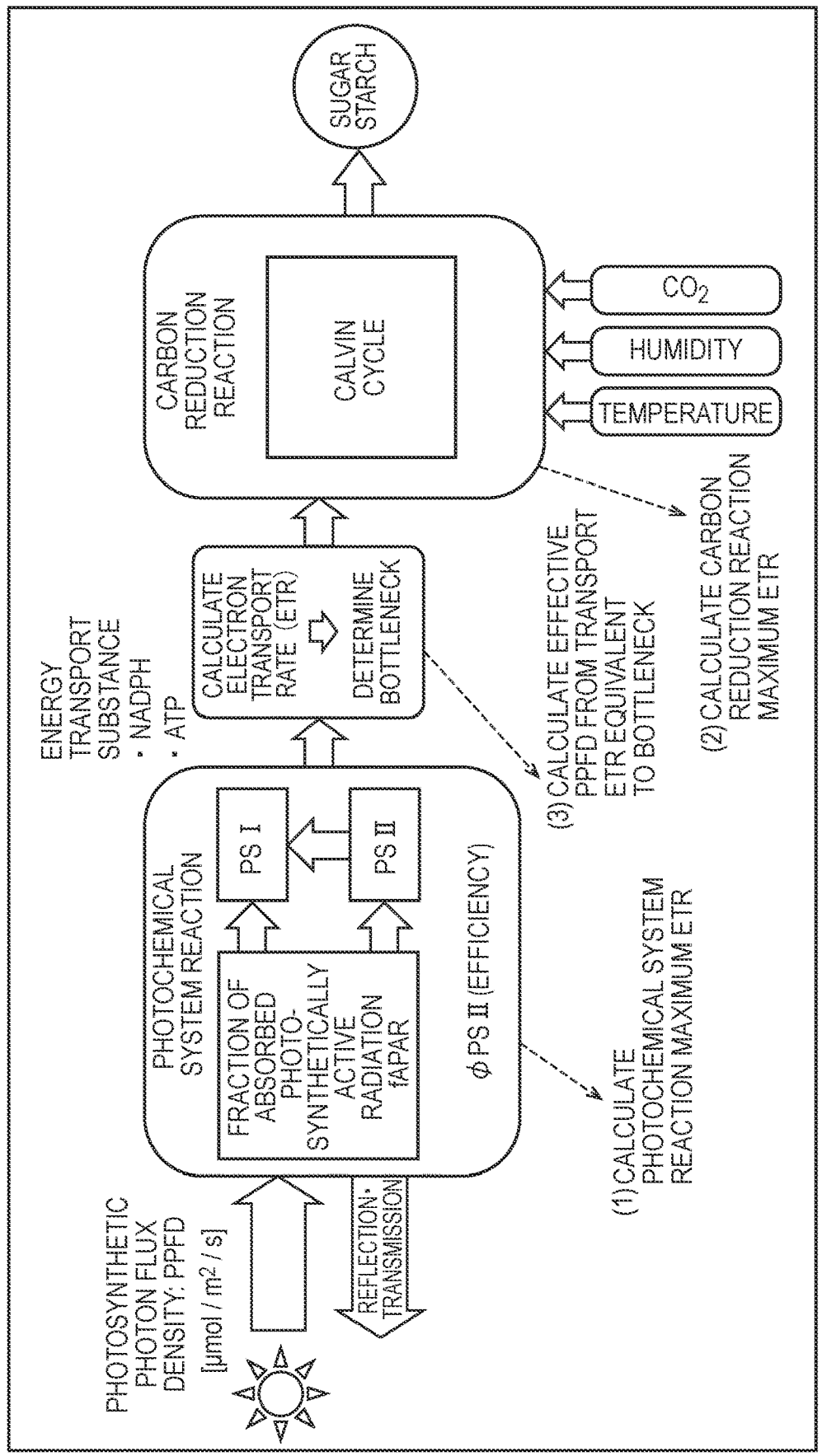
FIG. 5 is a diagram illustrating a procedure of calculation of an effective PPFD value.

Here, the procedure of calculation of the effective PPFD value can be represented by three procedures illustrated in FIG. 5.

That is, as a first procedure, an electron transport rate (ETR) equivalent to the energy output from a photochemical system reaction is calculated as a photochemical system reaction maximum ETR. The photochemical system reaction maximum ETR represents the maximum electron transport rate (ETR) determined by a photochemical system reaction capacity of plants when a photochemical system reaction and a carbon reduction reaction are separated from each other. The unit of the photochemical system reaction maximum ETR is umol/m$^2$/s.

Next, as a second procedure, an electron transport rate (ETR) equivalent to a maximum photosynthesis rate of a carbon reduction reaction determined from an environment or types of plants is calculated as a carbon reduction reaction maximum ETR. The carbon reduction reaction maximum ETR represents a maximum electron transport rate (ETR) determined by a carbon reduction reaction capacity of plants when a photochemical system reaction and a carbon reduction reaction are separated from each other. The unit of the carbon reduction reaction maximum ETR is umol/m$^2$/s.

In addition, as a third procedure, a bottleneck is determined (identified) from the photochemical system reaction maximum ETR calculated through the first procedure and the carbon reduction reaction maximum ETR calculated through the second procedure, and a PPFD value equivalent to the bottleneck is calculated as an effective PPFD value from a transport ETR equivalent to the bottleneck. The transport ETR represents an electron transport rate (ETR) depending on the rate of photosynthesis of plants which is calculated from the photochemical system reaction maximum ETR and the carbon reduction reaction maximum ETR. The unit of the transport ETR is umol/m$^2$/s.

Note that an electron transport rate (ETR) represents the amount of redox (so-called electron transport activity) per unit time of an electron transport complex. A photosynthesis electron transport system includes a reaction center complex (a photochemical system I, a photochemical system II, photosynthesis bacteria), a cytochrome complex, and the like. Electrons are exchanged between complexes by movable electron carriers such as plastocyanin and cytochromes. The unit of the electron transport rate (ETR) is umol/m$^2$/s.

Hereinafter, a method of calculating an effective PPFD value according to the present technology will be described.

2. Configuration of System (Configuration of Effective Index Computation System)

Figure 6:
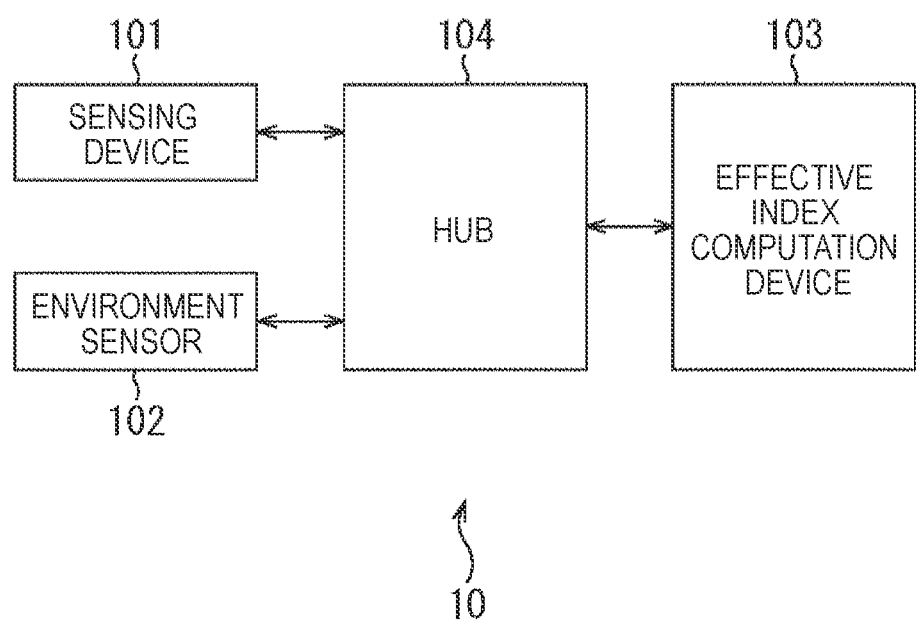
FIG. 6 is a diagram illustrating a configuration of an embodiment of an effective index computation system to which the present technology is applied.

FIG. 6 is a diagram illustrating a configuration of an embodiment of an effective index computation system to which the present technology is applied.

An effective index computation system 10 is a system that senses a measurement target and calculates an effective index such as an effective PPFD value on the basis of a result of the sensing. That is, in the effective index computation system 10, in a case in which plants (vegetation) are set to be a measurement target and a photosynthetic photon flux density (PPFD) value is obtained as the index (measurement index) thereof, an effective PPFD value is calculated as an effective index.

In FIG. 6, the effective index computation system 10 includes a sensing device 101, an environment sensor 102, and an effective index computation device 103. The sensing device 101, the environment sensor 102, and the effective index computation device 103 are connected to each other through a hub 104.

The sensing device 101 senses a measurement target and outputs data obtained by the sensing. Here, the sensing means measurement of the measurement target. In addition, the sensing includes imaging of the measurement target. In addition, an image obtained by imaging the measurement target includes not only a visible image obtained from visible light but also an image obtained from light, such as infrared light (infrared rays), other than visible light. In this manner, a measured signal obtained by the sensing includes an image, but may be information other than an image.

The sensing device 101 senses a measurement target, and outputs a measurement result thereof to the effective index computation device 103 through the hub 104 as index measurement data. The index measurement data is data for obtaining indexes such as a PPFD value and an NDVI value. Here, a normalized difference vegetation index (NDVI) is an index indicating the distribution state and the degree of activity of vegetation. Here, the normalized difference vegetation index (NDVI) is an example of a vegetation index.

Note that a detailed configuration of the sensing device 101 will be described later with reference to FIG. 7.

The environment sensor 102 is a sensor for measuring an air environment such as a temperature, a humidity, and a $CO_2$ concentration. The environment sensor 102 senses a temperature, a humidity, and a $CO_2$ concentration in the air in the vicinity of a measurement target, and outputs measurement results thereof to the effective index computation device 103 through the hub 104 as environment measurement data.

The effective index computation device 103 is a device having an arithmetic operation function using a circuit such as a Central Processing Unit (CPU) or a Field Programmable Gate Array (FPGA). For example, the effective index computation device 103 may be configured as a personal computer, a dedicated terminal device, or the like. The index measurement data output from the sensing device 101 and the environment measurement data output from the environment sensor 102 are input to the effective index computation device 103 through the hub 104.

The effective index computation device 103 calculates an effective PPFD value on the basis of the index measurement data and the environment measurement data. Here, it is possible to calculate the effective PPFD value as an effective index with respect to an index which is a PPFD value by executing processing equivalent to the first to third procedures illustrated in FIG. 5.

Note that a detailed configuration of the effective index computation device 103 will be described later with reference to FIG. 8.

The effective index computation system 10 is configured as follows.

(Configuration of Sensing Device)

Figure 7:
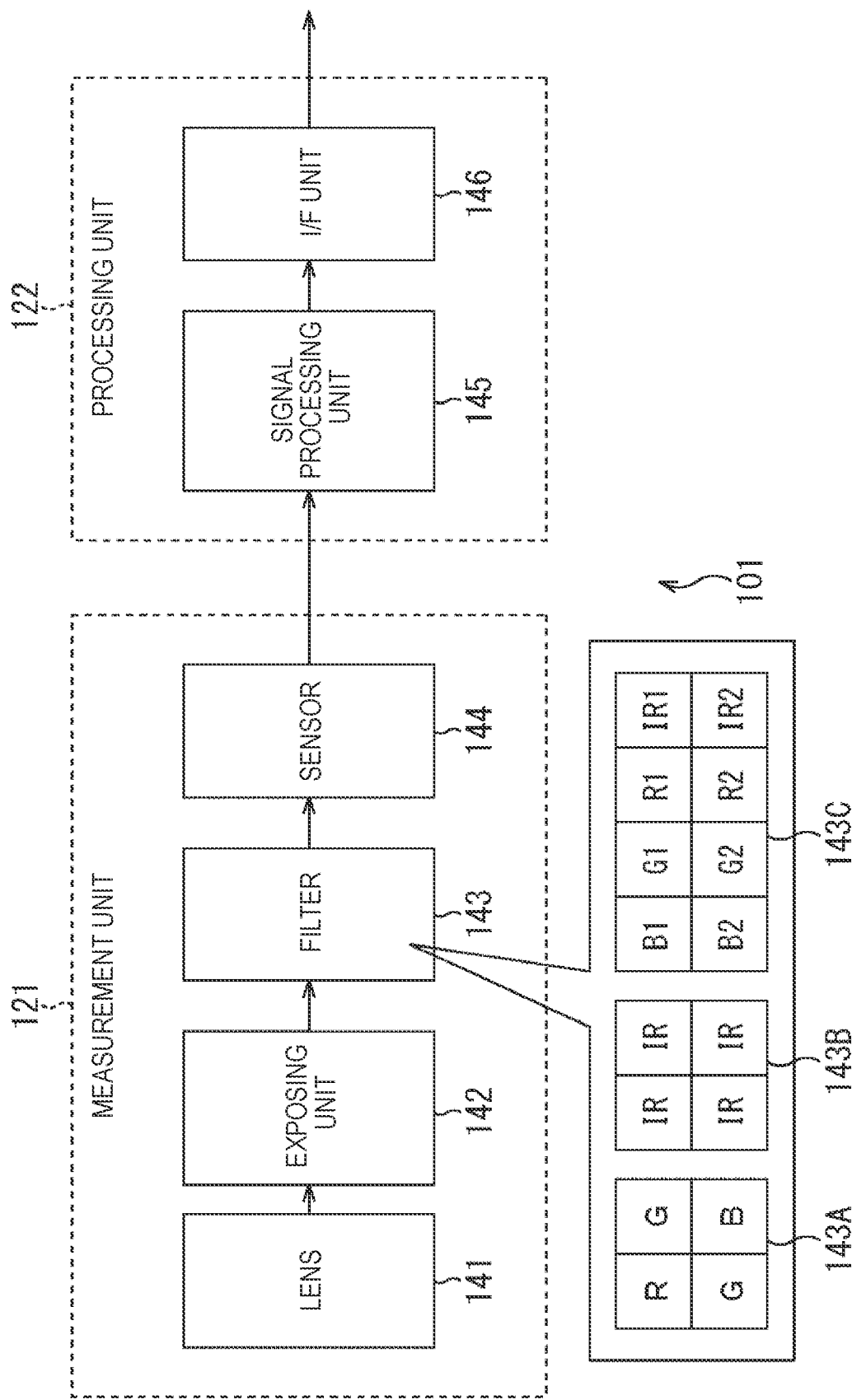
FIG. 7 is a diagram illustrating a configuration example of a sensing device.

FIG. 7 is a diagram illustrating a configuration example of the sensing device 101 of FIG. 6.

In FIG. 7, the sensing device 101 includes a measurement unit 121 including a lens 141, an exposing unit 142 a filter 143, and a sensor 144, and a processing unit 122 including a signal processing unit 145 and an I/F unit 146.

In the sensing device 101, light (reflected light) from an object such as a measurement target is incident on the sensor 144 through the lens 141 and the filter 143.

The exposing unit 142 performs exposure control by adjusting an aperture amount of an optical system such as the lens 141 or an iris (diaphragm), and the like so that sensing is performed in the sensor 144 in a state where a signal charge is within a dynamic range without being saturated. However, the exposure control can also be performed by remote control from the effective index computation device 103.

The filter 143 is an optical filter based on an index to be measured (measurement index). The filter 143 transmits light incident through the lens 141 to the sensor 144.

The sensor 144 is a sensor including a pixel array portion in which a plurality of pixels are two-dimensionally arranged on the surface of the sensor. The sensor 144 senses light having passed through the filter 143 using the plurality of pixels two-dimensionally arranged in the pixel array portion, and outputs a measured signal (measurement data) based on the amount of light to the signal processing unit 145.

Note that the filter 143 can be configured as an on-chip filter on a plurality of pixels two-dimensionally arranged in the pixel array portion of the sensor 144.

Here, for example, in a case in which a PPFD value is calculated as an index, an RGB signal is required, and thus a combination of an RGB filter and an IR cut filter is provided as the filter 143. In this case, in the pixel array portion of the sensor 144, a plurality of pixels can be two-dimensionally arranged in a Bayer array, for example, as indicated by an arrangement pattern 143A for a color filter of FIG. 7.

Here, the Bayer array is an arrangement pattern in which green (G) pixels are arranged in a checkerboard form, and red (R) pixels and blue (B) pixels are alternately arranged in every row in the remaining portions. In addition, the arrangement pattern of the color filter is not limited to the Bayer array shown as the arrangement pattern 143A, and other arrangement patterns may be adopted. Note that, filters in visible regions such as red (R), green (G), and blue (B) are provided, and thus it is possible to capture images to be presented to a user and to simultaneously present the images.

In addition, for example, in a case in which an NDVI value is calculated as an index, an IR signal is required together with an R signal, and thus an IR filter is provided as the filter 143. In this case, for example, in the effective index computation system 10, two sensing devices 101 are provided, so that an RGB filter constituted by the arrangement pattern 143A is provided as the filter 143 for one sensing device 101 and an IR filter constituted by an arrangement pattern 143B is provided as the filter 143 for the other sensing device 101.

In this case, in the other sensing device 101, all of the pixels can be two-dimensionally arranged as IR pixels corresponding to components in infrared regions (IR) in the pixel array portion of the sensor 144, for example, as indicated by the arrangement pattern 143B as the color filter of FIG. 7. Note that, in the present specification, infrared light is also one of colors, and it is assumed that the color filter also includes an IR filter transmitting a wavelength of infrared light.

Note that, although an example of the filter 143 used in a case in which two sensing devices 101 are provided in the effective index computation system 10 has been described above, a filter having a combination of RGB and IR may be provided as the filter 143 in a case in which one sensing device 101 copes with the calculation of a PPFD value and an NDVI value.

That is, in this case, IR pixels corresponding to components in infrared regions (IR) are arranged in the pixel array portion of the sensor 144, in addition to R, G, and B pixels corresponding to an RGB filter transmitting wavelengths of red (R), green (G), and blue (B) visible light, for example, as indicated by the arrangement pattern 143C for the color filter of FIG. 7.

In the arrangement pattern 143C in FIG. 7, for example, four pixels are arranged in the transverse direction and two pixels are arranged in the longitudinal direction so that 4×2 pixels (two R pixels (R1, R2), two G pixels (G1, G2), two B pixels (B1, B2), two IR pixels (IR1, IR2)) are made one set. Then, such eight pixels are made one set, and a plurality of pixels that constitutes n (n is an integer of one or more) sets is arranged repeatedly on the surface of the pixel array portion. In this connection, the number of pixels per one set is not limited to eight pixels, and, for example, other forms such as a constitution in which four pixels including one R pixel, one G pixel, one B pixel, and one IR pixel, are made one set, may be adopted.

Note that, in a case in which a PPFD value is calculated as an index, an optical filter corresponding to a PPFD value may be provided as the filter 143, instead of an RGB filter and an IR cut filter. That is, the optical filter corresponding to the PPFD value is a filter for allowing the sensor 144 in the latter stage to be able to detect light based on the PPFD value. Therefore, light having passed through the filter 143 has the same characteristics as those of the photosynthetic photon flux density (PPFD) illustrated in B of FIG. 1.

The signal processing unit 145 performs predetermined signal processing such as a process of rearranging pieces of data on measurement data output from the sensor 144, and outputs the processed data to the I/F unit 146.

Note that, although a description will be given in the present embodiment on the assumption that an index such as an NDVI value or a PPFD value is calculated by the effective index computation device 103 provided at the rear stage, the signal processing unit 145 may be constituted by a circuit such as a CPU or an FPGA to calculate an index such as an NDVI value or a PPFD value on the basis of measurement data.

The I/F unit 146 is constituted by an external output interface circuit or the like, and outputs measurement data supplied from the signal processing unit 145 to the effective index computation device 103 through the hub 104 as index measurement data.

The sensing device 101 is configured as described above.

Note that, in the following description, sometimes a plurality of sensing devices 101 are provided in the effective index computation system 10. In such a case, a distinction will be made by adding "−1" and "−2" as signs. In addition, a distinction will be made in the same manner with respect to the filter 143, the sensor 144, and the like within the sensing device 101.

(Configuration of Effective Index Computational Device)

Figure 8:
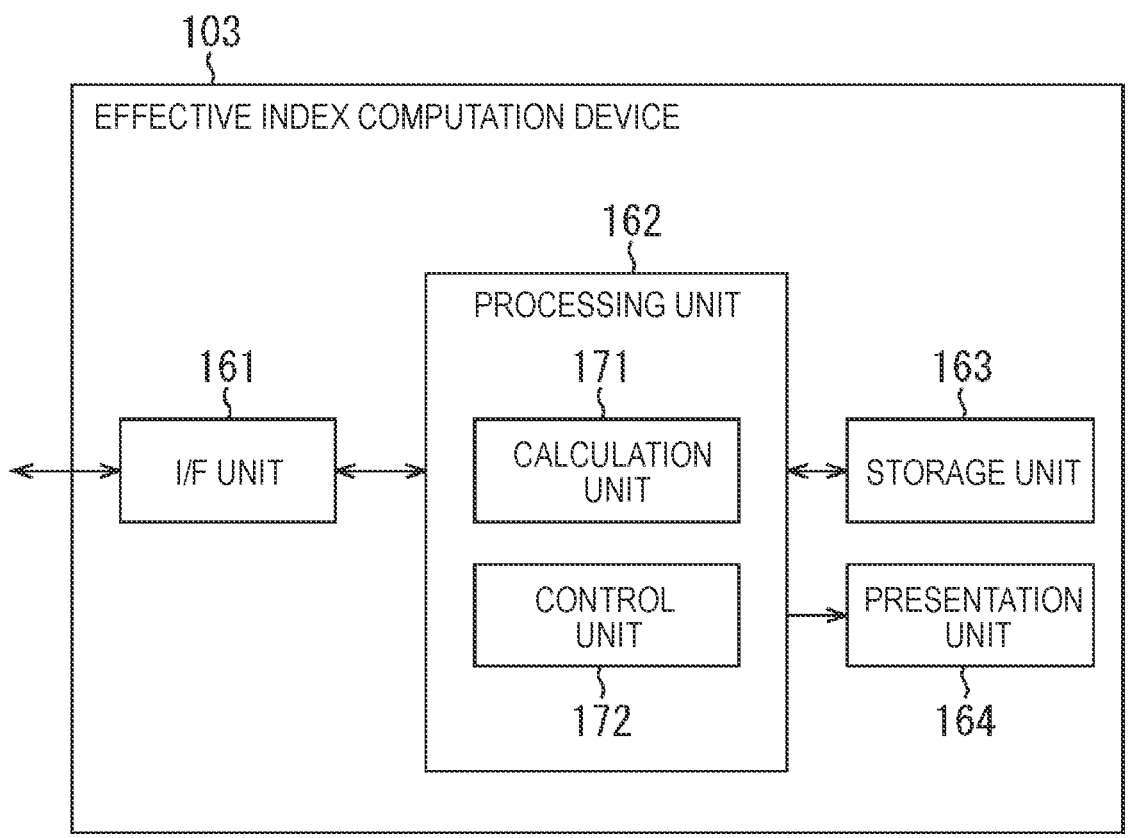
FIG. 8 is a diagram illustrating a configuration example of an effective index computation device.

FIG. 8 is a diagram illustrating a configuration example of the effective index computation device 103 of FIG. 6.

In FIG. 8, the effective index computation device 103 includes an I/F unit 161, a processing unit 162, a storage unit 163, and a presentation unit 164.

The I/F unit 161 is constituted by an external input interface circuit or the like, and supplies the index measurement data input from the sensing device 101 and the environment measurement data input from the environment sensor 102 to the processing unit 162.

The processing unit 162 is constituted by a circuit such as a CPU or an FPGA. The processing unit 162 includes a calculation unit 171 and a control unit 172.

The calculation unit 171 calculates an effective PPFD value by performing predetermined signal processing on the index measurement data and the environment measurement data supplied from the I/F unit 161 while referring to a look-up table (LUT) stored in the storage unit 163.

Although details of the signal processing will be described later, a photochemical system reaction maximum ETR calculation process and a carbon reduction reaction maximum ETR calculation process are executed as processes equivalent to the first to third procedures illustrated in FIG. 5, and a photochemical system reaction maximum ETR and a carbon reduction reaction maximum ETR obtained as a result of the processes are compared with each other to determine a bottleneck. In addition, a PPFD value equivalent to an ETR (transport ETR) based on the bottleneck is calculated as an effective PPFD value.

The control unit 172 controls the operation of each unit of the effective index computation device 103. For example, the control unit 172 controls the display of information according to various data, such as numerical data and image data, which is displayed on the presentation unit 164. In addition, the control unit 172 can control external devices such as the sensing device 101 and the environment sensor 102.

The storage unit 163 is constituted by, for example, a semiconductor memory or the like. The storage unit 163 stores various data such as numerical data and image data under the control of the control unit 172. In addition, the storage unit 163 has a look-up table (LUT) for calculating an effective PPFD value stored therein in advance.

Although details will be described later, for example, a coefficient calculation LUT (LUT1), a fAPAR calculation LUT (LUT2), a $\Phi$PSII calculation LUT (LUT3), a $CO_2$ rate limiting photosynthesis rate LUT (LUT4), a temperature correction coefficient LUT (LUT5), and a humidity correction coefficient LUT (LUT6) are stored as the look-up table. Note that reference information for calculating values thereof is not limited to the look-up table, and for example, a predetermined function may be stored. In this case, it is possible to obtain a value by solving, for example, a linear or non-linear equation provided as the predetermined function.

The presentation unit 164 is constituted by a display such as a Liquid Crystal Display (LCD) or an Organic Electroluminescence Display (OELD), a speaker, or the like. The presentation unit 164 presents presentation information including information regarding the effective PPFD value calculated by the calculation unit 171 under the control of the control unit 172. In addition, the presentation unit 164 can present the presentation information stored in the storage unit 163 under the control of the control unit 172. Here, for example, in a case in which the presentation unit 164 is configured as a display, it is possible to display a numerical value, an image, text information, and the like based on the effective PPFD value as the presentation information.

Note that a description has been given in FIG. 8 on the assumption that the storage unit 163 and the presentation unit 164 are provided inside the effective index computation device 103, but the storage unit and the presentation unit may be provided outside the effective index computation device 103 as a storage device and a display device. In this case, the calculation unit 171 acquires a look-up table from an external storage device through a network. In addition, the control unit 172 can display information based on various data, such as numerical data and image data, which are obtained by signal processing on an external display device, or can store the information in the external storage device.

The effective index computation device 103 is configured as described above.

(Other Configurations of Effective Index Computational System)

Incidentally, in the effective index computation system 10 illustrated in FIG. 6, the effective index computation device 103 such as a personal computer calculates an effective PPFD value in a local environment through the hub 104, but the effective PPFD value may be calculated in a cloud environment through a network.

Figure 9:
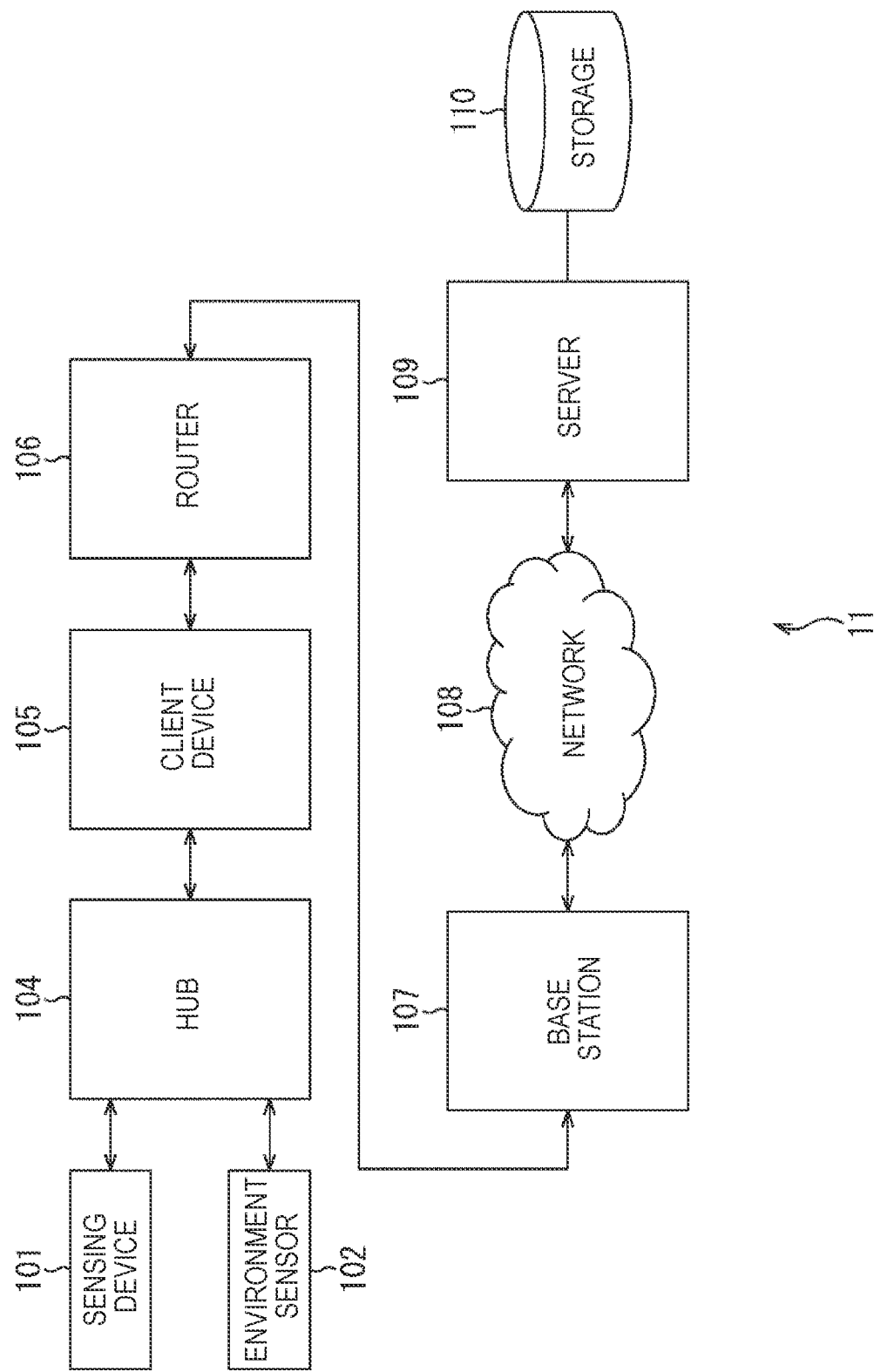
FIG. 9 is a diagram illustrating another configuration example of the effective index computation system.

FIG. 9 illustrates a configuration example of an effective index computation system 11 corresponding to a cloud environment as another configuration example of the effective index computational system.

In the effective index computation system 11 of FIG. 9, the sensing device 101 and the environment sensor 102 measure index measurement data and environment measurement data and output the measured data to the client device 105 through the hub 104, similar to the sensing device 101 and the environment sensor 102 of FIG. 6.

The client device 105 is constituted by a personal computer or the like, and outputs the index measurement data and the environment measurement data which are input from the sensing device 101 and the environment sensor 102 to the router 106 through the hub 104.

The router 106 is, for example, a router for mobile, and can be connected to a network 108 such as the Internet through a base station 107. The router 106 transmits index measurement data and environment measurement data to be input from the client device 105 to a server 109 through the network 108.

The server 109 receives the index measurement data and environment measurement data transmitted from the client device 105 through the network 108. Here, the server 109 has at least the same functions as those of the processing unit 162 and the storage unit 163 among the functions of the effective index computation device 103 illustrated in FIG. 8.

That is, in the server 109, the calculation unit 171 of the processing unit 162 executes processes equivalent to the first to third procedures illustrated in FIG. 5 by performing predetermined signal processing on the index measurement data and the environment measurement data received from the client device 105 while referring to the look-up table stored in the storage unit 163, and calculates an effective PPFD value.

In a case in which the server 109 includes the presentation unit 164 or the server 109 and the presentation unit 164 can communicate with each other, presentation information including information regarding the effective PPFD value obtained through the signal processing performed by the calculation unit 171 can be presented to the presentation unit 164. In addition, data of various presentation information may be stored in the storage 110. The server 109 can also read out the data of various presentation information stored in the storage 110 and present the read-out data to the presentation unit 164.

The effective index computation system 11 is configured as described above.

3. Procedure of Calculation of Effective PPFD Value (1) Effective PPFD Value Calculation Process
(Flow of Effective PPFD Value Calculation Process)

First, a flow of an effective PPFD value calculation process executed by the effective index computation system 10 of FIG. 6 will be described with reference to a flowchart of FIG. 10.

In step S101, the sensing device 101 and the environment sensor 102 perform sensing to acquire data obtained by the sensing.

Here, index measurement data obtained by the sensing performed by the sensing device 101 and environment measurement data obtained by the sensing performed by the environment sensor 102 are output to the effective index computation device 103 through the hub 104. Note that an example of measurement of a measurement target by the sensing device 101 will be described later with reference to FIGS. 11 to 14.

In step S102, the calculation unit 171 of the effective index computation device 103 performs a photochemical system reaction maximum ETR calculation process on the basis of the data obtained in the process of step S101.

In the photochemical system reaction maximum ETR calculation process, a process equivalent to the above-described first procedure illustrated in FIG. 5 is performed, and an electron transport rate (ETR) equivalent to energy output from a photochemical system reaction is calculated as a photochemical system reaction maximum ETR. Note that details of the photochemical system reaction maximum ETR calculation process will be described with reference to FIGS. 15 to 19.

In step S103, the calculation unit 171 of the effective index computation device 103 performs a carbon reduction reaction maximum ETR calculation process on the basis of the data obtained in the process of step S101.

In the carbon reduction reaction maximum ETR calculation process, a process equivalent to the above-described second procedure illustrated in FIG. 5 is performed, and an electron transport rate (ETR) equivalent to a maximum photosynthesis rate of a carbon reduction reaction determined from an environment and types of plants is calculated as a carbon reduction reaction maximum ETR. Note that details of the carbon reduction reaction maximum ETR calculation process will be described later with reference to FIGS. 20 and 21.

In step S104, the calculation unit 171 of the effective index computation device 103 compares the photochemical system reaction maximum ETR calculated in the process of step S102 and the carbon reduction reaction maximum ETR calculated in the process of step S103 with each other, and determines a bottleneck in accordance with a result of the comparison.

Here, the photochemical system reaction maximum ETR which is a maximum value of a photochemical system reaction and the carbon reduction reaction maximum ETR which is a maximum value of a carbon reduction reaction are compared with each other, and a smaller value is determined to be a bottleneck. That is, when the photochemical system reaction maximum ETR is smaller, a photochemical system reaction is rate-limited at the current photosynthesis rate. In contrast, when the carbon reduction reaction maximum ETR is smaller, a carbon reduction reaction is rate-limited at the current photosynthesis rate.

In step S105, the calculation unit 171 of the effective index computation device 103 calculates a PPFD value equivalent to the smaller ETR (this amount flows through plants as a transport ETR and contributes to growth of the plants) as an effective PPFD value in accordance with the bottleneck determined in the process of step S104. The effective PPFD value can be calculated by the following Expression (1).

$$\text{Effective PPFD value} = \text{transport } ETR/(fAPAR \times m \times \Phi_{SII}) \quad (1)$$

Here, in Expression (1), m represents a distribution rate to PSII in light (sunlight) emitted to the plants, and indicates a value of approximately 0.5.

Note that the processes of step S104 and step S105 are processes equivalent to the above-described third procedure illustrated in FIG. 5.

In step S106, the control unit 172 of the effective index computation device 103 presents presentation information including information regarding the effective PPFD value calculated in the process of step S105 to the presentation unit 164.

Here, in addition to the effective PPFD value, various pieces of presentation information, such as the photochemical system reaction maximum ETR, the carbon reduction reaction maximum ETR, the transport ETR, and the PPFE value, which are related to the effective PPFD value can be displayed on the presentation unit 164 in various display forms. Note that an example of display of presentation information such as an effective PPFD value will be described later with reference to FIGS. 22 to 28.

In step S107, it is determined whether or not to terminate the processing in accordance with, for example, a user's instruction. In a case in which it is determined in step S107 that the processing is not terminated, the processing returns to step S101, and the above-described processes of steps S101 to S106 are repeated.

Thereby, in the effective index computation device 103, information regarding the effective PPFD value calculated in the process of step S105 can be accumulated in the storage unit 163 or the like in time series. Note that, in the present specification, the accumulation means that data is recorded temporarily or permanently. Further, in a case in which it is determined in step S107 that the processing is terminated, the effective PPFD value calculation process of FIG. 10 is terminated.

The flow of the effective PPFD value calculation process has been described above.

Figure 10:
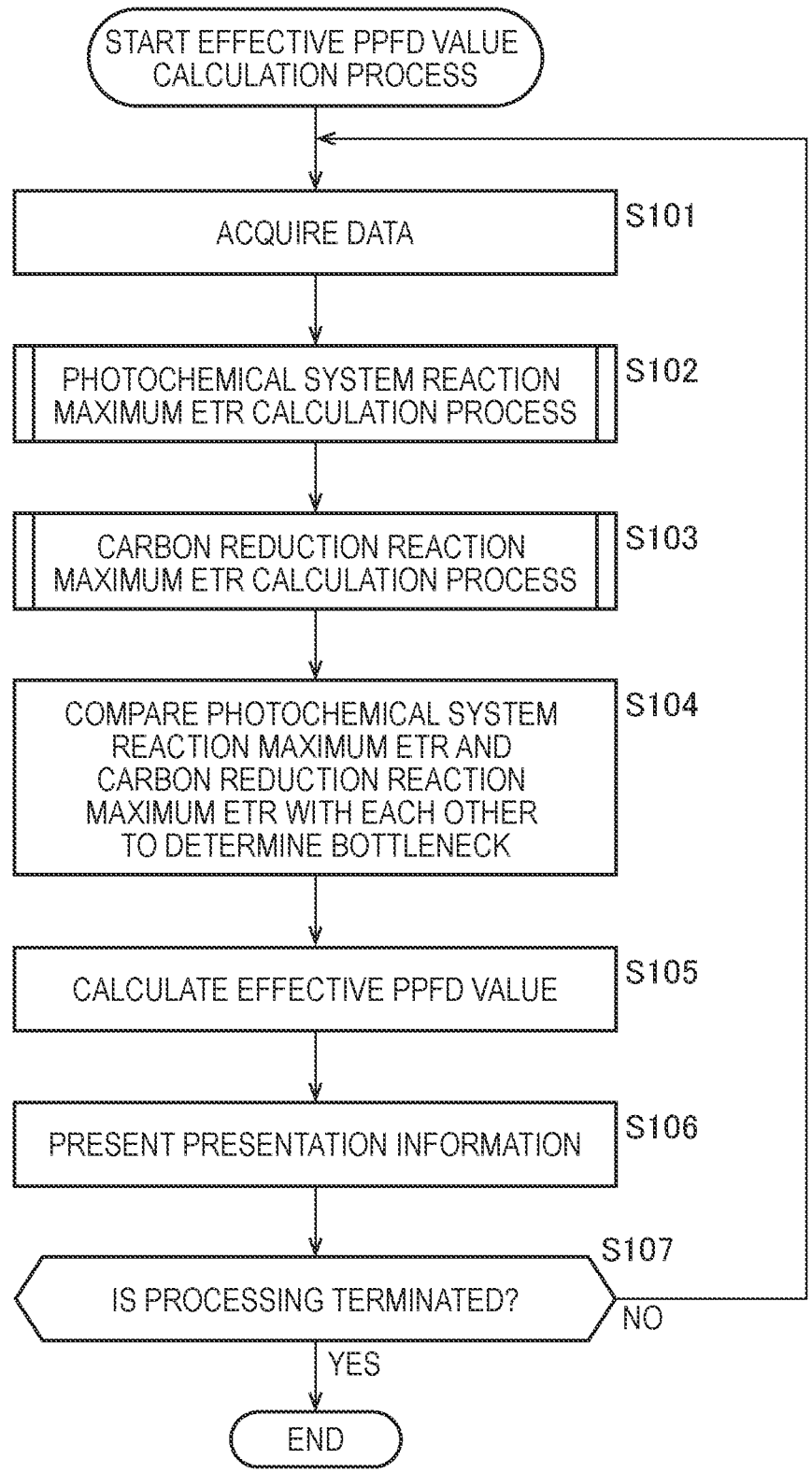
FIG. 10 is a flowchart illustrating a flow of an effective PPFD value calculation process.

Note that, in the description of FIG. 10, the process of step S101 is executed by the sensing device 101 and the environment sensor 102, and the processes of steps S102 to S106 are executed by the effective index computation device 103, but the processes of steps S102 to S106 may be executed by a device other than the effective index computation device 103.

For example, although details will be described later, it is necessary to obtain an index such as a PPFD value or an NDVI value in the process of step S102, and a process of obtaining the index may be executed by the sensing device 101. Further, in a case in which a configuration of the effective index computation system 11 (FIG. 9) as a cloud environment is adopted instead of a configuration of the effective index computation system 10 (FIG. 6) as a local environment, for example, the server 109 can execute the processes of steps S102 to S106.

(2) Example of Measurement to be Performed by Sensing Device

Next, an example of measurement of a measurement target which is executed by the sensing device 101 will be described with reference to FIGS. 11 to 14.

(Configuration Example During Measurement of Sensing Device)

Figure 11:
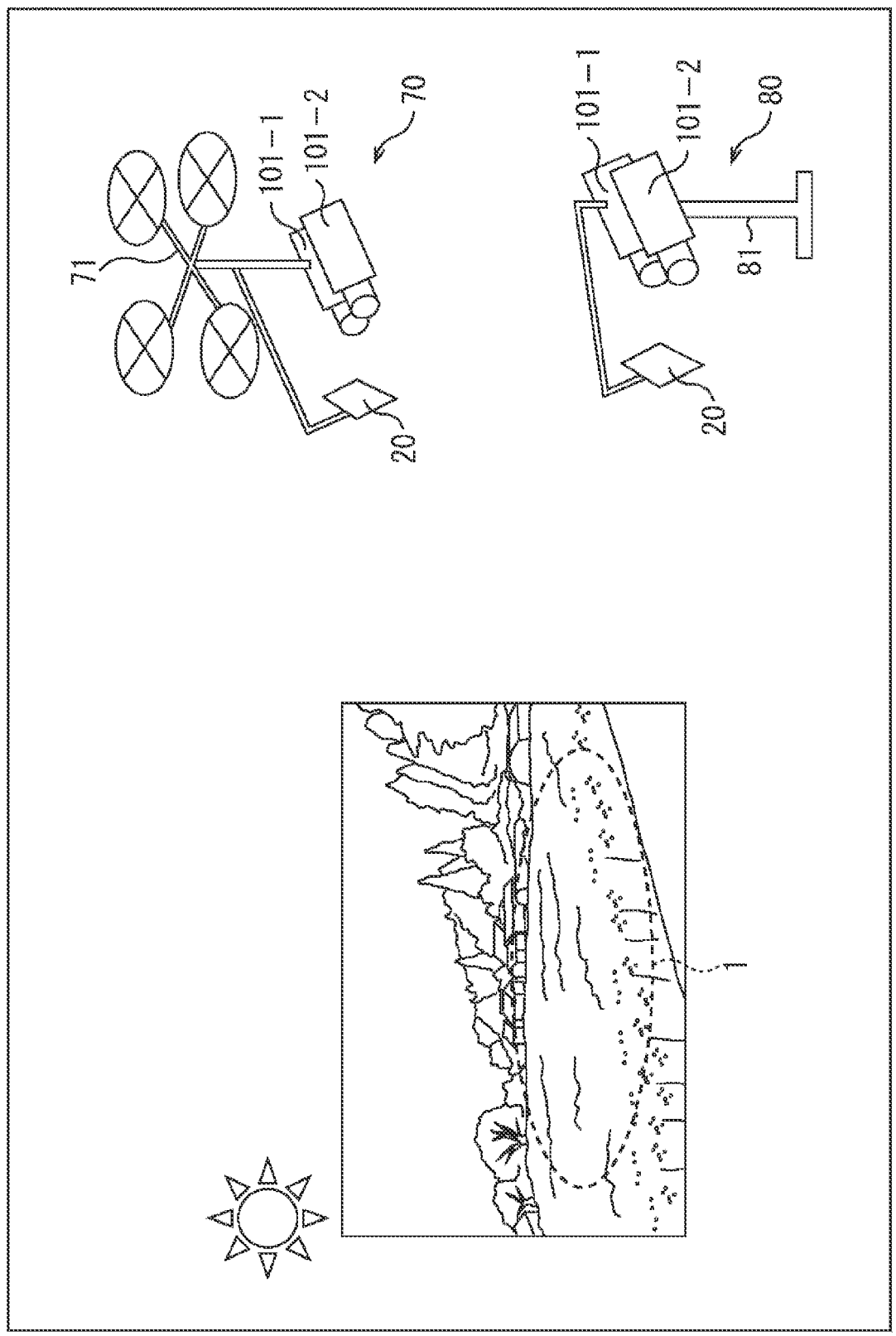
FIG. 11 is a diagram illustrating an example of measurement of the sensing device.

FIG. 11 illustrates a moving measurement device 70 performing movement observation and a fixed-point measurement device 80 performing fixed-point observation as measurement devices for measuring a measurement target.

A mobile measuring device 70, which is, for example, an unmanned aerial vehicle (UAV), flies by the rotation of a rotary wing 71 having a propeller shape and senses (aerial imaging) a measurement target 1 such as plants in a field from the sky.

The mobile measuring device 70 includes a sensing device 101-1 for measuring PPFD values and a sensing device 101-2 for measuring NDVI values. In addition, a reference reflecting plate 20 having a predetermined shape (for example, a rectangular shape) is installed in front of the sensing device 101-1 and the sensing device 101-2.

Thereby, in the mobile measuring device 70, the measurement target 1 such as plants in a field and the reference reflecting plate 20 are present within the same angle of view as objects (subjects) to be sensed by the sensing device 101-1 and the sensing device 101-2. For example, a gray reflecting plate having a fixed reflectance can be used as the reference reflecting plate 20.

Note that, the mobile measuring device 70, in addition to radio control, for example, may be made to perform autonomous flight by memorizing beforehand a flight route as coordinate data and using position information, such as GPS (Global Positioning System). Moreover, although, in FIG. 11, the description has been given for a case where the mobile measuring device 70 is a rotary wing aircraft with the rotary wings 71, the mobile measuring device 70 may be a fixed-wing aircraft.

The fixed-point measurement device 80 is fixed to a position where a measurement target 1 such as plants in a field can be sensed, using a fixing leg 81. The fixed-point measurement device 80 includes a sensing device 101-1 for measuring a PPFD value and a sensing device 101-2 for measuring an NDVI value similar to the moving measurement device 70, and a reference reflecting plate 20 having a predetermined shape is installed in front of the fixed-point measurement device.

That is, the sensing device 101-1 and the sensing device 101-2, which are configured as a portion of the moving measurement device 70 or the fixed-point measurement device 80, can sense the measurement target 1 and output index measurement data obtained as a result of the sensing.

Figure 12:
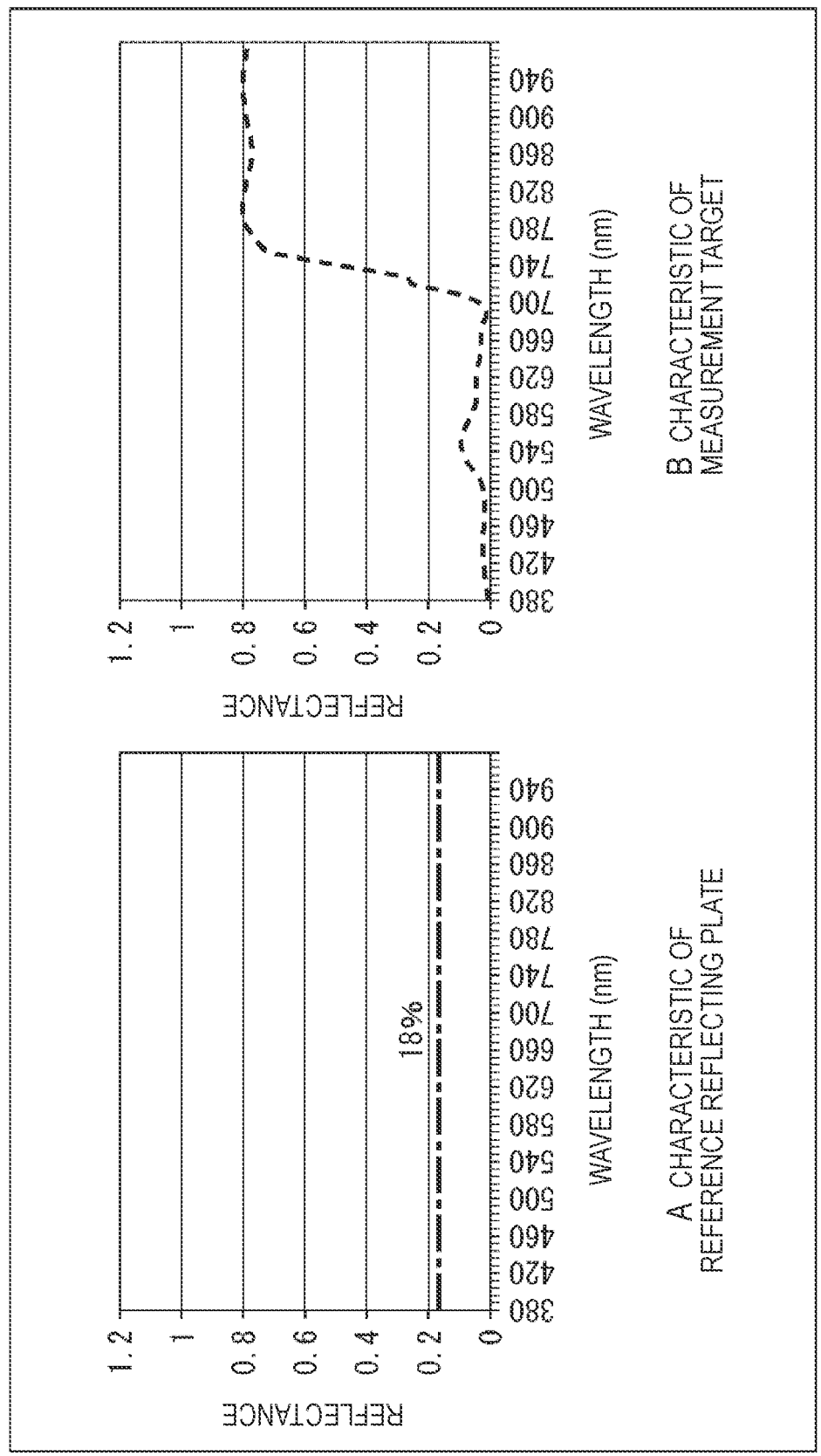
FIG. 12 is a diagram illustrating an example of characteristics of a reference reflecting plate and a measurement target.

Here, A of FIG. 12 illustrates an example of a characteristic of the reference reflecting plate 20 (FIG. 11) when the horizontal axis represents a wavelength (nm) and the vertical axis represents a reflectance. As illustrated in A of FIG. 12, the reflectance of the reference reflecting plate 20 is approximately 0.18 which is constant, and a spectral reflectance characteristic is flat.

B of FIG. 12 illustrates an example of a characteristic of the measurement target 1 (FIG. 11) when the horizontal axis represents a wavelength (nm) and the vertical axis represents a reflectance. As illustrated in B of FIG. 12, the reflectance of the measurement target 1 such as plants in a field has a value close to 0 up to around 700 nm, but increases in the vicinity of 700 nm and has a value close to approximately 0.8 (80%) in a range exceeding 700 nm.

In addition, the sensing device 101-1 outputs index measurement data for measuring a PPFD value of the reference reflecting plate 20, but RGB signals are required to calculate the PPFD value. For this reason, the sensing device 101-1 is provided with an RGB filter (hereinafter, referred to as an RGB filter 143-1) having characteristics illustrated in A of FIG. 13, as the filter 143-1. For example, as an arrangement pattern of the RGB filter 143-1, the arrangement pattern 143A illustrated in FIG. 7 can be used.

Figure 13:
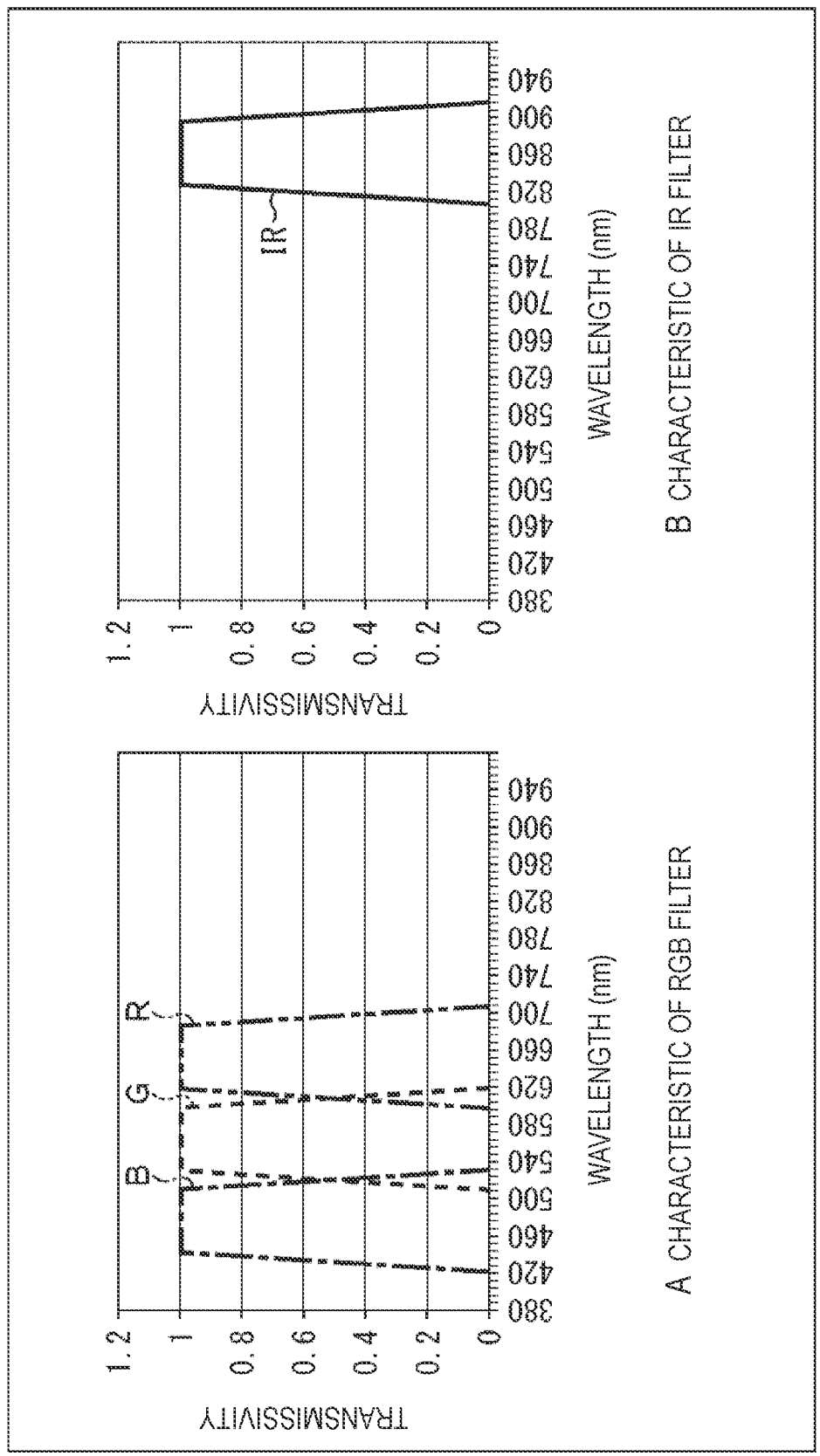
FIG. 13 is a diagram illustrating an example of characteristics of an RGB filter and an IR filter.

A of FIG. 13 illustrates an example of characteristics of the RGB filter 143-1 when the horizontal axis represents a wavelength (nm) and the vertical axis represents a transmissivity. As illustrated in A of FIG. 13, for example, the RGB filter 143-1 includes a B filter transmitting blue (B) light having a wavelength of 450 nm to 495 nm, a G filter transmitting green (G) light having a wavelength of 495 nm to 570 nm, and an R filter transmitting red (R) light having a wavelength of 620 nm to 750 nm.

On the other hand, the sensing device 101-2 outputs index measurement data for measuring an NDVI value of the measurement target 1 such as plants in a field, and not only an R signal but also an IR signal is required to calculate the NDVI value. For this reason, the sensing device 101-2 is provided with an IR filter (hereinafter, referred to as an IR filter 143-2) having characteristics illustrated in B of FIG. 13 as the filter 143-2. For example, as an arrangement pattern of the IR filter 143-2, the arrangement pattern 143B illustrated in FIG. 7 can be used.

B of FIG. 13 illustrates an example of characteristics of the IR filter 143-2 when the horizontal axis represents a wavelength (nm) and the vertical axis represents a transmissivity. As illustrated in B of FIG. 13, for example, the IR filter 143-2 transmits light in an infrared region (IR) having a wavelength of 800 nm to 940 nm.

(Flow of Signal Processing During Measurement of Sensing Device)

Next, reference will be made to FIG. 14 to describe a flow of a signal processed by the sensing device 101-1 and the sensing device 101-2 in a case in which the reference reflecting plate 20, the measurement target 1, the RGB filter 143-1, and the IR filter 143-2 have the characteristics illustrated in FIGS. 12 and 13.

Figure 14:
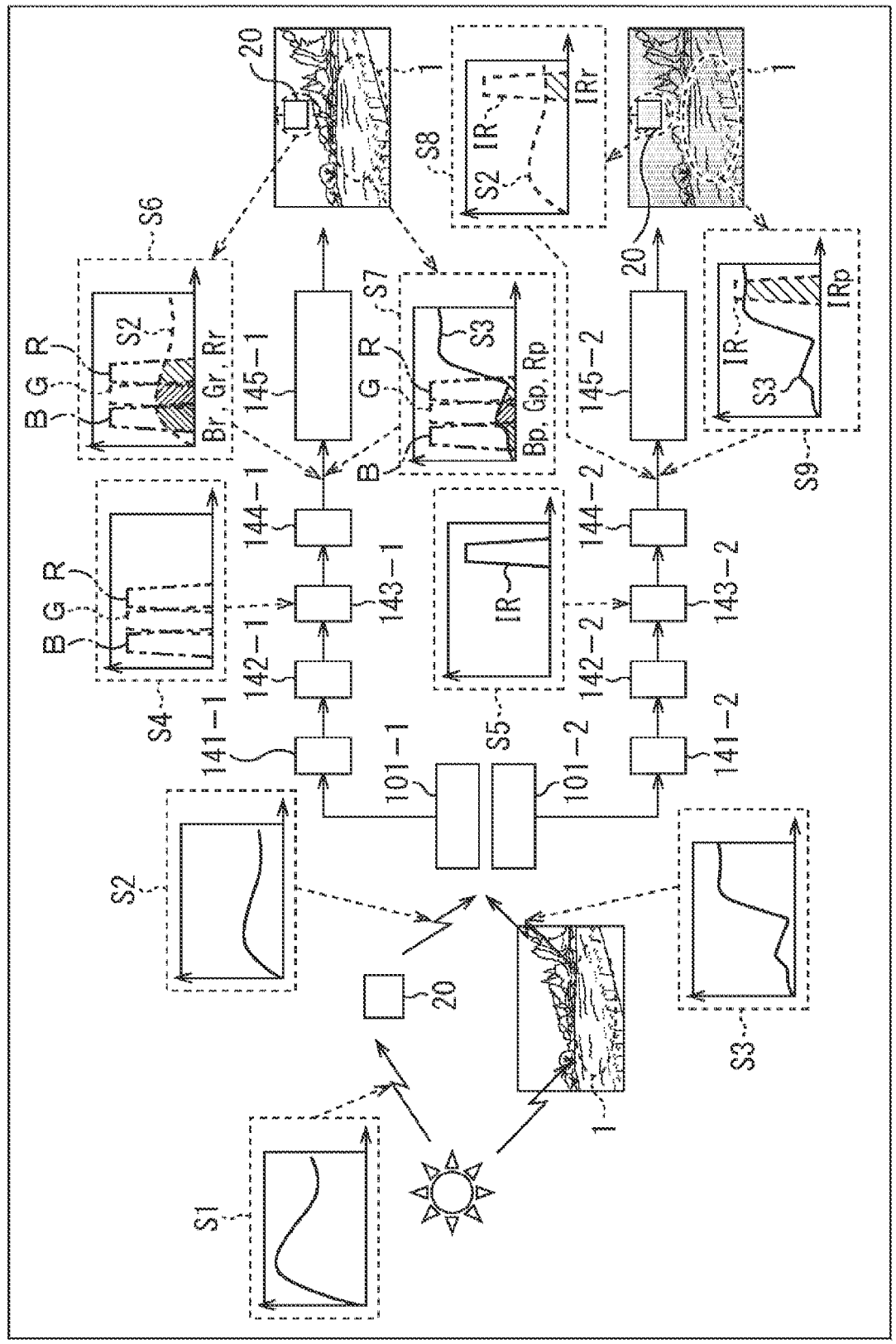
FIG. 14 is a diagram illustrating a flow of signal processing of the sensing device.

Note that, in FIG. 14, an upper sequence in the drawing shows a flow of a signal processed by the sensing device 101-1 having the RGB filter 143-1 attached thereto, and a lower sequence in the drawing shows a flow of a signal processed by the sensing device 101-2 having the IR filter 143-2 attached thereto, with respect to light reflected from the reference reflecting plate 20 or the measurement target 1.

In FIG. 14, sunlight (environment light) is reflected by the reference reflecting plate 20, and the reflected light is incident on the sensing device 101-1 and the sensing device 101-2. A spectral characteristic of the sunlight is indicated by a spectral characteristic S1. In addition, a spectral characteristic of the light reflected from the reference reflecting plate 20 is indicated by a spectral characteristic S2. That is, the reference reflecting plate 20 has the flat spectral characteristic illustrated in A of FIG. 12, and thus a reflection characteristic of the light reflected from the reference reflecting plate 20 is as indicated by the spectral characteristic S2.

In addition, sunlight is reflected by the measurement target 1 such as plants in a field, and the reflected light is incident on the sensing device 101-1 and the sensing device 101-2. A spectral characteristic of the light reflected from the measurement target 1 is indicated by a spectral characteristic S3. That is, the measurement target 1 has a reflection characteristic having a shape illustrated in B of FIG. 12, and thus a spectral characteristic of the light reflected from the measurement target 1 is as indicated by the spectral characteristic S3.

In the sensing device 101-1, light reflected by the reference reflecting plate 20 and the measurement target 1 is incident on the lens 141-1 and passes through the RGB filter 143-1, so that an image is formed on the sensor surface of the sensor 144-1.

In the sensing device 101-1, characteristics of the RGB filter 143-1 are represented by spectral characteristics S4. The spectral characteristics S4 correspond to transmission characteristics of the RGB filter illustrated in A of FIG. 13. In addition, as indicated by spectral characteristics S6 in which spectral characteristics S2 of reflected light of the reference reflecting plate 20 and the spectral characteristics S4 of the RGB filter 143-1 overlap each other, the sensor 144-1 outputs light received by the surface of the sensor as levels of Br, Gr, and Rr components. That is, signals according to the levels of Br, Gr, and Rr are RGB data (RGB signals) obtained by sensing the reference reflecting plate 20 by the sensing device 101-1.

In addition, as indicated by spectral characteristics S7 in which spectral characteristics S3 of reflected light of the measurement target 1 and the spectral characteristics S4 of the RGB filter 143-1 overlap each other, the sensor 144-1 outputs light received by the surface of the sensor as levels of Bp, Gp, and Rp components. That is, signals according to the levels of Bp, Gp, and Rp are RGB data (RGB signals) obtained by sensing the measurement target 1 (plants in a field) by the sensing device 101-1.

The signal processing unit 145-1 performs a process of rearranging data from the sensor 144-1, and the like and outputs data obtained as a result of the process through the I/F unit 146-1.

On the other hand, in the sensing device 101-2, the light reflected from the reference reflecting plate 20 and the measurement target 1 is incident on the lens 141-2 and passes through the IR filter 143-2, so that an image is formed on the sensor surface of the sensor 144-2.

In the sensing device 101-2, characteristics of the IR filter 143-2 are represented by spectral characteristics S5. The spectral characteristics S5 correspond to transmission characteristics of the IR filter illustrated in B of FIG. 13. In addition, as indicated by spectral characteristics S8 in which spectral characteristics S2 of reflected light of the reference reflecting plate 20 and the spectral characteristics S5 of the IR filter 143-2 overlap each other, the sensor 144-2 outputs light received by the surface of the sensor as a level of an IRr component. That is, signals according to the level of IRr are IR data (IR signals) obtained by sensing the reference reflecting plate 20 by the sensing device 101-2.

In addition, as indicated by spectral characteristics S9 in which spectral characteristics S3 of reflected light of the measurement target 1 and the spectral characteristics S5 of the IR filter 143-2 overlap each other, the sensor 144-2 outputs light received by the surface of the sensor as a level of an IRp component. That is, signals according to the level of IRp are IR data (IR signals) obtained by sensing the measurement target 1 (plants in a field) by the sensing device 101-2.

The signal processing unit 145-2 performs a process of rearranging data from the sensor 144-2, and the like and outputs data obtained as a result of the process through the I/F unit 146-2.

As described above, sensing is performed by the sensing device 101-1 and the sensing device 101-2, and thus RGB data (RGB signal) and IR data (IR signal) of a sensing image including the measurement target 1 and the reference reflecting plate 20 are acquired as index measurement data.

Note that, although an example in which two sensing devices 101-1 and two sensing devices 101-2 are provided has been described in FIGS. 11 to 14, but the number of sensing devices 101 is not limited to two.

For example, as described above, in the sensing device 101, a plurality of pixels two-dimensionally arranged in the pixel array portion of the sensor 144 have a pixel array corresponding to the arrangement pattern 143C (FIG. 7) as a color filter, so that it is possible to acquire an IR signal in addition to RGB signals. For this reason, in a case in which such a filter 143 is used, it is possible to configure one sensing device 101. However, a combination of an RGB filter and an IR cut filter is used as the filter 143 like the sensing device 101-1, and thus it is possible to adopt the same configuration as that of a general digital camera or a digital video camera which does not include a special optical filter.

(3) Photochemical System Reaction Maximum ETR Calculation Process
(Flow of Photochemical System Reaction Maximum ETR Calculation Process)

Next, details of the photochemical system reaction maximum ETR calculation process corresponding to step S102 of FIG. 10 will be described with reference to the flowchart of FIG. 15.

In step S121, the processing unit 162 of the effective index computation device 103 acquires RGB data obtained by sensing performed by the sensing device 101-1 (FIG. 11) and IR data obtained by sensing performed by the sensing device 101-2 (FIG. 11) as index measurement data. That is, here, image data of the RGB data and the IR data are taken in the processing unit 162.

In step S122, the calculation unit 171 of the effective index computation device 103 acquires a coefficient W1, a coefficient W2, and a coefficient W3 required to calculate a PPFD value with reference to the coefficient calculation LUT (LUT1) stored in the storage unit 163 on the basis of the RGB data acquired in the process of step S121.

Specifically, first, a Br signal, a Gr signal, and an Rr signal obtained from pixels corresponding to the region of the reference reflecting plate 20 in (a sensing image corresponding to) the RGB data are averaged to obtain a Br-ave signal, a Gr-ave signal, and an Rr-ave signal. Next, a ratio of the Br-ave signal to the Rr-ave signal or a ratio of the Br-ave signal to the Gr-ave signal is calculated on the basis of the Br-ave signal, the Gr-ave signal, and the Rr-ave signal obtained in the averaging process to obtain a Br-ave/Rr-ave value or a Br-ave/Gr-ave value.

Figure 16:
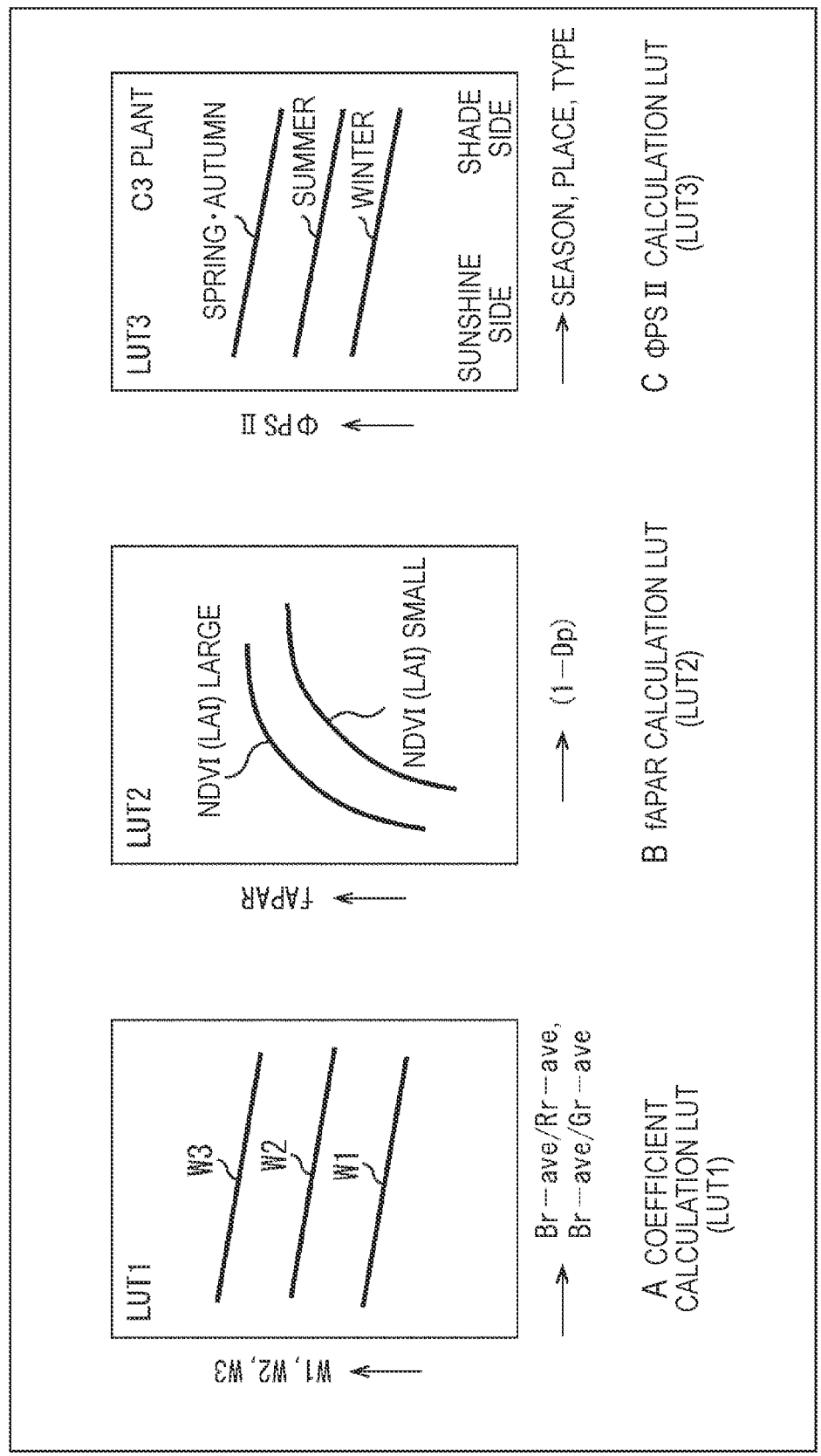
FIG. 16 is a diagram illustrating examples of a coefficient calculation LUT, a fAPAR calculation LUT, and a ΦPSII calculation LUT.

Here, an example of the coefficient calculation LUT (LUT1) is illustrated in A of FIG. 16. As illustrated in A of FIG. 16, a Br-ave/Rr-ave value or a Br-ave/Gr-ave value, a coefficient W1, a coefficient W2, and a coefficient W3 are associated with each other in the coefficient calculation LUT (LUT1). Therefore, it is possible to acquire the coefficient W1, the coefficient W2, and the coefficient W3 according to an inclination of spectral characteristics obtained from the Br-ave/Rr-ave value or the Br-ave/Gr-ave value from the coefficient calculation LUT (LUT1).

A relationship therebetween can be represented by the following Expression (2).

$$W1, W2, W3 = LUT1(Br\text{-}ave/Rr\text{-}ave, Br\text{-}ave/Gr\text{-}ave) \quad (2)$$

Note that a description has been given here of a case in which a ratio of the Br-ave signal to the Rr-ave signal or a ratio of the Br-ave signal to the Gr-ave signal is used when the coefficient calculation LUT (LUT1) is referred to, but a ratio of the Gr-ave signal to the Rr-ave signal, that is, a Gr-ave/Rr-ave value may be used.

Figure 15:
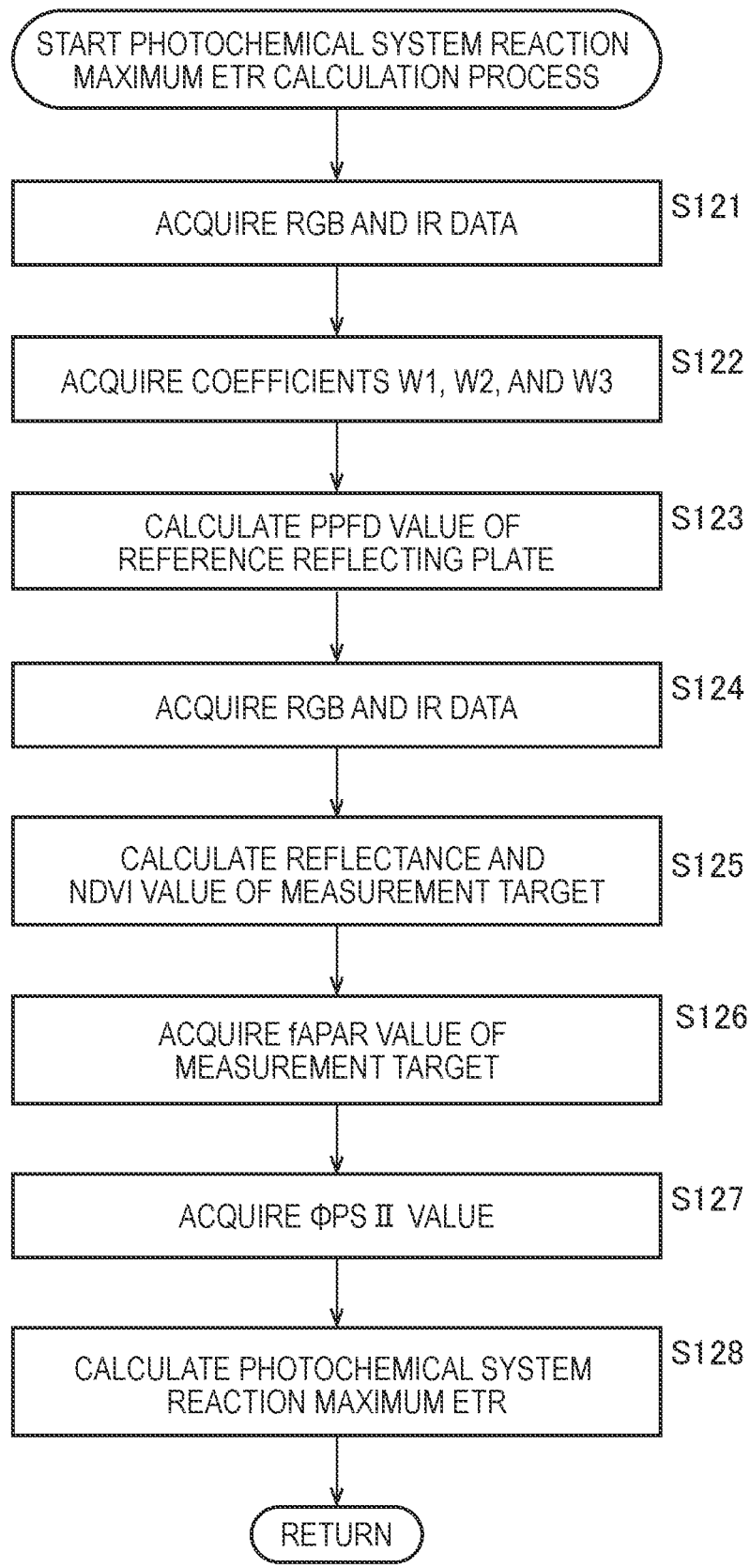
FIG. 15 is a flowchart illustrating a flow of a photochemical system reaction maximum ETR calculation process.

Referring back to the description of FIG. 15, in step S123, the calculation unit 171 of the effective index computation device 103 calculates a PPFD value of the reference reflecting plate 20 on the basis of the RGB data obtained in the process of step S121 and the coefficient W obtained in the process of step S122.

Here, as shown in the following Expression (3), it is possible to obtain a PPFD value of a B signal (PPFD (b)), a PPFD value of a G signal (PPFD (g)), and a PPFD value of an R signal (PPFD (r)) by respectively multiplying the Br-ave signal, the Gr-ave signal, and the Rr-ave signal by the coefficient W1, the coefficient W2, and the coefficient W3.

$$PPFD(b) = W1 \times Br\text{-}ave$$

$$PPFD(g) = W2 \times Gr\text{-}ave$$

$$PPFD(r) = W3 \times Rr\text{-}ave \quad (3)$$

The reason for the calculation of a PPFD value of the reference reflecting plate 20 in this manner is as follows. That is, the PPFD value does not change depending on the reflectance of the measurement target 1, and a PPFD value emitted to the reference reflecting plate 20 and a PPFD value emitted to the measurement target 1 are also the same value in the sunshine. Further, here, in contrast, on the premise of this, the PPFD value of the reference reflecting plate 20 is obtained by capturing reflected light of the reference reflecting plate 20 of which reflectance does not change. Note that details of a method of calculating the PPFD values calculated in the processes of steps S122 and S123 will be described later with reference to FIGS. 18 and 19.

In step S124, the processing unit 162 of the effective index computation device 103 acquires RGB data obtained by sensing performed by the sensing device 101-1 (FIG. 11) and IR data obtained by sensing performed by the sensing device 101-2 (FIG. 11) as index measurement data. That is, here, image data of the RGB data and the IR data are taken in the processing unit 162.

In step S125, the calculation unit 171 of the effective index computation device 103 calculates a reflectance and an NDVI value of the measurement target 1 on the basis of the RGB data and the IR data acquired in the process of step S124.

Here, it is assumed that the reflectance of the reference reflecting plate 20 is already known, that is, it is known that B, G, R, and IR components have the same reflectance of 18%. Consequently, it is possible to obtain the reflectance of the measurement target 1 by taking ratios of a Bp-ave signal, a Gp-ave signal, an Rp-ave signal, and an IRp-ave signal which are equivalent to reflected light of the measurement target 1 to a Br-ave signal, a Gr-ave signal, an Rr-ave signal, and an IRr-ave signal with respect to the value of the reflectance.

Note that the Bp-ave signal, the Gp-ave signal, the Rp-ave signal, and the IRp-ave signal are obtained by averaging a Bp signal, a Gp signal, an Rp signal, and an IRp signal which are obtained from pixels corresponding to the region of the measurement target 1 in (a sensing image corresponding to) RGB data. In addition, the Br-ave signal, the Gr-ave signal, the Rr-ave signal, and the IRr-ave signal are obtained by averaging a Br signal, a Gr signal, an Rr signal, and an IRr signal which are obtained from pixels corresponding to the region of the reference reflecting plate 20 in (the sensing image corresponding to) the RGB data.

That is, reflectances of B, G R, and IR components with respect to the measurement target 1 can be obtained by the following Expression (4).

$$Dp(b) = Dr(18\%) \times Bp\text{-}ave/Br\text{-}ave$$

$$Dp(g) = Dr(18\%) \times Gp\text{-}ave/Gr\text{-}ave$$

$$Dp(r) = Dr(18\%) \times Rp\text{-}ave/Rr\text{-}ave$$

$$Dp(ir) = Dr(18\%) \times IRp\text{-}ave/IRr\text{-}ave \quad (4)$$

In addition, an NDVI value can be obtained by the following Expression (5) by using the value obtained by Expression (4).

$$NDVI\ value = (Dp(ir) - Dp(r))/(Dp(ir) + Dp(r)) \quad (5)$$

Here, in Expression (5), Dp(ir) represents a reflectance of an infrared region, and Dp(r) represents a reflectance of red (R) in a visible region. The NDVI value (normalized difference vegetation index) is set to be an index indicating the distribution state and the degree of activity of plants in a field as the measurement target 1.

Here, the NDVI value is a vegetation index using an R component and an IR component as parameters, and only Dp(r) and Dp(ir), among reflectances obtained by Expression (4), are used in Expression (5). In addition, among the reflectances obtained by Expression (4), Dp(b) and Dp(g) are used when obtaining fractions of absorbed photosynthetically active radiation (fAPAR) of B, G and R components by Expression (8) to be described later, together with Dp(r).

Note that the Bp-ave signal and the like may be calculated from the entire region including plants to be measured in a sensing image (captured image) obtained by sensing or may be calculated for each small region by dividing the region into a plurality of small regions. The region is divided into small regions in this manner, and thus it is possible to generate a distribution diagram for each region of plants, for example, when displaying two-dimensional information illustrated in FIG. 28 to be described later.

However, as a premise for performing such processing, it is necessary to previously ascertain information regarding the region of the plants included in the sensing image (captured image) obtained by sensing. Here, for example, it is possible to obtain the information regarding the region of the plants by performing processing for recognizing the region of the plants on the sensing image. As the processing for recognizing the region of the plants, a known image recognition process can be used. In addition, a user may specify the region of the plants from the sensing image, instead of performing the image recognition process.

In step S126, the calculation unit 171 of the effective index computation device 103 acquires a fraction of absorbed photosynthetically active radiation (fAPAR) of the measurement target 1 with reference to the fAPAR calculation LUT (LUT2) stored in the storage unit 163 on the basis of the reflectance and the NDVI value of the measurement target 1 which are calculated in the process of step S125.

Here, light emitted to the plants (vegetation) is divided into reflected light, transmitted light, and absorbed light, and only the absorbed light among these light beams is utilized for photosynthesis. This can be represented by a relationship between a reflectance, a transmissivity, and an absorption rate of the plants as shown in the following Expression (6).

$$1=(\text{reflectance})+(\text{transmissivity})+(\text{absorption rate}) \tag{6}$$

In general, the reflectance and transmissivity of leaves of plants are substantially equal to each other, and the remaining light is absorbed. However, when a leaf area index (LAI) is approximately 2 or 3, leaves overlap each other, so that the reflection and absorption of transmitted light are repeated and approach the following Expression (7). Note that the leaf area index (LAI) represents a total value of a leaf area per unit surface area.

$$1=(\text{reflectance})+(\text{absorption rate}) \tag{7}$$

In addition, it is known that a change in the leaf area index (LAI) is related to a normalized difference vegetation index (NDVI). Consequently, as the fAPAR calculation LUT (LUT2), a look-up table is prepared in advance in which 1-Dp (reflectance) is taken as the horizontal axis and a fraction of absorbed photosynthetically active radiation (fAPAR) changes depending on the magnitude of an NDVI value.

B of FIG. 16 illustrates the fAPAR calculation LUT (LUT2). In the fAPAR calculation LUT (LUT2), a look-up table (LUT) in a case in which an NDVI value (leaf area index (LAI)) is large and a look-up table (LUT) in a case in which an NDVI value (leaf area index (LAI)) is small are prepared. Therefore, it is possible to acquire a fraction of absorbed photosynthetically active radiation (fAPAR) of the measurement target 1 from the fAPAR calculation LUT (LUT2) in accordance with the reflectance and the NDVI value of the measurement target 1.

A relationship therebetween can be represented as the following Expression (8) when fractions of absorbed photosynthetically active radiation (fAPAR) of B, G, and R components with respect to the measurement target 1 are set to be fAPAR(b), fAPAR(g), and fAPAR(r), respectively.

$$\text{fAPAR}(b)=LUT2(1-Dp(b))$$

$$\text{fAPAR}(g)=LUT2(1-Dp(g))$$

$$\text{fAPAR}(r)=LUT2(1-Dp(r)) \tag{8}$$

Note that, as described above, reference information for calculating the value of fAPAR is not limited to the fAPAR calculation LUT (LUT2), and for example, it is possible to directly obtain the value of fAPAR from an NDVI value by substituting a value for a function for calculating the value of fAPAR.

Figure 17:
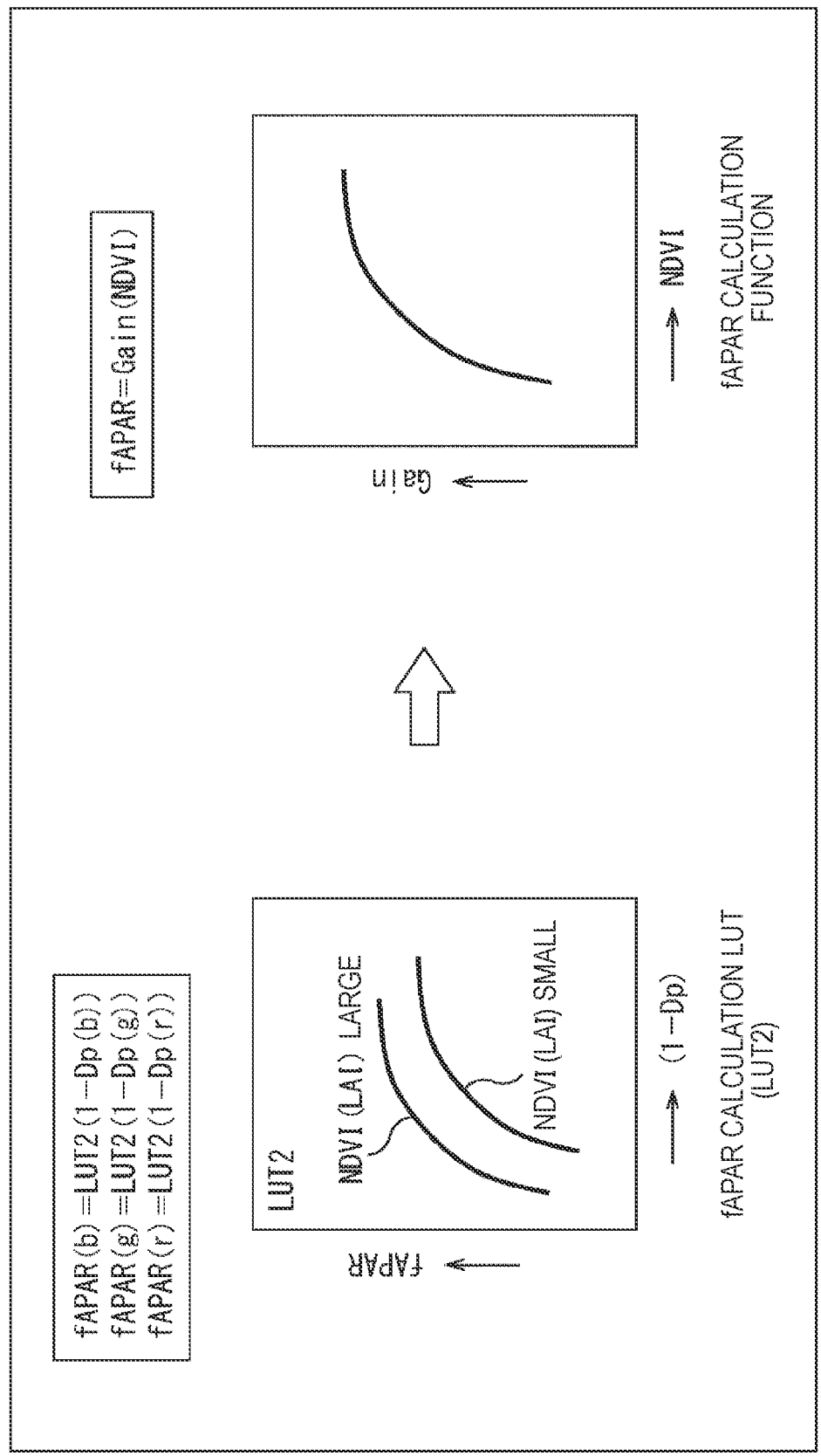
FIG. 17 is a diagram illustrating an example of a fAPAR calculation function.

FIG. 17 illustrates a fAPAR calculation function. In the fAPAR calculation function, it is possible to directly calculate the value of fAPAR from an NDVI value as shown in the following Expression (8A).

$$\text{fAPAR}=\text{Gain}(\text{NDVI}) \tag{8A}$$

However, in Expression (8A), a relationship of fAPAR (b)=fAPAR(g)=fAPAR(r) is established. Further, in Expression (8A), the value of Dp is not used, and there is a likelihood that accuracy is slightly decreased as compared to a case in which the value of Dp and an NDVI value are used as in the above-described fAPAR calculation LUT (LUT2), but it is possible to simplify processing for obtaining the value of fAPAR.

Referring back to the description of FIG. 15, in step S127, the calculation unit 171 of the effective index computation device 103 acquires a quantum yield (ΦPSII) of a photochemical system reaction in the measurement target 1 with reference to the ΦPSII calculation LUT (LUT3) stored in the storage unit 163.

Here, regarding the quantum yield (ΦPSII) of the photochemical system reaction, it is possible to observe the state by performing chlorophyll fluorescence measurement. That is, the quantum yield (efficiency) of the photochemical system reaction varies depending on a place where plants grow, the environment, the season, and the like. Consequently, chlorophyll fluorescence measurement is periodically performed on a target plant, and an LUT in which ΦPSII changes depending on a place, an environment, and the season is prepared in advance as the ΦPSII calculation LUT (LUT3).

C of FIG. 16 illustrates the ΦPSII calculation LUT (LUT3). In the ΦPSII calculation LUT (LUT3), a look-up table corresponding to each season such as spring, autumn, summer, and winter is prepared for a C3 plant, for example, for each place. Therefore, for example, in a case in which the measurement target 1 is the C3 plant, it is possible to acquire a quantum yield (ΦPSII) of a photochemical system reaction in the measurement target 1 from the ΦPSII calculation LUT (LUT3) in accordance with a measurement time, a measurement location, and the like.

A relationship therebetween can be represented as the following Expression (9).

$$\Phi PSII = LUT3(\text{season, place, type}) \quad (9)$$

Note that, the C3 plant is a plant which is classified according to what kind of organic matter carbon dioxide ($CO_2$) absorbed in photosynthesis is first synthesized in the plant body, and performs photosynthetic carbon assimilation by only a reductive pentose phosphate circuit. In addition, such classification also includes a C4 plant, a CAM plant, and the like in addition to the C3 plant. However, for example, in a case in which the measurement of the C4 plant is performed, it is necessary to prepare a ΦPSII calculation LUT (LUT3) for the C4 plant in advance.

For example, the C3 plant includes most plants such as rice and wheat. In addition, representative plants for the C4 plant include corn and sugarcane, and representative plants for the CAM plant include cactus. Note that grass is classified into a C3 plant or a C4 plant according to its type. For example, the bent grass is regarded as a C3 plant, and zoysiagrass and *Zoysia matrella* are regarded as a C4 plant.

In addition, for example, data corresponding to seasons and places is accumulated for each plant to be built as a database and a ΦPSII calculation LUT (LUT3) is created using the data accumulated in the database, so that it is possible to prepare a more optimum ΦPSII calculation LUT (LUT3). Here, parameters other than types of plants, season, and places may be included. In addition, machine learning may be performed on the data accumulated in the database.

Referring back to the description of FIG. 15, in step S128, the calculation unit 171 of the effective index computation device 103 calculates a photochemical system reaction maximum ETR in the measurement target 1 on the basis of the data obtained in the processes of steps S121 to S127.

Here, a method of calculating a photochemical system reaction maximum ETR will be described. First, in order to obtain the amount of photons (the amount of photons considered to have actually contributed to the growth of plants) which are effectively absorbed into the plants in the amount of photons emitted to the plants (PPFD value), the PPFD value obtained in the process of step S123 is multiplied by fAPAR obtained in the process of step S126.

Next, a value obtained by multiplying the PPFD value by the fAPAR is multiplied by a distribution rate to PSII m (generally regarded as 0.5) in the light emitted to the plants and the quantum yield (ΦPSII) of the photochemical system reaction which is obtained in the process of step S127. Thereby, a photochemical system reaction maximum ETR is calculated.

That is, when photochemical system reaction maximum ETRs of B, G, and R components with respect to the measurement target 1 are respectively set to be ETR1($b$), ETR1($g$), and ETR1($r$), the photochemical system reaction maximum ETRs are obtained by arithmetically operating the following Expression (10) and Expression (11) as ETR1.

$$ETR1(b) = PPFD(b) \times fAPAR(b) \times m \times \Phi PSII$$

$$ETR1(g) = PPFD(g) \times fAPAR(g) \times m \times \Phi PSII$$

$$ETR1(r) = PPFD(r) \times fAPAR(r) \times m \times \Phi PSII \quad (10)$$

$$ETR1 = ETR1(b) + ETR1(g) + ETR1(r) \quad (11)$$

Note that, in the field of plant physiology, ΦPSII often represents photochemical system reaction efficiency when generating an electron transport rate (ETR) flowing throughout plants, including even a carbon reduction reaction. That is, the photochemical system reaction efficiency also changes depending on the amount of electron transport rate (ETR) flowing through the carbon reduction reaction. On the other hand, in the present technology, photochemical system reaction efficiency when a photochemical system reaction is maximized is defined as ΦPSII from the amount of photons (PPFD value) which are emitted to and absorbed by plants.

When the process of step S128 is terminated, the processing returns to step S102 of FIG. 10, and the subsequent processes are executed.

A flow of the photochemical system reaction maximum ETR calculation process has been described above. In the photochemical system reaction maximum ETR calculation process, an electron transport rate (ETR) equivalent to energy output from a photochemical system reaction is calculated as a photochemical system reaction maximum ETR.

Note that, in the photochemical system reaction maximum ETR calculation process, a look-up table used to obtain an effective PPFD value may be switched for each region of each plant in a case in which a plurality of types of plants are present in a captured image obtained as a result of sensing. Thereby, even when a plurality of plants are shown in one screen, it is possible to present appropriate effective PPFD values at the same time.

(Details of Method of Calculating PPFD Value)

Here, details of a method of calculating the PPFD values calculated in the processes of steps S122 and S123 of FIG. 15 will be described with reference to FIGS. 18 to 19.

(Configuration of Processing Unit of Effective Index Computation Device)

Figure 18:
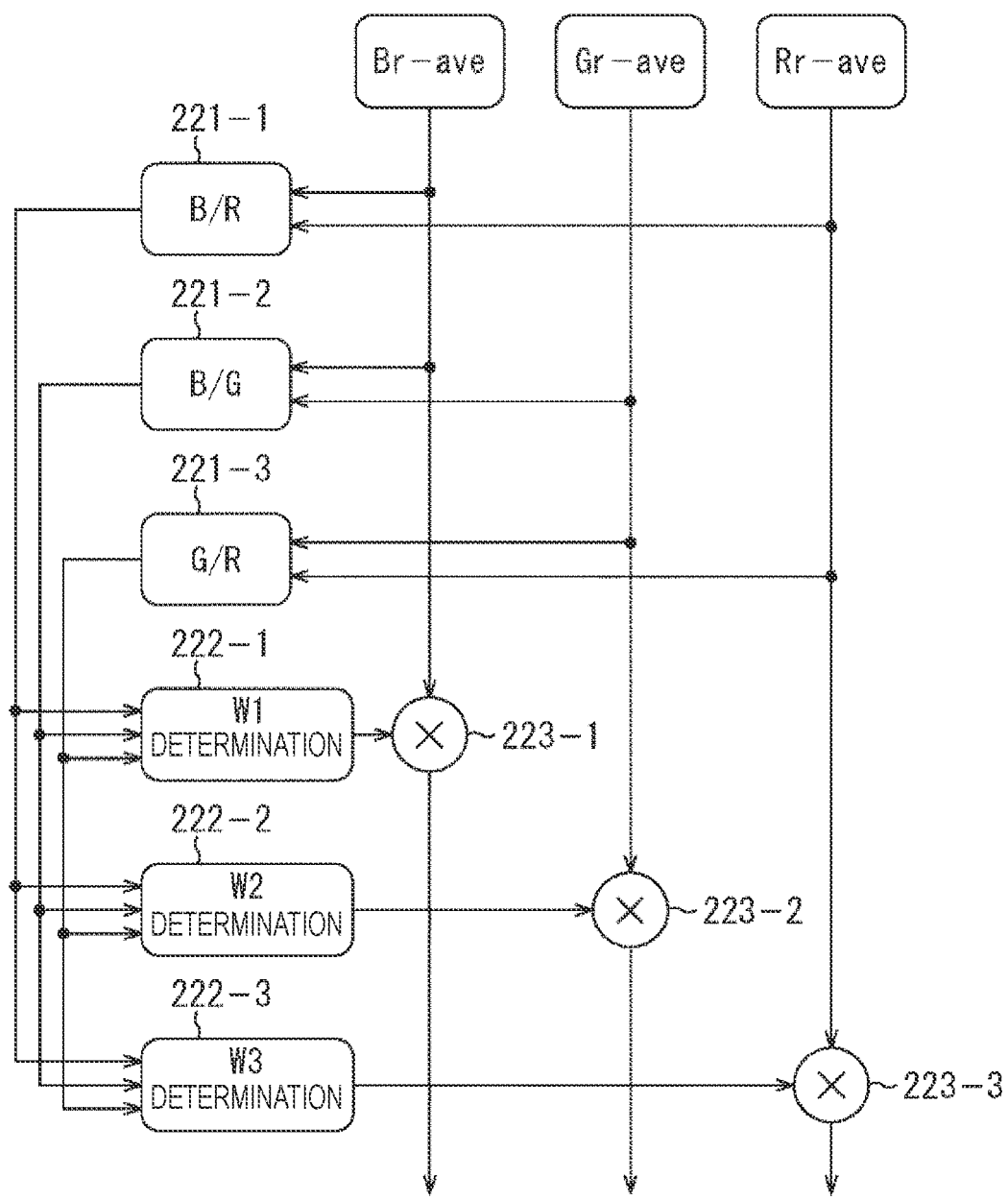
FIG. 18 is a diagram illustrating a detailed configuration example of a processing unit.

FIG. 18 is a diagram illustrating a detailed configuration example of (the calculation unit 171 of) the processing unit 162 of the effective index computation device 103 of FIG. 8.

In FIG. 18, the calculation unit 171 of the effective index computation device 103 includes a B/R value calculation unit 221-1, a B/G value calculation unit 221-2, a G/R value calculation unit 221-3, a W1 determination unit 222-1, a W2 determination unit 222-2, a W3 determination unit 222-3, a multiplier 223-1, a multiplier 223-2, and a multiplier 223-3 in order to calculate a PPFD value.

In the calculation unit 171, among a Br-ave signal, a Gr-ave signal, and an Rr-ave signal which are obtained from RGB data input from the sensing device 101-1, the Br-ave signal is input to the B/R value calculation unit 221-1, the B/G value calculation unit 221-2, and the multiplier 223-1. In addition, the Gr-ave signal is input to the B/G value calculation unit 221-2, the G/R value calculation unit 221-3, and the multiplier 223-2, and the Rr-ave signal is input to the B/R value calculation unit 221-1, the G/R value calculation unit 221-3, and the multiplier 223-3.

The B/R value calculation unit 221-1 divides the Br-ave signal input thereto by the Rr-ave signal, and a Br-ave/Rr-ave value obtained as a result of the division is output to each of the W1 determination unit 222-1 to the W3 determination unit 222-3.

The B/G value calculation unit 221-2 divides the Br-ave signal input thereto by the Gr-ave signal, and a Br-ave/Gr-ave value obtained as a result of the division is output to each of the W1 determination unit 222-1 to the W3 determination unit 222-3.

The G/R value calculation unit 221-3 divides the Gr-ave signal input thereto by the Rr-ave signal, and a Gr-ave/Rr-ave value obtained as a result of the division is output to each of the W1 determination unit 222-1 to the W3 determination unit 222-3.

The W1 determination unit 222-1 determines a coefficient W1 based on the Br-ave/Rr-ave value, the Br-ave/Gr-ave value, or the Gr-ave/Rr-ave value input thereto, and outputs the determined coefficient W1 to the multiplier 223-1. The multiplier 223-1 multiplies the Br-ave signal input thereto by the coefficient W1 output from the W1 determination unit 222-1.

The W2 determination unit 222-2 determines a coefficient W2 based on the Br-ave/Rr-ave value, the Br-ave/Gr-ave value, or the Gr-ave/Rr-ave value input thereto, and outputs the determined coefficient W1 to the multiplier 223-2. The multiplier 223-2 multiplies the Gr-ave signal input thereto by the coefficient W2 output from the W2 determination unit 222-2.

The W3 determination unit 222-3 determines a coefficient W3 based on the Br-ave/Rr-ave value, the Br-ave/Gr-ave value, or the Gr-ave/Rr-ave input thereto, and outputs the determined coefficient W1 to the multiplier 223-3. The multiplier 223-3 multiplies the Rr-ave signal input thereto by the coefficient W3 output from the W3 determination unit 222-3.

Here, the reason that the value of the B signal (Br-ave signal), the G signal (Gr-ave signal), and the R signal (Rr-ave signal) are respectively multiplied by the coefficient W1, the coefficient W2, and the coefficient W3 will be described. FIG. 19 illustrates a relationship between PPFD values and values of color components of RGB. A of FIG. 19 illustrates spectral characteristics of sunlight outdoors when the vertical axis represents a spectral radiation luminance (W/sr·m$^2$/nm) and the horizontal axis represents a wavelength (nm). In addition, B of FIG. 19 illustrates RGB signals output from a sensor including a color filter having the arrangement pattern 143A of FIG. 7 when the vertical axis represents a signal level of each of the RGB signals and the horizontal axis represents a wavelength (nm).

Figure 19:
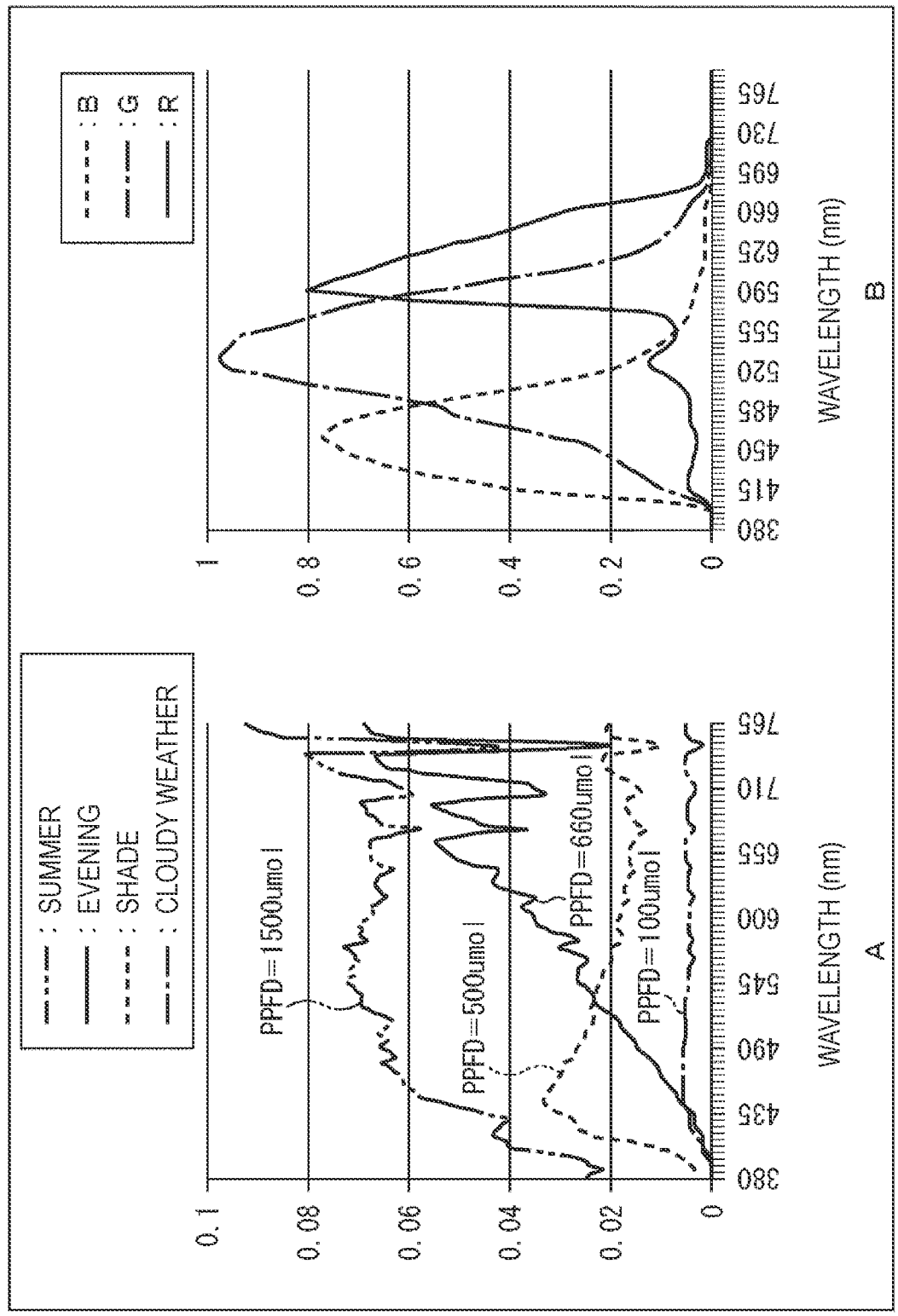
FIG. 19 is a diagram illustrating a relationship between PPFD values and values of color components of RGB.

In A of FIG. 19, as spectral characteristics of sunlight in summer, sunlight in the evening, sunlight in the shade, and sunlight in cloudy weather are shown as spectral characteristics of sunlight according to conditions such as time, season, and weather. In this case, a PPFD value can be obtained as an integral value of a value obtained by multiplying a level of each wavelength of sunlight by each wavelength. That is, the PPFD value is calculated by the following Expression (12).

[Math. 1]

$$PPFD = C1 \times \Sigma_{\lambda=400\,nm}^{700\,nm}(A \times \lambda(nm)) \quad (12)$$

Note that, in Expression (12), A represents a spectral radiation luminance (W/sr·m$^2$/nm), and λ(nm) represents a wavelength. In addition, λ=400 nm to 700 nm corresponds to an absorption wavelength of chlorophyll of a photosynthetic photon flux density (PPFD). Further, C1 is a coefficient.

In A of FIG. 19, 1500 umol is calculated as a PPFD value of sunlight in summer, 660 umol is calculated as a PPFD value of sunlight in the evening, 500 umol is calculated as a PPFD value of sunlight in the shade, and 100 umol is calculated as a PPFD value of sunlight in cloudy weather. In this manner, a PPFD value varies greatly depending on spectral characteristics of sunlight, specifically, an inclination of a graph in a case in which the horizontal axis represents a wavelength, the vertical axis represents a spectral radiation luminance, and the spectral radiation luminance is normalized in a range of 0 to 1.

Here, as illustrated in B of FIG. 19, in the arrangement pattern 143A of FIG. 7, a value obtained by integrating signals in wavelength bands corresponding to B, G, and R pixels of incident light is output from a sensor. Here, in order to obtain a PPFD value from RGB signals, a coefficient W1, a coefficient W2, and a coefficient W3 may be controlled so that results obtained by multiplying each of the values of the B signal, the G signal, and the R signal by the coefficient W1, the coefficient W2, and the coefficient W3 are equal to a value to be obtained as a PPFD value.

Here, in the sensing device 101-1, the filter 143-1 is constituted by an RGB filter (RGB filter 143-1) and an IR cut filter, and an output from the sensor 144-1 is set to be RGB signals.

For this reason, also in the calculation unit 171 of the effective index computation device 103 processing RGB data output from the sensing device 101-1, a coefficient W1, a coefficient W2, and a coefficient W3 may be controlled so that results obtained by multiplying each of the values of the B signal (Br-ave signal), the G signal (Gr-ave signal), and the R signal (Rr-ave signal) by the coefficient W1, the coefficient W2, and the coefficient W3 are equal to a value to be obtained as a PPFD value.

That is, in the calculation unit 171 of the effective index computation device 103, it can be said that the coefficient W1, the coefficient W2, and the coefficient W3 may be controlled so as to satisfy a relationship of the following Expression (13).

$$PPFD = C2 \times (W1 \times B + W2 \times G + W3 \times R) \quad (13)$$

Note that, in Expression (13), B, G and R respectively represent values of the B signal (Br-ave signal), the G signal (Gr-ave signal), and the R signal (Rr-ave signal), and W1, W2, and W3 respectively represent the coefficient W1, the coefficient W2, and the coefficient W3. In addition, C2 is a coefficient.

Here, in the calculation unit 171 of FIG. 18, the W1 determination unit 222-1 determines a coefficient W1 corresponding to a Br-ave/Rr-ave value, a Br-ave/Gr-ave value, or a Gr-ave/Rr-ave value. Similarly, the W2 determination unit 222-2 determines a coefficient W2 corresponding to a Br-ave/Rr-ave value, a Br-ave/Gr-ave value, or a Gr-ave/Rr-ave value, and the W3 determination unit 222-3 determines a coefficient W3 corresponding to a Br-ave/Rr-ave value, a Br-ave/Gr-ave value, or a Gr-ave/Rr-ave value.

That is, in the W1 determination unit 222-1 to the W3 determination unit 222-3, a ratio of the Br-ave signal to the Rr-ave signal, a ratio of the Br-ave signal to the Gr-ave signal, or a ratio of the Gr-ave signal to the Rr-ave signal is calculated from the values of the Br-ave signal, the Gr-ave signal, and the Rr-ave signal obtained from the RGB data output from the sensing device 101-1, so that it is possible to obtain (a value equivalent to) an inclination of spectral characteristics of sunlight from the value (the Br-ave/Rr-ave value, the Br-ave/Gr-ave value, or the Gr-ave/Rr-ave value) of the ratio.

Further, in the effective index computation device 103, a coefficient calculation LUT (LUT1) in which an inclination of spectral characteristics of sunlight (an inclination of spectral characteristics obtained from the Br-ave/Rr-ave value, the Br-ave/Gr-ave value, or the Gr-ave/Rr-ave value) is associated with a coefficient W1, a coefficient W2, and a coefficient W3 is stored in the storage unit 163. Thereby, in the W1 determination unit 222-1 to the W3 determination unit 222-3 of the calculation unit 171, it is possible to determine a coefficient W1 to a coefficient W3 corresponding to an inclination of spectral characteristics obtained from the Br-ave/Rr-ave value, the Br-ave/Gr-ave value, or the Gr-ave/Rr-ave value from the coefficient calculation LUT (LUT1).

That is, in the W1 determination unit 222-1, the coefficient W1 corresponding to an inclination of spectral characteristics obtained from the Br-ave/Rr-ave value or the like is determined by referring to the coefficient calculation LUT (LUT1). As a result, in the multiplier 223-1, the Br-ave signal is multiplied by the coefficient W1 determined by the W1 determination unit 222-1, so that a PPFD value (W1× Br-ave) of the B signal is obtained.

In addition, in the W2 determination unit 222-2, the coefficient W2 corresponding to an inclination of spectral characteristics obtained from the Br-ave/Rr-ave value or the like is determined by referring to the coefficient calculation LUT (LUT1). As a result, in the multiplier 223-2, the Gr-ave signal is multiplied by the coefficient W2 determined by the W2 determination unit 222-2, so that a PPFD value (W2× Gr-ave) of the G signal is obtained.

In addition, in the W3 determination unit 222-3, the coefficient W3 corresponding to an inclination of spectral characteristics obtained from the Br-ave/Rr-ave value or the like is determined by referring to the coefficient calculation LUT (LUT1). As a result, in the multiplier 223-3, the Rr-ave signal is multiplied by the coefficient W3 determined by the W3 determination unit 222-3, so that a PPFD value (W3× Rr-ave) of the R signal is obtained.

Further, in the calculation unit 171, an output (W×Br-ave) from the multiplier 223-1, an output (W2×Gr-ave) from the multiplier 223-2, and an output (W3×Rr-ave) from the multiplier 223-3 are added up in accordance with the above-described Expression (13), so that a PPFD value (W1×Br-ave+W2×Gr-ave+W3×Rr-ave) is calculated.

Details of a method of calculating a PPFD value have been described above.

Note that, here, an example of a case in which a reference reflecting plate, such as a gray reflecting plate, which has flat spectral reflection characteristics is used has been described. However, in a case in which a region having non-flat spectral reflection characteristics (for example, an en-tout-cas in a stadium, or the like) is used as a reference reflecting plate (reference reflecting region), RGB data output from the sensing device 101-1 is different from that in a case in which a gray reflecting plate or the like is used, due to the influence of reflection of the reference reflecting region. However, also in this case, a coefficient calculation LUT (LUT1) corresponding to a reference reflecting region, such as an en-tout-cas, which has non-flat spectral reflection characteristics is prepared in advance, so that it is possible to obtain the same result as a PPFD value in a case in which a reference reflecting plate, such as a gray reflecting plate, which has flat spectral reflection characteristics is used, by using the coefficient calculation LUT (LUT1) when the PPFD value is calculated.

(4) Carbon Reduction Reaction Maximum ETR Calculation Process

A carbon reduction reaction is a reaction going through three reaction processes within a Calvin cycle (Calvin circuit). A first reaction process is a carboxylation reaction for connecting carbon dioxide ($CO_2$) to a carbon skeleton of a $CO_2$ receptor. A second reaction process is a reduction reaction for generating carbohydrate (sugar or starch) using photochemically produced nicotinamide adenine dinucleotide phosphate (NADPH), energy of adenosine triphosphate (ATP), and reducing power. A third reaction process is a reproduction reaction for generating ribulose-1,5-diphosphate which is a $CO_2$ receptor.

Reaction rates of these reactions greatly differ depending on a $CO_2$ concentration, a temperature, a humidity, and the type of plant. Note that characteristics of plants include not only, for example, classification of a C3 plant, a C4 plant and a CAM plant but also characteristics different depending on types of plants. It is difficult to comprehensively ascertain these elements, but it is possible to fix the type of plant and to measure the state of a change within a more limited environment.

As such a type of measurement method, a gas exchange measurement method is generally used, and it is possible to measure a photosynthesis rate of a carbon reduction reaction by capturing a change in $CO_2$ concentration while controlling light, a $CO_2$ concentration, a temperature, and a humidity. In addition, it is possible to create a $CO_2$ rate limiting photosynthesis rate LUT (LUT4), a temperature correction coefficient LUT (LUT5), and a humidity correction coefficient LUT (LUT6) by using the measurement method.

For example, a photosynthesis rate (ETR) of a carbon reduction reaction (which is not rate-limited to a photochemical system reaction) depending on a $CO_2$ concentration is measured at a certain temperature and humidity for each of the type of plant, season, and a place, and thus it is possible to create the $CO_2$ rate limiting photosynthesis rate LUT (LUT4) in which a $CO_2$ concentration and a photosynthesis rate are associated with each other. Similarly, in a case in which a temperature and a humidity are changed for each of the type of plant, season, and a place, and the amounts of change thereof are respectively set to be a correction coefficient T and a correction coefficient F, and thus it is possible to create the temperature correction coefficient LUT (LUT5) in which a temperature and a correction coefficient T are associated with each other and the humidity correction coefficient LUT (LUT6) in which a humidity and a correction coefficient F are associated with each other.

(Flow of Carbon Reduction Reaction Maximum ETR Calculation Process)

Here, details of a carbon reduction reaction maximum ETR calculation process corresponding to step S103 of FIG. 10 will be described with reference to a flowchart of FIG. 20.

In step S141, the processing unit 162 of the effective index computation device 103 acquires data of a $CO_2$ concentration, a temperature, and a humidity as environment measurement data obtained by sensing performed by the environment sensor 102 (FIG. 6).

In step S142, the calculation unit 171 of the effective index computation device 103 acquires a photosynthesis rate limited to the $CO_2$ concentration obtained in the process of step S141 with reference to the $CO_2$ rate limiting photosynthesis rate LUT (LUT4) stored in the storage unit 163.

Figure 21:
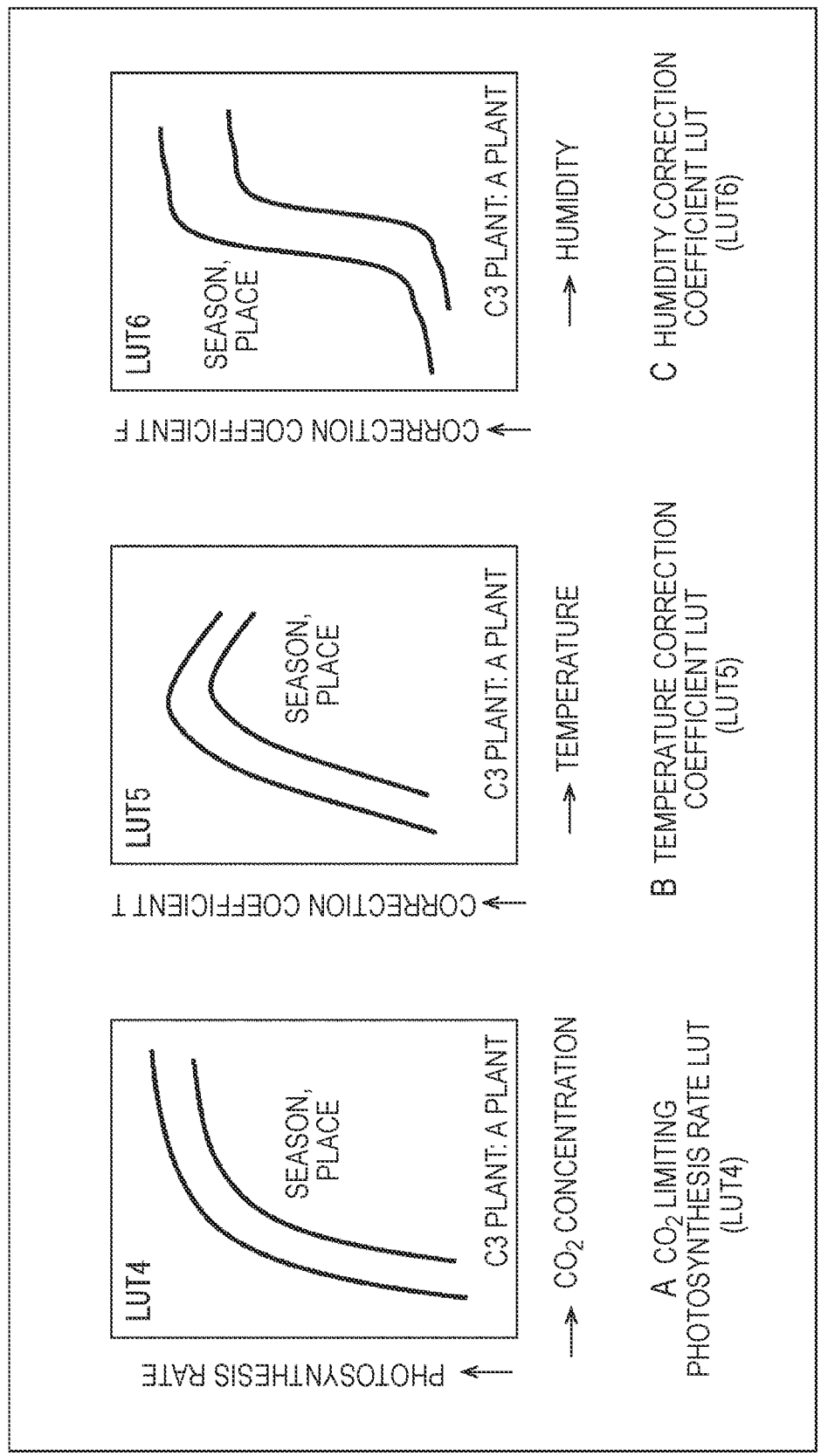
FIG. 21 is a diagram illustrating examples of a $CO_2$ rate limiting synthesis LUT, a temperature correction coefficient LUT, and a humidity correction coefficient LUT.

A of FIG. 21 illustrates the $CO_2$ rate limiting photosynthesis rate LUT (LUT4). In the $CO_2$ rate limiting photosynthesis rate LUT (LUT4), a plurality of look-up tables in which a $CO_2$ concentration and a photosynthesis rate are associated with each other are prepared for an A plant which is a C3 plant, for example, for each season and each place. Therefore, for example, in a case in which the measurement target 1 is the A plant which is a C3 plant, it is possible to acquire a photosynthesis rate (ETR) limited to a measured $CO_2$ concentration from the $CO_2$ rate limiting photosynthesis rate LUT (LUT4) in accordance with a measurement time, a measurement location, and the like.

A relationship therebetween can be represented as the following Expression (14).

$$ETR@CO_2 = LUT4(CO_2 \text{concentration}) \qquad (14)$$

Figure 20:
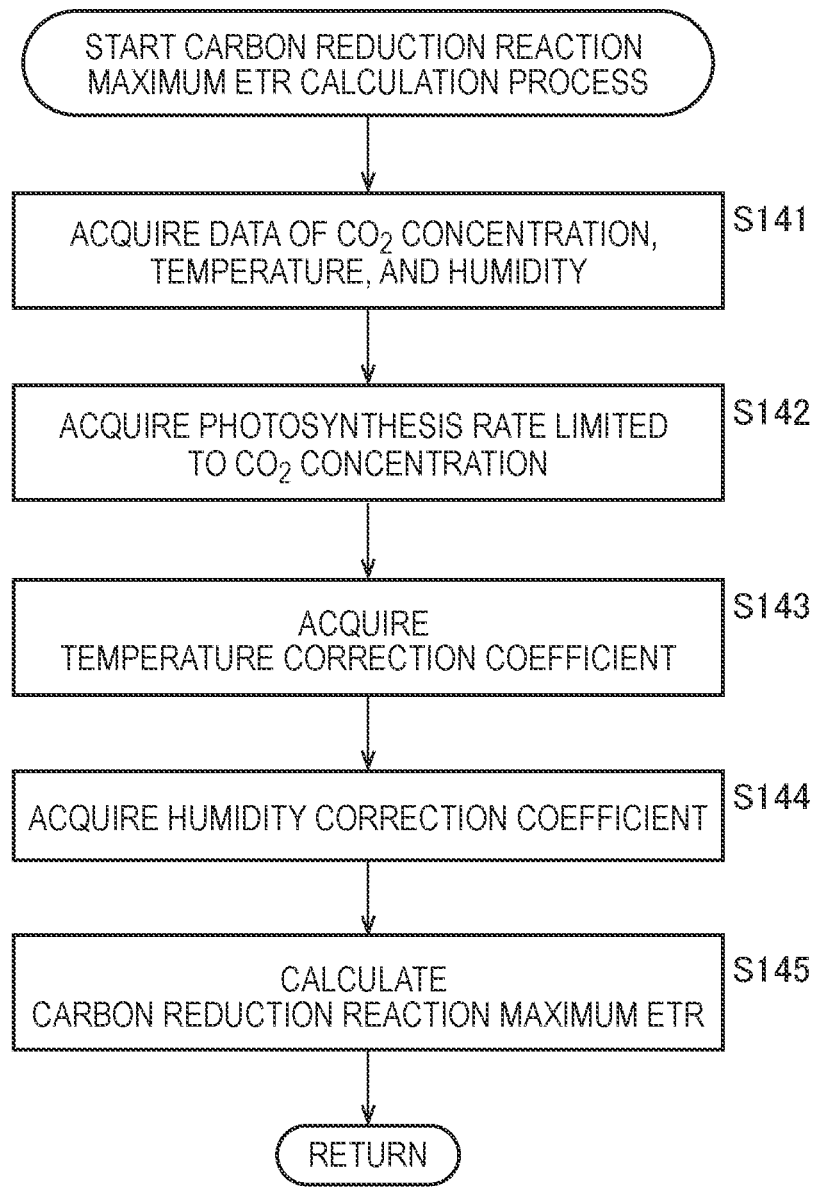
FIG. 20 is a flowchart illustrating a flow of a carbon reduction reaction maximum ETR calculation process.

Referring back to the description of FIG. 20, in step S143, the calculation unit 171 of the effective index computation device 103 acquires a correction coefficient T corresponding to the temperature obtained in the process of step S141 with reference to the temperature correction coefficient LUT (LUT5) stored in the storage unit 163.

B of FIG. 21 illustrates the temperature correction coefficient LUT (LUT5). In the temperature correction coefficient LUT (LUT5), a plurality of look-up tables in which a temperature and a correction coefficient T are associated with each other are prepared for the A plant which is a C3 plant, for example, for each season and each place. Therefore, for example, in a case in which the measurement target 1 is the A plant which is a C3 plant, it is possible to acquire a correction coefficient T corresponding to a measured temperature from the temperature correction coefficient LUT (LUT5) in accordance with a measurement time and a measurement location.

A relationship therebetween can be represented as the following Expression (15).

$$T = LUT5(\text{temperature}) \qquad (15)$$

Referring back to the description of FIG. 20, in step S144, the calculation unit 171 of the effective index computation device 103 acquires a correction coefficient F corresponding to the humidity obtained in the process of step S141 with reference to the humidity correction coefficient LUT (LUT6) stored in the storage unit 163.

C of FIG. 21 illustrates the humidity correction coefficient LUT (LUT6). In the humidity correction coefficient LUT (LUT6), a plurality of look-up tables in which a humidity and a correction coefficient F are associated with each other are prepared for the A plant which is a C3 plant, for example, for each season and each place. Therefore, for example, in a case in which the measurement target 1 is the A plant which is a C3 plant, it is possible to acquire a correction coefficient F corresponding to a measured humidity from the humidity correction coefficient LUT (LUT6) in accordance with a measurement time and a measurement location.

A relationship therebetween can be represented as the following Expression (16).

$$F = LUT6(\text{temperature}) \qquad (16)$$

Referring back to the description of FIG. 20, in step S145, the calculation unit 171 of the effective index computation device 103 calculates a carbon reduction reaction maximum ETR in the measurement target 1 on the basis of the data obtained in the processes of steps S141 to S144.

Here, a method of calculating an carbon reduction reaction maximum ETR will be described. The carbon reduction reaction maximum ETR is obtained by multiplying a photosynthesis rate (ETR) limited to a $CO_2$ concentration by a correction coefficient T of a temperature and a correction coefficient F of a humidity. That is, when the carbon reduction reaction maximum ETR is set to be ETR2, ETR2 is obtained by arithmetically operating the following Expression (17).

$$ETR2 = ETR@CO_2 \times T \times F \qquad (17)$$

When the process of step S1145 is terminated, the processing returns to step S103 of FIG. 10, and the subsequent processes are executed.

A flow of the carbon reduction reaction maximum ETR calculation process has been described above. In the carbon reduction reaction maximum ETR calculation process, an electron transport rate (ETR) equivalent to a maximum photosynthesis rate of a carbon reduction reaction determined from an environment or the type of plant is calculated as a carbon reduction reaction maximum ETR.

Note that, in the carbon reduction reaction maximum ETR calculation process, in a case in which a plurality of types of plants are present in a captured image obtained as a result of sensing, similar to the photochemical system reaction maximum ETR calculation process, it is possible to switch a look-up table used to obtain an effective PPFD value for each region of each plant. Thereby, even when a plurality of plants are shown within one screen, it is possible to present appropriate effective PPFD values at the same time.

(5) Example of Presentation of Effective PPFD Value and the Like

Next, an example of presentation of presentation information including information regarding the effective PPFD value displayed in the process of step S106 of FIG. 10 will be described with reference to FIGS. 22 to 28.

The inventor of the present technology performed simulation under the following environments of (a) to (d) in order to confirm how a PPFD value of the measurement target 1 such as plants in a field and an effective PPFD value thereof change due to a difference in environment on a certain actual day.

(a) Environment A: sunshine, an average temperature of 15 degrees for a day (b) Environment B: shade, an average temperature of 15 degrees for a day (c) Environment C: sunshine, an average temperature of 3 degrees for a day (d) Environment D: shade, an average temperature of 3 degrees for a day Hereinafter, an example of presentation (an example of display) of presentation information corresponding to data obtained as results of simulations performed under the environments A to D will be described. Here, it is assumed that the measurement target 1 is plants.

(5-1) Example of Display of Environment a (Sunshine, Average Temperature of 15 Degrees)

Figure 22:
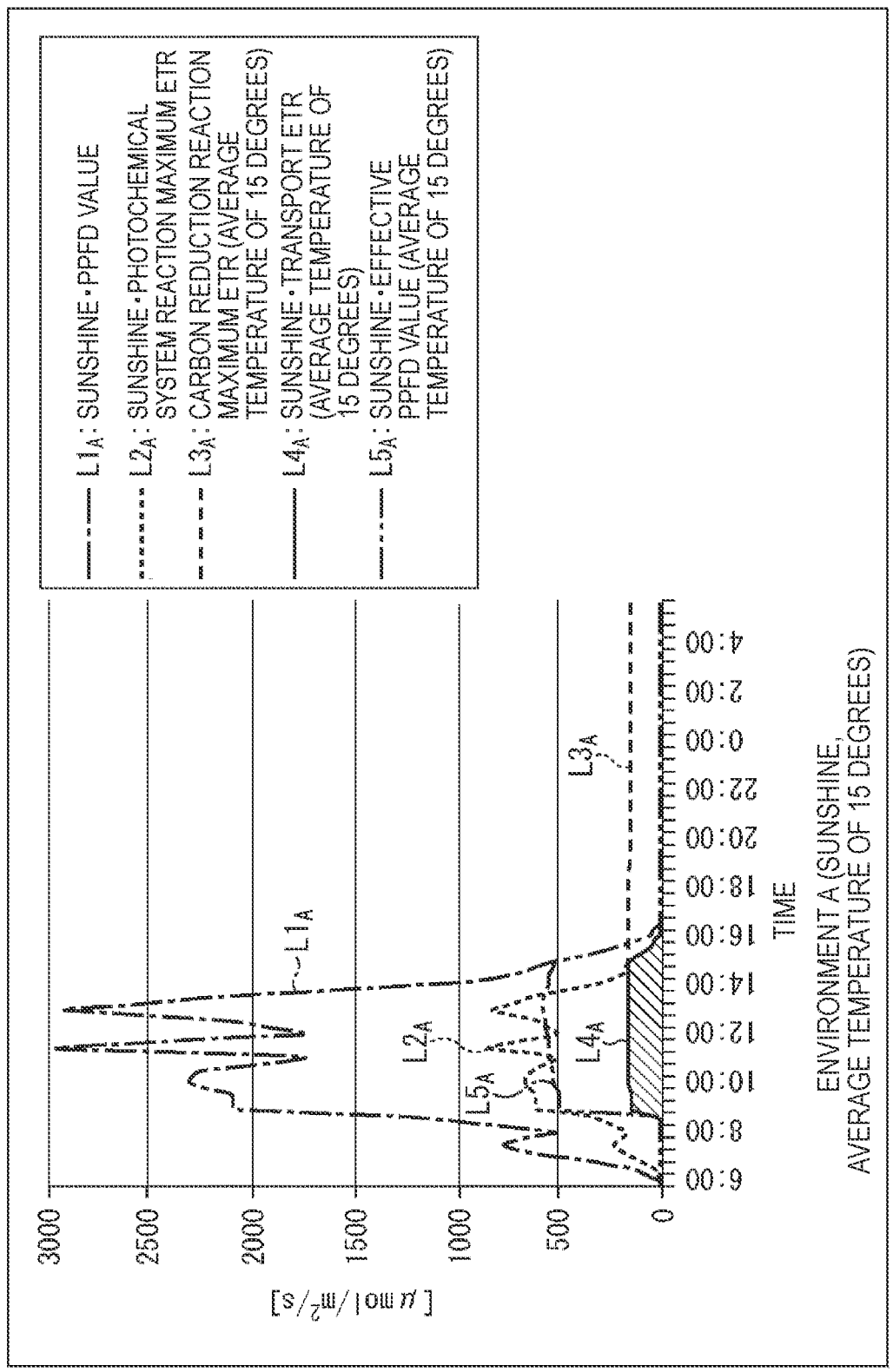
FIG. 22 is a diagram illustrating an example of display of PPFD values, effective PPFD values, and the like in an environment A.

FIG. 22 is a diagram illustrating an example of display of PPFD values, effective PPFD values, and the like in the environment A.

In FIG. 22, the horizontal axis represents a time, and 24 hours from 6:00 in the morning on a certain day to 6:00 on the next day are graduated in units of 30 minutes. The vertical axis represents a value of data obtained as a result of simulation performed in the environment A which is indicated by lines L1 to L5 which are different types of lines, and the unit is umol/m²/s. Note that a relationship between these axes is the same as those in FIGS. 23 to 25 to be described later.

In the environment A, plants are present in the sunshine, and an average temperature in the vicinity of the plants for a day is 15 degrees. As a result of simulation performed under such an environment, a line $L1_A$ indicates changes in a PPFD value (sunshine·PPFD value) of sunlight emitted to a sunshine portion of the plants. A line $L2_A$ indicates changes in a photochemical system reaction maximum ETR (sunshine-photochemical system reaction maximum ETR) when sunlight emitted to a sunshine portion of the plants is converted into energy by a photochemical system reaction of the plants.

A line $L3_A$ indicates changes in a carbon reduction reaction maximum ETR (carbon reduction reaction maximum ETR (an average temperature of 15 degrees)) of the plants which is determined in accordance with an environment such as an average temperature of 15 degrees. A line $L4_A$ indicates changes in a transport ETR (sunshine-transport ETR (an average temperature of 15 degrees)) in the environment A. That is, the sunshine-photochemical system reaction maximum ETR indicated by the line $L2_A$ and the carbon reduction reaction maximum ETR (an average temperature of 15 degrees) indicated by the line $L3_A$ are compared with each other, and a smaller value is determined to be a bottleneck, thereby determining a transport ETR of transport inside the plants.

Here, the value of the carbon reduction reaction maximum ETR (an average temperature of 15 degrees) is smaller than the value of the sunshine-photochemical system reaction maximum ETR, and thus the carbon reduction reaction maximum ETR (an average temperature of 15 degrees) is determined to be a bottleneck and is set to be a sunshine-transport ETR (an average temperature of 15 degrees). As a result, in FIG. 22, the line $L4_A$ overlaps a portion of the line $L3_A$.

In addition, the line $L4_A$, which is a sunshine-transport ETR (an average temperature of 15 degrees), indicates a value having actually contributed to the growth of the plants, and an area of a portion (a portion indicated by an oblique line of FIG. 22) on the inner side of the line $L4_A$ is proportional to the amount of growth of the plants. Note that, strictly speaking, the growth of the plants is also affected by a mechanism of the commutation of sugar such as a light compensation point and a light saturation point.

A line $L5_A$ indicates changes in an effective PPFD value (sunshine-effective PPFD value (an average temperature of 15 degrees)) in the environment A. The sunshine-effective PPFD value (an average temperature of 15 degrees) indicated by the line $L5_A$ is obtained by converting the value of the sunshine-transport ETR (an average temperature of 15 degrees) indicated by the line $L4_A$ into the amount of emission of sunlight emitted to a sunshine portion of the plants.

(5-2) Example of Display of Environment B (Shade, Average Temperature of 15 Degrees)

Figure 23:
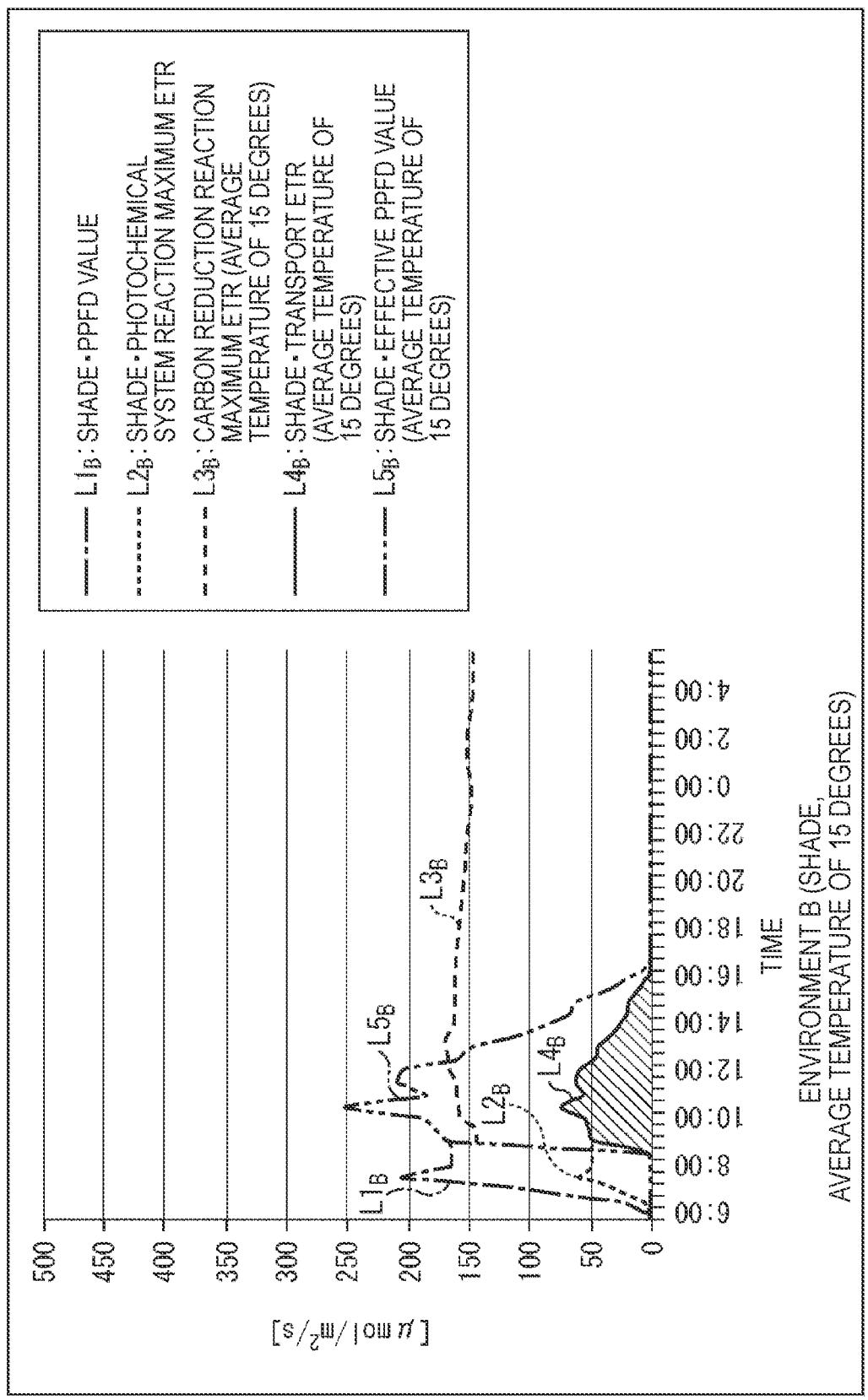
FIG. 23 is a diagram illustrating an example of display of PPFD values, effective PPFD values, and the like in an environment B.

FIG. 23 is a diagram illustrating an example of display of PPFD values, effective PPFD values, and the like in the environment B.

In the environment B, plants are present in the shade, an average temperature in the vicinity of the plants for a day is 15 degrees. As a result of simulation performed under such an environment, a line $L1_B$ indicates changes in a PPFD value (shade-PPFD value) of sunlight emitted to a shade portion of the plants. A line $L2_B$ indicates changes in a photochemical system reaction maximum ETR (shade-photochemical system reaction maximum ETR) when sunlight emitted to a shade portion of the plants is converted into energy by a photochemical system reaction of the plants.

A line $L3_B$ indicates changes in a carbon reduction reaction maximum ETR (carbon reduction reaction maximum ETR (an average temperature of 15 degrees)) of the plants which is determined in accordance with an environment such as an average temperature of 15 degrees. A line $L4_B$ indicates changes in a transport ETR (shade-transport ETR (an average temperature of 15 degrees)) in the environment B. That is, here, the value of the shade-photochemical system reaction maximum ETR is smaller than the value of the carbon reduction reaction maximum ETR (an average temperature of 15 degrees), and thus the shade-photochemical system reaction maximum ETR is determined to be a bottleneck and is set to be a shade-transport ETR (an average temperature of 15 degrees). As a result, in FIG. 23, the line $L4_B$ overlaps a portion of the line $L2_B$.

In addition, the line $L4_B$, which is a shade-transport ETR (an average temperature of 15 degrees), indicates a value having actually contributed to the growth of the plants, and an area of a portion (a portion indicated by an oblique line of FIG. 23) on the inner side of the line $L4_B$ is proportional to the amount of growth of the plants. A line $L5_B$ indicates changes in an effective PPFD value (shade-effective PPFD value (an average temperature of 15 degrees)) in the environment B, and is obtained by converting the value of the shade-transport ETR (an average temperature of 15 degrees) indicated by the line $L4_B$ into the amount of emission of sunlight emitted to a shade portion of the plants.

(5-3) Example of Display of Environment C (Sunshine, Average Temperature of 3 Degrees)

Figure 24:
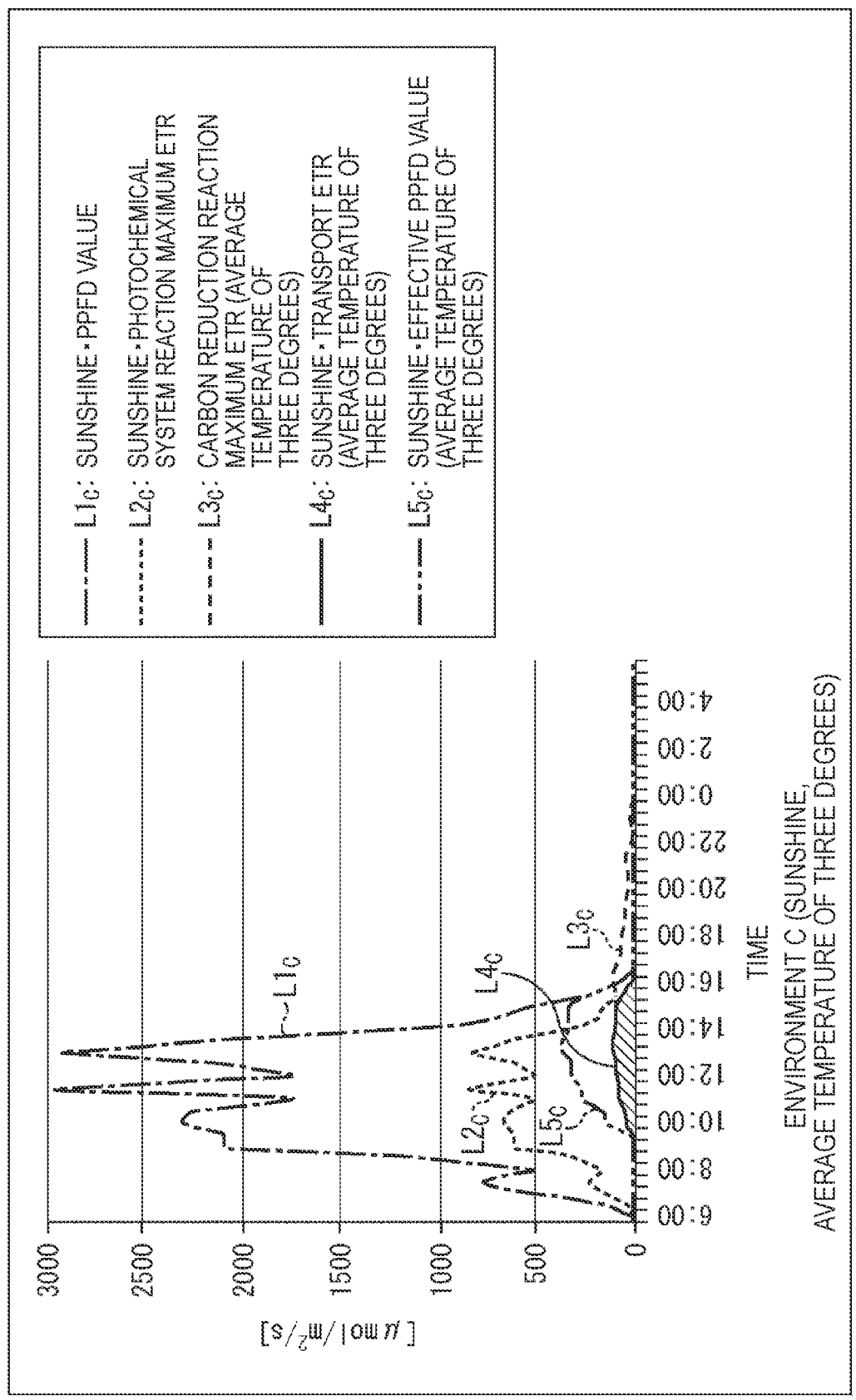
FIG. 24 is a diagram illustrating an example of display of PPFD values, effective PPFD values, and the like in an environment C.

FIG. 24 is a diagram illustrating an example of display of PPFD values, effective PPFD values, and the like in the environment C.

In the environment C, plants are present in the sunshine, and an average temperature in the vicinity of the plants for a day is 3 degrees. As a result of simulation performed under such an environment, a line $L1_C$ indicates changes in a PPFD value (sunshine-PPFD value) of sunlight emitted to a sunshine portion of the plants. A line $L2_C$ indicates changes in a photochemical system reaction maximum ETR (sunshine-photochemical system reaction maximum ETR) when sunlight emitted to a sunshine portion of the plants is converted into energy by a photochemical system reaction of the plants.

A line $L3_C$ indicates changes in a carbon reduction reaction maximum ETR (carbon reduction reaction maximum ETR (an average temperature of 3 degrees)) of the plants which is determined in accordance with an environment such as an average temperature of 3 degrees. A line $L4_C$ indicates changes in a transport ETR (sunshine-transport ETR (an average temperature of 3 degrees)) in the environment C. That is, here, the value of the carbon reduction reaction maximum ETR (an average temperature of 3 degrees) is smaller than the value of the sunshine-photochemical system reaction maximum ETR, and thus the carbon reduction reaction maximum ETR (an average temperature of 3 degrees) is determined to be a bottleneck and is set to be a sunshine-transport ETR (an average temperature of 3 degrees). As a result, in FIG. 24, the line $L4_C$ overlaps a portion of the line $L3_C$.

In addition, the line $L4_C$, which is a sunshine-transport ETR (an average temperature of 3 degrees), indicates a value having actually contributed to the growth of the plants, and an area of a portion (a portion indicated by an oblique line of FIG. 24) on the inner side of the line $L4_C$ is proportional to the amount of growth of the plants. A line $L5_C$ indicates changes in an effective PPFD value (sunshine-effective PPFD value (an average temperature of 3 degrees)) in the environment C, and is obtained by converting the value of the sunshine-transport ETR (an average temperature of 3 degrees) indicated by the line $L4_C$ into the amount of emission of sunlight emitted to a sunshine portion of the plants.

(5-4) Example of Display of Environment D (Shade, Average Temperature of 3 Degrees)

Figure 25:
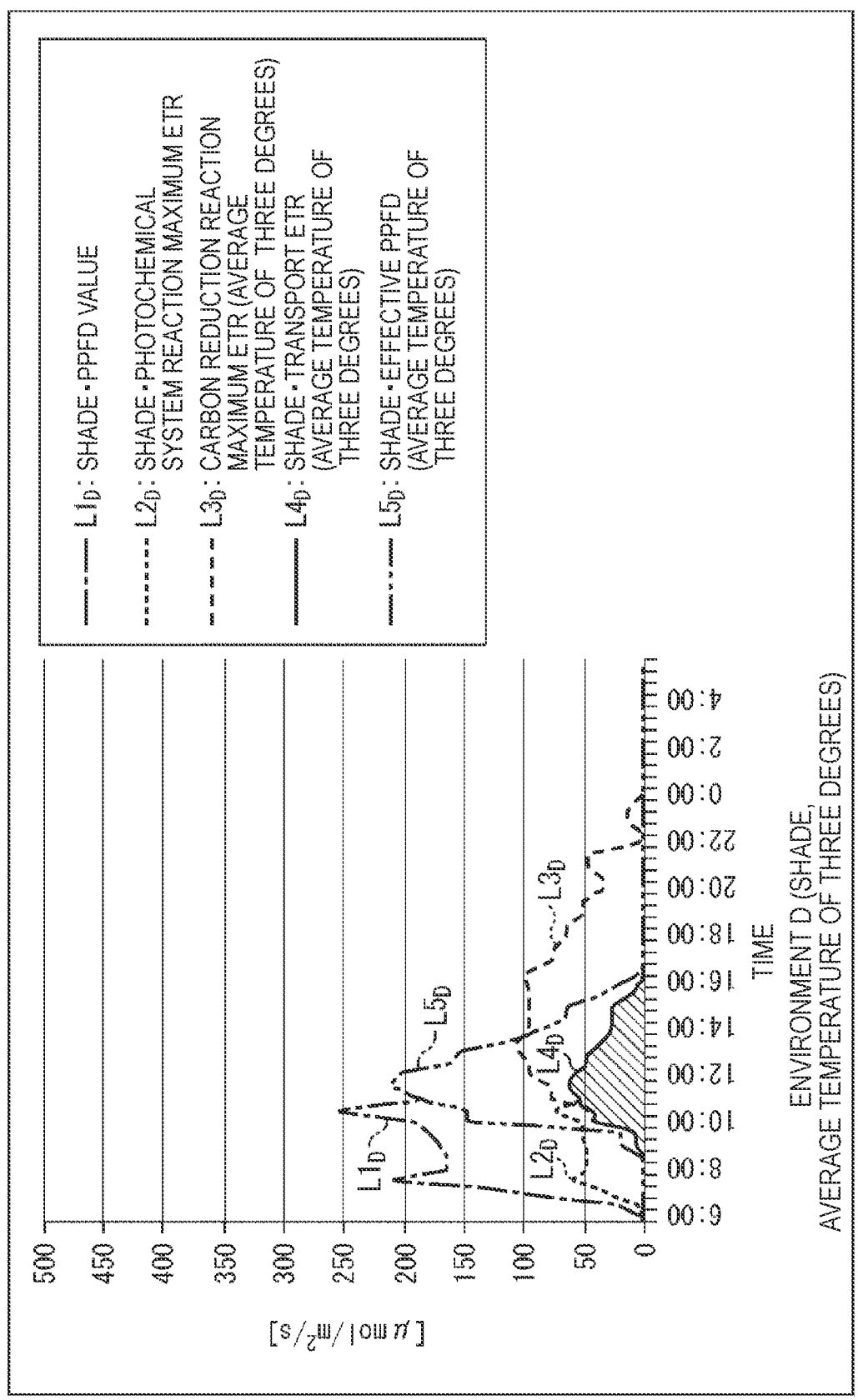
FIG. 25 is a diagram illustrating an example of display of PPFD values, effective PPFD values, and the like in an environment D.

FIG. 25 is a diagram illustrating an example of display of PPFD values, effective PPFD values, and the like in the environment D.

In the environment D, plants are present in the shade, an average temperature in the vicinity of the plants for a day is 3 degrees. As a result of simulation performed under such an environment, a line $L1_D$ indicates changes in a PPFD value (shade-PPFD value) of sunlight emitted to a shade portion of the plants. A line $L2_D$ indicates changes in a photochemical system reaction maximum ETR (shade-photochemical system reaction maximum ETR) when sunlight emitted to a shade portion of the plants is converted into energy by a photochemical system reaction of the plants.

A line $L3_D$ indicates changes in a carbon reduction reaction maximum ETR (carbon reduction reaction maximum ETR (an average temperature of 15 degrees)) of the plants which is determined in accordance with an environment such as an average temperature of 3 degrees. A line $L4_D$ indicates changes in a transport ETR (shade-transport ETR (an average temperature of 3 degrees)) in the environment D. That is, here, the value of the shade-photochemical system reaction maximum ETR is smaller than the value of the carbon reduction reaction maximum ETR (an average temperature of 3 degrees), and thus the shade-photochemical system reaction maximum ETR is determined to be a bottleneck and is set to be a shade-transport ETR (an average temperature of 3 degrees). As a result, in FIG. 25, the line $L4_D$ overlaps a portion of the line $L2_D$.

In addition, the line $L4_D$, which is a shade-transport ETR (an average temperature of 3 degrees), indicates a value having actually contributed to the growth of the plants, and an area of a portion (a portion indicated by an oblique line of FIG. 25) on the inner side of the line $L4_D$ is proportional to the amount of growth of the plants. A line $L5_D$ indicates changes in an effective PPFD value (shade-effective PPFD value (an average temperature of 3 degrees)) in the environment D, and is obtained by converting the value of the shade-transport ETR (an average temperature of 3 degrees) indicated by the line $L4_D$ into the amount of emission of sunlight emitted to a shade portion of the plants.

(Comparison Between Results of Simulations Performed in Environments a to D)

Here, comparison between results of simulations performed in the environments A to D illustrated in FIGS. 22 to 25 is as follows.

That is, since the PPFD value and the photochemical system reaction maximum ETR are determined according to sunlight emitted to plants, both the environment A of FIG. 22 and the environment C of FIG. 24 are sunshine, and thus the sunshine-PPFD values (the line $L1_A$, the line $L1_C$) and the sunshine-photochemical system reaction maximum ETRs (the line $L2_A$, the line $L2_C$) are consistent with each other.

On the other hand, since the carbon reduction reaction maximum ETR is affected by an atmospheric temperature, the average temperatures thereof are 15 degrees and 3 degrees in the environment A of FIG. 22 and the environment C of FIG. 24 which are different from each other, and thus the carbon reduction reaction maximum ETR (an average temperature of 15 degrees) indicated by the line $L3_A$ and the carbon reduction reaction maximum ETR (an average temperature of 3 degrees) indicated by the line $L3_C$ are different from each other.

Both the environment B of FIG. 23 and the environment D of FIG. 25 are shade, and thus the shade-PPFD values (the line $L1_B$, the line $L1_D$) and the shade-photochemical system reaction maximum ETRs (the line $L2_B$, the line $L2_D$) are consistent with each other. Note that although the unit of graduation of the vertical axis in each of the environment B of FIG. 23 and the environment D of FIG. 25 is different from that in each of the environment A of FIG. 22 and the environment C of FIG. 24, the PPFD value and the photochemical system reaction maximum ETR in the environment of shade become smaller than those in the environment of sunshine.

On the other hand, the average temperatures in the environment B of FIG. 23 and the environment D of FIG. 25 are 15 degrees and 3 degrees which are different from each other, and thus the carbon reduction reaction maximum ETR (an average temperature of 15 degrees) indicated by the line $L3_B$ and the carbon reduction reaction maximum ETR (an average temperature of 3 degrees) indicated by the line $L3_D$ are different from each other.

In addition, since both the average temperatures in the environment A of FIG. 22 and the environment B of FIG. 23 are 15 degrees, the environments differ in the unit of graduation of the vertical axis, but the carbon reduction reaction maximum ETR (an average temperature of 15 degrees) indicated by the line $L3_A$ and the carbon reduction reaction maximum ETR (an average temperature of 15 degrees) indicated by the line $L3_B$ are consistent with each other. Similarly, since both the average temperatures in the environment C of FIG. 24 and the environment D of FIG. 25 are 3 degrees, the environments differ in the unit of graduation of the vertical axis, but the carbon reduction reaction maximum ETR (an average temperature of 3 degrees) indicated by the line $L3_C$ and the carbon reduction reaction maximum ETR (an average temperature of 3 degrees) indicated by the line $L3_D$ are consistent with each other.

Here, comparison between the effective PPFD values indicated by the line $L5_A$, the line $L5_B$, the line $L5_C$, and the line $L5_D$ in the environment A of FIG. 22 to the environment D of FIG. 25 is as follows. That is, the value of the sunshine-effective PPFD value (an average temperature of 15 degrees) indicated by the line $L5_A$ in the environment A of FIG. 22 indicates the largest value exceeding 500 (umol/m$^2$/s). In contrast, the value of the shade-effective PPFD value (an average temperature of 3 degrees) indicated by the line $L5_D$ in the environment D of FIG. 25 is the smallest value.

(5-5) Example of Display of Integration of PPFD Values in Environments A to D

Figure 26:
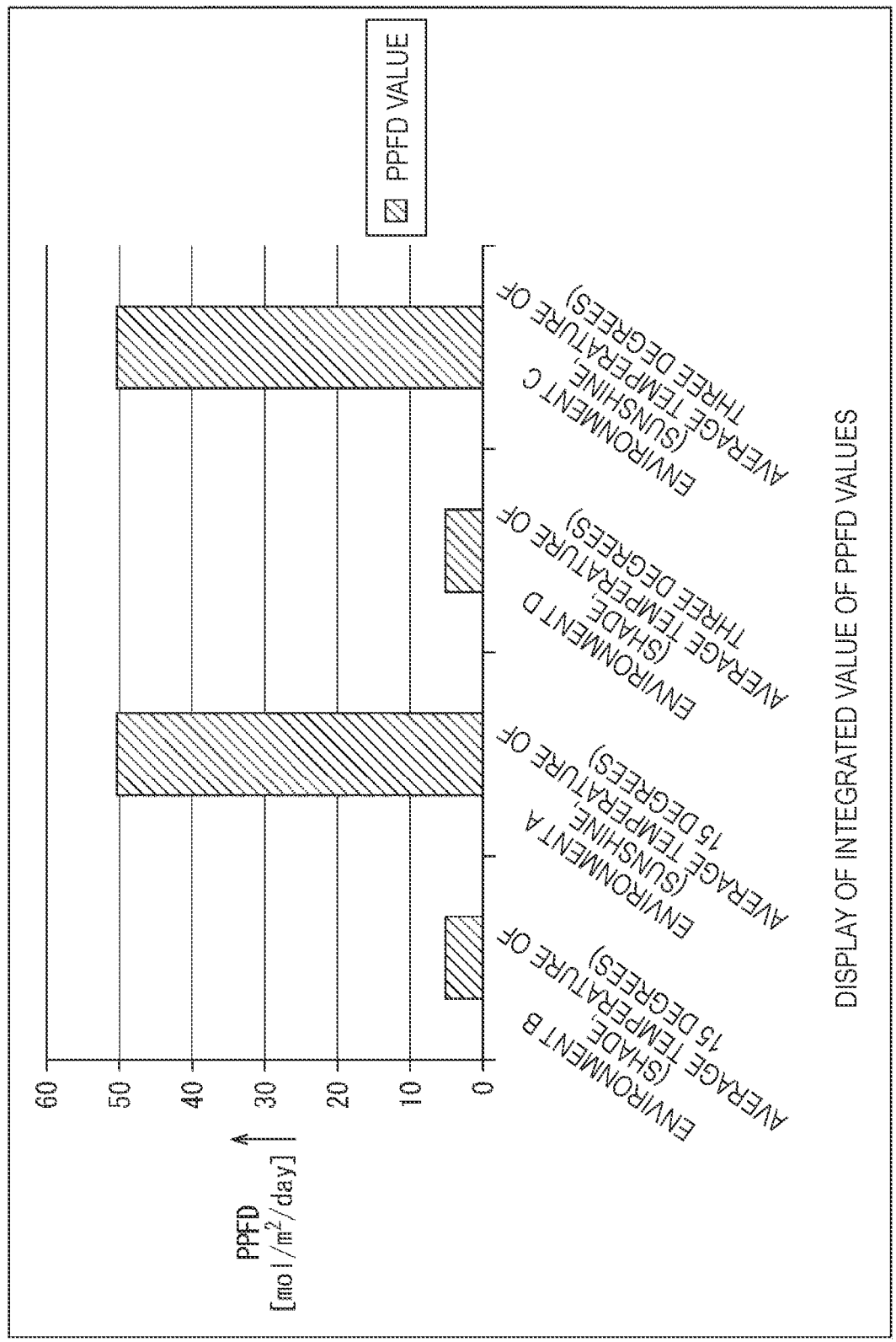
FIG. 26 is a diagram illustrating an example of display of integration of PPFD values in environments A to D.

FIG. 26 is a diagram illustrating an example of display of integration of PPFD values in the environments A to D.

In FIG. 26, an integrated value of PPFD values in each environment for a day is shown as a histogram for each of the environments A to D. Therefore, the unit of the vertical axis in FIG. 26 is mol/m$^2$/day.

As described above, the PPFD value is determined according to sunlight emitted to plants. For this reason, in FIG. 26, both the environment A and the environment C are sunshine, and thus the integrated values of the PPFD values for a day are consistent with each other. In addition, both the environment B and the environment D are shade, and thus the integrated values of the PPFD values for a day are consistent with each other.

Further, in FIG. 26, in the environments A and C and the environments B and D, the integrated value of the PPFD values for a day in the environment of sunshine is larger than that in the environment of shade.

Figure 27:
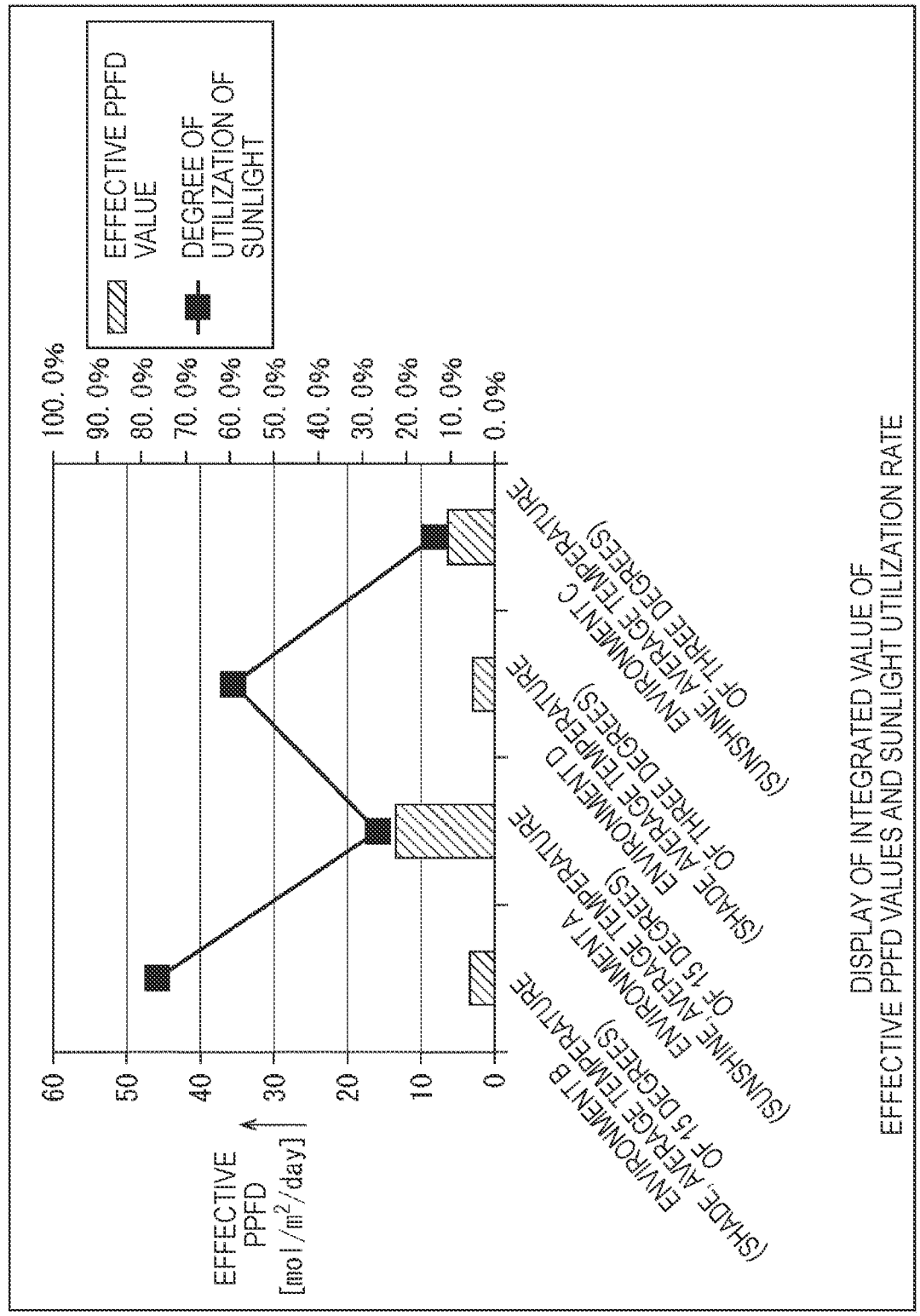
FIG. 27 is a diagram illustrating an example of display of integration of effective PPFD values in environments A to D and sunlight utilization rates.

(5-6) Example of Display of Integration of Effective PPFD Values in Environments A to D FIG. 27 is a diagram illustrating an example of display of integration of effective PPFD values in environments A to D and sunlight utilization rates.

In FIG. 27, an integrated value of effective PPFD values in each environment for a day is shown as a histogram for each of the environments A to D, and the unit of the vertical axis on the left side is mol/m$^2$/day. Further, in FIG. 27, the degree of utilization of sunlight in each environment is indicated by a line graph for each of the environments A to D, and the unit of the vertical axis is percent (%).

The effective PPFD value is a PPFD value obtained by converting the value of a transport ETR into the amount of emission of sunlight emitted to plants, and thus the amount of integration is also proportional to an amount having contributed to the amount of growth of the plants. In this regard, it can be seen that the degree of growth of the plants is highest in a case of the environment A.

Here, comparing the environment A and the environment C, which are both sunshine and have different average temperatures for a day, with each other, the integrated value of the effective PPFD values in the environment A is approximately 13 ($mol/m^2/day$), while the integrated value of the effective PPFD values in the environment C is approximately 7 ($mol/m^2/day$), and thus a difference between the integrated values is substantially double.

In addition, comparing the environment B and the environment D, which are both shade and have different average temperatures for a day, with each other, the integrated value of the effective PPFD values in the environment B is approximately 4 ($mol/m^2/day$), while the integrated value of the effective PPFD values in the environment D is approximately 3 ($mol/m^2/day$), and thus the integrated values are not greatly different from each other.

In this manner, by analyzing the effective PPFD values, it can be seen that there is a great difference in the growth of plants depending on an atmospheric temperature even in a case of the same amount of light emission and sunshine, while the amount of growth of plants is not greatly different depending on an atmospheric temperature in a case of the same amount of light emission and shade.

For example, only by analyzing the PPFD values illustrated in FIG. 26, it cannot be seen whether or not the integrated values of the PPFD values for a day are consistent with each other and there is a difference in the growth of plants depending on an atmospheric temperature in the environment A and the environment C. However, by analyzing the effective PPFD values illustrated in FIG. 27, it can be seen that a difference between the integrated values of the effective PPFD values is substantially double, and there is a difference in the growth of plants depending on an atmospheric temperature.

Further, in FIG. 27, the line graph indicates the degree of utilization (%) of sunlight obtained by dividing an effective PPFD value by a PPFD value for each of the environments A to D. From the line graph, an effective PPFD value becomes large in the environment A and the environment C which are both sunshine, but the degree of utilization of sunlight is lower than that of a PPFD value obtained from emitted sunlight. On the other hand, in the environment B and the environment D which are both shade, an effective PPFD value is small, but the degree of utilization of sunlight becomes large.

Here, plants in the sunshine consume most of extremely strong sunlight as heat or fluorescence, but it is said that an extremely large consumption also leads to a harmful effect such as light inhibition of plants. It is assumed that the state of the degree of utilization of sunlight is useful in a case in which a stress state of the plants is analyzed.

Figure 28:
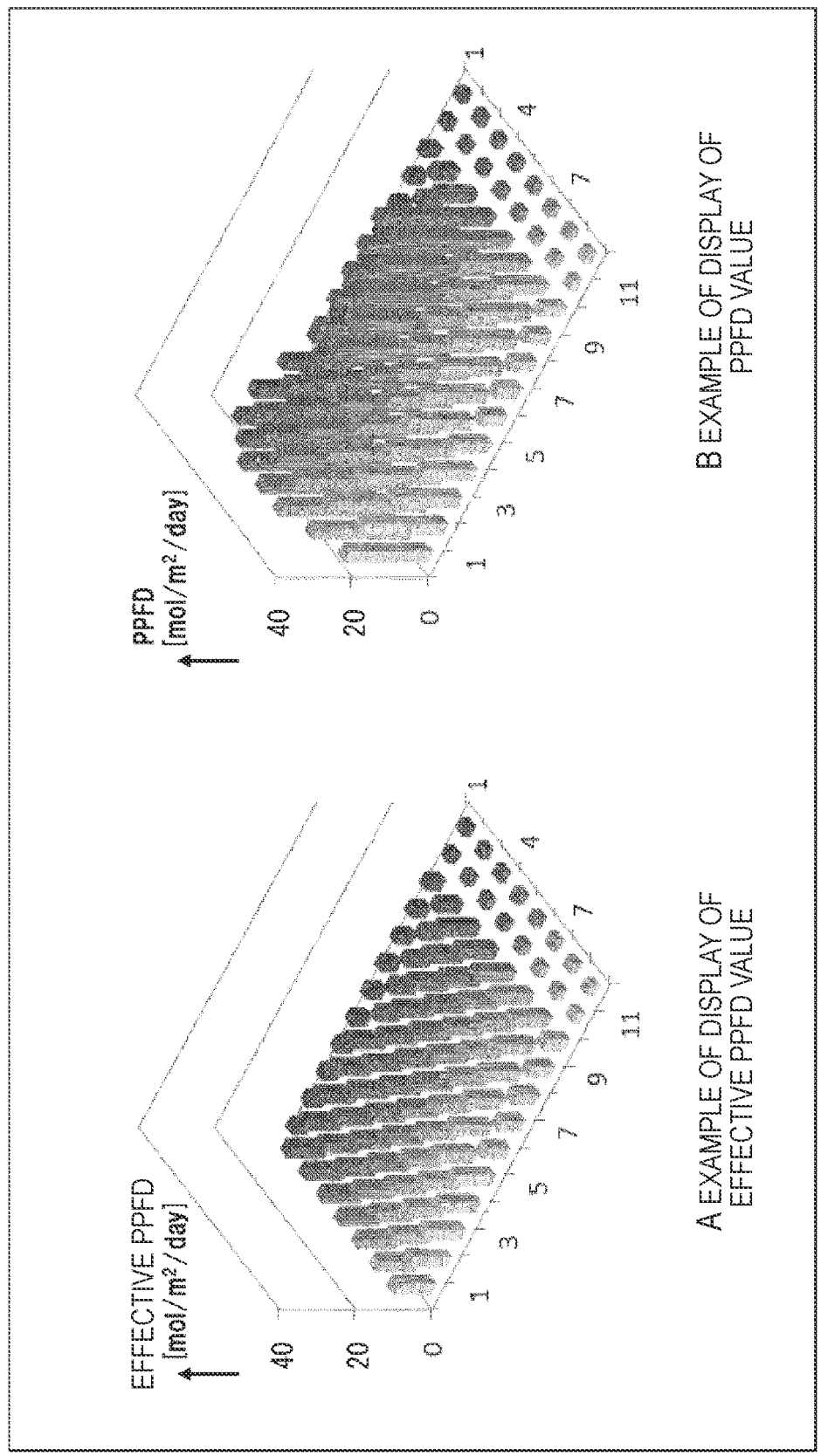
FIG. 28 is a diagram illustrating an example of display of effective PPFD values as two-dimensional information.

(5-7) Example of Display of Effective PPFD Values as Two-Dimensional Information FIG. 28 is a diagram illustrating an example of display of effective PPFD values as two-dimensional information.

FIG. 28 illustrates an example of a case in which effective PPFD values and PPFD values are displayed as two-dimensional information (two-dimensional image) on the basis of data obtained by sensing performed by the sensor 144 having a plurality of pixels two-dimensionally arranged in a repetitive pattern.

A of FIG. 28 illustrates, for example, an integrated value of effective PPFD values for a day for each region obtained by 12×8 division in a case in which a region (vegetation area) of plants in a field as the measurement target 1 is divided into 12 regions in the horizontal direction and divided into 8 regions in the vertical direction (each column (bar) of a graph of a histogram represents effective PPFD values in the regions per day). That is, in a three-dimensional graph illustrated in A of FIG. 28, each region obtained by 12×8 division is represented by an XY plane, and the magnitude of the effective PPFD value in each region is represented by the Z-axis direction (unit: $mol/m^2/day$). In this manner, the effective PPFD value is displayed as two-dimensional information (for example, information of an XY plane), so that it is possible to present a PPFD value effective for the plants even in a wide region such as a region of plants in a field.

In addition, B of FIG. 28 illustrates an integrated value of PPFD values for a day for each region obtained by performing 12×8 division on the region of plants in a field as the measurement target 1. That is, 12×8 regions of B of FIGS. 28 and 12×8 regions of A of FIG. 28 correspond to each other, and it is possible to switch between the two-dimensional information of the effective PPFD values of A of FIG. 28 and the two-dimensional information of the PPFD values of B of FIG. 28 in accordance with a user's operation or the like. Note that, the two-dimensional information of the effective PPFD values of A of FIG. 28 and the two-dimensional information of the PPFD values of B of FIG. 28 may be displayed at the same time. Thereby, the user can compare the effective PPFD values and the PPFD values with each other for each region of the plants in a field or throughout the region of the plants in a field.

That is, as described above, measured PPFD values are not necessarily actually effectively utilized for the plants. For this reason, in the present technology, effective PPFD values can be calculated as PPFD values effective for the plants. However, for example, it is possible to easily ascertain whether or not the amount of light necessary for the plants has been emitted by displaying an integrated value of the effective PPFD value and an integrated value of the PPFD values at the same time or in a switching manner.

Specifically, in the above description, as examples of FIG. 3 or FIG. 4, in a case in which plants are irradiated with 2000 $umol/m^2$ of light for three hours when light effective for the plants is 500 $umol/m^2$, and a case in which plants are irradiated with 500 $umol/m^2$ of light for six hours when light effective for the plants is 500 $umol/m^2$, it can be said that more effective sunshine is obtained in the latter case in which the amount of effective photons is increased. Also in such two cases, integrated values of effective PPFD values and integrated values of PPFD values are displayed in a display form as illustrated in FIG. 28, and thus it is possible to easily ascertain in which case more effective sunshine is obtained, and the like.

Note that the two-dimensional display of the effective PPFD values and the two-dimensional display of the PPFD values illustrated in FIG. 28 are examples of a display form for presenting two-dimensional information, and the two-dimensional information of the effective PPFD values and the two-dimensional information of the PPFD values may be displayed in other display forms.

For example, the two-dimensional information of the effective PPFD values (A of FIG. 28) and the two-dimensional information of the PPFD values (B of FIG. 28) may be displayed for each region so as to be superimposed on each other. Such superimposition display is presented, so that a user can intuitively recognize a difference between the effective PPFD value and the PPFD value for each region. In addition, at least one of the two-dimensional information of the effective PPFD values (A of FIG. 28) or the two-dimensional information of the PPFD values (B of FIG. 28) may be displayed so as to be superimposed on a captured image of, for example, plants in a field or the like. Such superimposition display is presented, so that the user can ascertain a relationship between the actual state of the plants and the effective PPFD value or the PPFD value.

In addition, for example, the two-dimensional information of the effective PPFD values or the PPFD values may be displayed in other display forms, such as the change of color or brightness, as long as the display forms make it possible to recognize each column (bar) of a graph, in addition to superimposition display of each column (bar) of a graph of a histogram as illustrated in FIG. 28. Further, for example, regarding the display of two-dimensional information of effective PPFD values or PPFD values, only a portion of which the value exceeds or falls below a predetermined reference value is displayed, or only the portion may be highlighted. In this case, as the reference value, for example, any input value, an average value of regions to be measured, or the like can be used.

In addition, here, a case in which an effective PPFD value and a PPFD value are presented as two-dimensional information has been described, but the value of a fraction of absorbed photosynthetically active radiation (fAPAR) may be similarly displayed two-dimensionally.

As described above, as presentation information, a PPFD value having actually contributed to the growth of plants can be presented (displayed) as an effective PPFD value, and thus it is possible to analyze the growth of the plants as the measurement target 1 from various angles. That is, it is known that photosynthesis of plants is affected by the number of photons which are particles of light rather than by light energy. However, the number of photons allowing plants to effectively utilize light is greatly affected by environmental conditions such as carbon dioxide ($CO_2$), temperature, humidity, and nutrients, and the types and states of the plants. Consequently, in the present technology, a PPFD value assumed to effectively utilize the plants is predicted from such environmental conditions and the types and states of the plants to calculate and display an effective PPFD value.

Note that the examples of display illustrated in FIGS. 22 to 28 are examples of a display form for presenting a statistical value of data such as a PPFD value and an effective PPFD value, and the statistical value of data such as a PPFD value and an effective PPFD value may be displayed in other display forms. In addition, such data is collected within a predetermined time range such as a daily unit, a weekly unit, or a monthly unit as illustrated in FIG. 28, and thus it is possible to accumulate, for example, data regarding sunshine which is important for the growth of plants. Thereby, it is possible to collect data such as a PPFD value and an effective PPFD value in common units of time such as a daily unit or a weekly unit, for example, for each plant as the measurement target 1.

4. Modification Example (Another Example of Reference Reflecting Plate)

In the above description, a reference reflecting plate, such as a gray reflecting plate, which has flat spectral reflection characteristics is used as the reference reflecting plate 20, but the reference reflecting plate is not limited to having a movable plate shape and may be a predetermined fixed region as long as a reflectance is known already. For example, in a case in which grass in a stadium is measured, an en-tout-cas can be used as a reference reflecting region. Further, for example, in a case in which a region, such as an en-tout-cas, which has flat spectral reflection characteristics is used as a reference reflecting region, the necessity of previously preparing a coefficient calculation LUT (LUT1) corresponding to the reference reflecting region has been described above.

Note that an en-tout-cas is formed in a region in the vicinity of a region of grass serving as a measurement target (region to be measured) in a stadium such as a soccer field, and can be used as a reference reflecting region (reference area) because reflection characteristics are substantially fixed and can be measured in advance.

Note that a reference reflecting plate having a predetermined reflectance may be created and used as the reference reflecting plate 20. Also in this case, the reference reflecting plate can be installed at any position, but a reference reflecting plate having a predetermined reflectance can be installed at a position where sensing can be performed at the same time as the measurement target 1, for example, as illustrated in FIG. 11. In addition, the reference reflecting plate 20 (reference reflecting region) can be sensed at a timing temporally different from the measurement target 1.

(Specific Example of Sensor)

In the above description, the sensor 144 (FIG. 7) is a sensor including a pixel array portion in which a plurality of pixels are two-dimensionally arranged, but the sensor may include various types of sensors such as a one-dimensional line sensor and an image sensor. Note that the image sensor includes an imaging element such as a Complementary Metal Oxide Semiconductor (CMOS) image sensor or a Charge Coupled Device (CCD) image sensor.

(Other Vegetation Indexes)

Further, in the above description, a normalized difference vegetation index (NDVI value) has been described as an example of an index (vegetation index) when plants are set to be the measurement target 1, but vegetation indexes other than the normalized difference vegetation index (NDVI value) may be measured. For example, as other vegetation indexes, a ratio vegetation index (RVI), a difference vegetation index (DVI), and the like can be used.

Here, the ratio vegetation index (RVI value) is calculated by arithmetically operating the following Expression (18).

$$RVI = IR/R \tag{18}$$

In addition, the difference vegetation index (DVI value) is calculated by arithmetically operating the following Expression (19).

$$DVI = IR - R \tag{19}$$

Here, in Expression (18) and Expression (19), IR represents a reflectance in an infrared region, and R represents a reflectance of red in a visible region. Note that, here, only a vegetation index using IR and R as parameters is illustrated, but it is of course possible to measure other vegetation indexes using reflectances of light in visible regions other than red, and the like as parameters. In addition, a spectrum ratio is not limited to a combination of R and IR. In a case in which components in other wavelength bands, such as G and B other than R and IR, are output as outputs of RGBIR from the sensor 144, the values thereof may be used.

(Other Configuration Examples During Measurement of Sensing Device)

In the above description, a case in which the sensing device 101 is mounted on the moving measurement device 70 (FIG. 11) performing movement observation or the fixed-point measurement device 80 (FIG. 11) performing fixed-point observation has been described, but any configuration can be adopted as long as the measurement target 1 and the reference reflecting plate 20 can be sensed by the sensing device 101.

For example, the sensing device 101 may be mounted on an artificial satellite. In the artificial satellite, index measurement data (for example, a measured value corresponding to a satellite image) obtained by sensing (imaging from the artificial satellite) which is performed by the sensing device 101 is transmitted to the effective index computation device 103 through a predetermined communication route. Further, in the effective index computation device 103, the calculation unit 171 can obtain an index (PPFD value) of the measurement target 1 (for example, plants in a field) which is measured from the artificial satellite on the basis of the index measurement data transmitted from the sensing device 101 mounted on the artificial satellite.

5. Configuration of Computer

Figure 29:
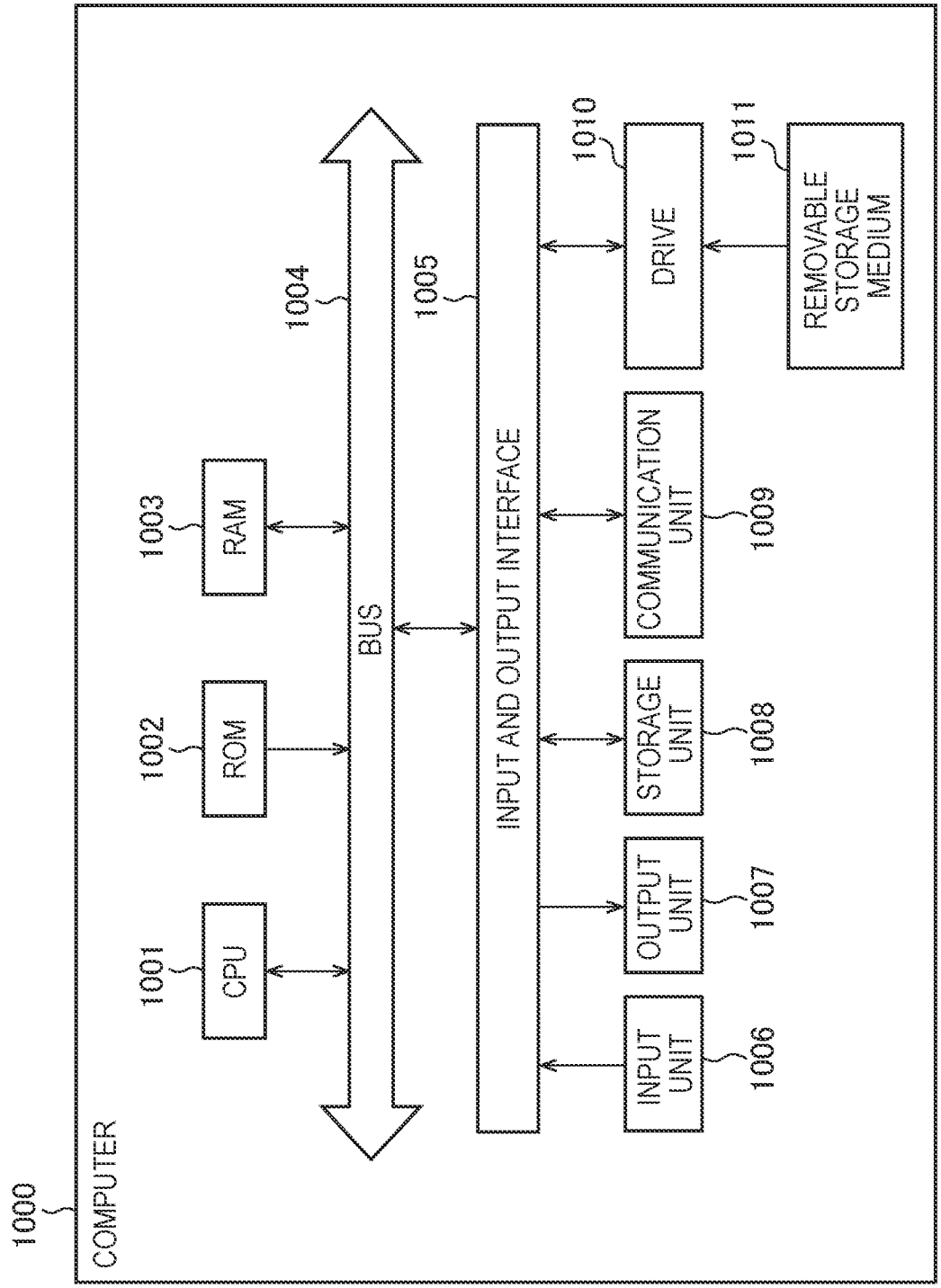
FIG. 29 is a diagram illustrating a configuration example of a computer.

The above-described series of processes (the processes of steps S102 to S106 in the effective PPFD calculation process of FIG. 10) may be executed by hardware or software. In a case in which the series of processes is executed by software, a program including the software is installed on a computer. FIG. 29 is a diagram illustrating an example of a hardware configuration of a computer in which the above-described series of processes is executed by the program.

In a computer 1000, a central processing unit (CPU) 1001, a read-only memory (ROM) 1002, and a random access memory (RAM) 1003 are connected to each other by a bus 1004. An input and output interface 1005 is further connected to the bus 1004. An input unit 1006, an output unit 1007, a recording unit 1008, a communication unit 1009, and a drive 1010 are connected to the input and output interface 1005.

A keyboard, a mouse, a microphone, or the like is used as the input unit 1006. A display, a speaker, or the like is used as the output unit 1007. A hard disk, a nonvolatile memory, or the like is used as the recording unit 1008. A network interface or the like is used as the communication unit 1009. The drive 1010 drives the storage medium 1011 such as a magnetic disk, an optical disc, a magneto-optical disc, or a semiconductor memory.

In the computer 1000 that has the above-described configuration, the CPU 1001 executes the above-described series of processes by loading a program recorded on the ROM 1002 or the recording unit 1008 to the RAM 1003 via the input and output interface 1005 and the bus 1004 and executing the program.

The program executed by the computer 1000 (the CPU 1001) can be recorded on, for example, the removable storage medium 1011 such as a package medium for supply. In addition, the program can be supplied via a wired or wireless transmission medium such as a local area network, the Internet, or digital broadcasting.

In the computer 1000, the program can be installed on the recording unit 1008 via the input and output interface 1005 by mounting the removable storage medium 1011 on the drive 1010. In addition, the program can be received by the communication unit 1009 via a wired or wireless transmission medium and can be installed on the recording unit 1008. Additionally, the program can be installed in advance on the ROM 1002 or the recording unit 1008.

Here, in the present specification, processes executed by the computer in accordance with the program may not necessarily be executed chronologically in the order described as a flowchart. That is, the processes executed by the computer in accordance with the program also include processes executed in parallel or individually (for example, parallel processes or processes by objects). In addition, the program may be processed by one computer (processor) or may be distributed and processed by a plurality of computers.

Moreover, embodiments of the present technology are not limited to the above-described embodiments, but various changes can be made within the scope of the present technology without departing from the gist of the present technology. For example, an embodiment in which all or some of the plurality of the above-mentioned embodiments are combined, may be adopted.

Additionally, the present technology may also be configured as below.

(1)

An information processing device including:

a calculation unit that calculates an effective index representing a degree of light effectively utilized for a measurement target in light incident on the measurement target, as an index regarding the light incident on the measurement target on the basis of a measured value regarding the measurement target obtained by sensing performed by a sensor.

(2)

The information processing device according to (1), in which the measurement target is a plant, and the effective index is an index obtained by converting a transport Electron Transport Rate (ETR) of the plant into an amount of emission of light incident on the plant.

(3)

The information processing device according to (2), in which the calculation unit calculates the transport ETR on the basis of a photochemical system reaction maximum ETR and a carbon reduction reaction maximum ETR.

(4)

The information processing device according to (3), in which the calculation unit compares the photochemical system reaction maximum ETR and the carbon reduction reaction maximum ETR with each other, and sets a smaller ETR to be the transport ETR.

(5)

The information processing device according to any of (1) to (4), in which the measurement target is a plant, the measured value is a value based on light reflected from the plant, and the calculation unit calculates a fraction of absorbed photosynthetically active radiation (fAPAR) on the basis of the value based on the light reflected from the plant.

(6)

The information processing device according to (5), in which the calculation unit calculates the effective index on the basis of the fraction of absorbed photosynthetically active radiation (fAPAR).

(7)
The information processing device according to (3),
in which the calculation unit calculates the photochemical system reaction maximum ETR on the basis of a measurement index, a fraction of absorbed photosynthetically active radiation (fAPAR), and a quantum yield (ΦPSII) of a photochemical system reaction regarding the light incident on the plant.

(8)
The information processing device according to (7),
in which the calculation unit calculates the measurement index on the basis of a measured value for the plant which is obtained by sensing performed by the sensor.

(9)
The information processing device according to any of (7) or (8),
in which the calculation unit calculates the quantum yield (ΦPSII) of the photochemical system reaction on the basis of any of a measurement time, a measurement location, and a type of the plant.

(10)
The information processing device according to (3),
in which the calculation unit calculates the carbon reduction reaction maximum ETR on the basis of environment information regarding a vicinity of the plant.

(11)
The information processing device according to (10),
in which the environment information regarding the vicinity of the plant includes a carbon dioxide concentration ($CO_2$ concentration), a temperature, and a humidity.

(12)
The information processing device according to (3), further including:
a control unit that controls presentation of presentation information corresponding to at least one of the measurement index regarding the light incident on the plant or the effective index.

(13)
The information processing device according to (12),
in which the presentation information is two-dimensional information.

(14)
The information processing device according to (13),
in which the control unit controls selective presentation of one of two-dimensional information of the measurement index and two-dimensional information of the effective index in accordance with a user's operation.

(15)
The information processing device according to (12),
in which the control unit controls presentation of at least one of the photochemical system reaction maximum ETR, the carbon reduction reaction maximum ETR, or the transport ETR.

(16)
The information processing device according to (12),
in which the control unit is, the measurement index and the effective index are calculated on the basis of a plurality of measured values measured at different times.

(17)
The information processing device according to (2),
in which a measurement index serving as the index regarding the light incident on the plant is an index indicating a degree at which the light incident on the plant acts on photosynthesis.

(18)
The information processing device according to (17),
in which the measurement index is a photosynthetic photon flux density (PPFD), and
the effective index is an effective PPFD value representing a PPFD value contributing to growth of the plant among the PPFD values.

(19)
An information processing method for an information processing device, the information processing method including:
a step of causing the information processing device to calculate an effective index representing a degree of light effectively utilized for a measurement target in light incident on the measurement target, as an index regarding the light incident on the measurement target on the basis of a measured value regarding the measurement target obtained by sensing performed by a sensor.

(20)
A program causing a computer to function as
an information processing device including a calculation unit that calculates an effective index representing a degree of light effectively utilized for a measurement target in light incident on the measurement target, as an index regarding the light incident on the measurement target on the basis of a measured value regarding the measurement target obtained by sensing performed by a sensor.

REFERENCE SIGNS LIST 10, 11 effective index computation system
20 reference reflecting plate
101, 101-1, 101-2 sensing device
102 environment sensor
103 effective index computation device
105 client device
108 network
109 server
110 storage
121 measurement unit
122 processing unit
141, 141-1, 141-2 lens
142, 142-1, 142-2 exposing unit
143 filter
143-1 RGB filter
143-2 IR filter
144, 144-1, 144-2 sensor
145, 145-1, 145-2 signal processing unit
146 I/F unit
161 I/F unit
162 processing unit
163 storage unit
164 presentation unit
171 calculation unit
172 control unit
221-1 B/R value calculation unit
221-2 B/G value calculation unit
221-3 G/R value calculation unit
222-1 W1 determination unit
222-2 W2 determination unit
222-3 W3 determination unit
223-1 multiplier
223-2 multiplier
223-3 multiplier
1000 computer
1001 CPU

The invention claimed is:

1. An information processing device comprising:
a memory storing program code; and
a processor configured to execute the program code to perform operations comprising:
calculating an effective index representing a degree of light effectively utilized for a measurement target in light incident on the measurement target, as an index regarding the light incident on the measurement target on a basis of a measured value of the measurement target obtained by sensing performed by a sensor, wherein the measurement target is a plant; and
calculating a transport ETR on a basis of a photochemical system reaction maximum ETR and a carbon reduction reaction maximum ETR, wherein the effective index is an index obtained by converting the transport Electron Transport Rate (ETR) of the plant into an amount of emission of light incident on the plant.

2. The information processing device according to claim 1,
wherein the calculation unit compares the photochemical system reaction maximum ETR and the carbon reduction reaction maximum ETR with each other, and sets a smaller ETR to be the transport ETR.

3. The information processing device according to claim 1,
wherein
the measured value is a value based on light reflected from the plant, and the operations further comprise
calculating a fraction of absorbed photosynthetically active radiation (fAPAR) on a basis of the value based on the light reflected from the plant.

4. The information processing device according to claim 3, wherein the operations further comprise calculating the effective index on a basis of the fraction of absorbed photosynthetically active radiation (fAPAR).

5. The information processing device according to claim 1,
wherein the operations further comprise calculating the photochemical system reaction maximum ETR on a basis of a measurement index, a fraction of absorbed photosynthetically active radiation (fAPAR), and a quantum yield (·PHI·PSII) of a photochemical system reaction regarding the light incident on the plant.

6. The information processing device according to claim 5,
wherein the operations further comprise calculating the measurement index on a basis of a measured value for the plant which is obtained by sensing performed by the sensor.

7. The information processing device according to claim 5,
wherein the operations further comprise calculating the quantum yield (·PHI·PSII) of the photochemical system reaction on a basis of any of a measurement time, a measurement location, and a type of the plant.

8. The information processing device according to claim 1,
wherein the operations further comprise calculating the carbon reduction reaction maximum ETR on a basis of environment information regarding a vicinity of the plant.

9. The information processing device according to claim 8,
wherein the environment information regarding the vicinity of the plant includes a carbon dioxide concentration ($CO_2$ concentration), a temperature, and a humidity.

10. The information processing device according to claim 1,
wherein the operations further comprise controlling presentation of presentation information corresponding to at least one of a measurement index regarding the light incident on the plant or the effective index.

11. The information processing device according to claim 10,
wherein the presentation information is two-dimensional information.

12. The information processing device according to claim 11,
wherein the operations further comprise controlling selective presentation of one of two-dimensional information of the measurement index and two-dimensional information of the effective index in accordance with a user's operation.

13. The information processing device according to claim 10,
wherein the operations further comprise controlling presentation of at least one of the photochemical system reaction maximum ETR, the carbon reduction reaction maximum ETR, or the transport ETR.

14. The information processing device according to claim 10,
wherein the measurement index and the effective index are calculated on a basis of a plurality of measured values measured at different times.

15. The information processing device according to claim 1,
wherein a measurement index serving as the index regarding the light incident on the plant is an index indicating a degree at which the light incident on the plant acts on photosynthesis.

16. The information processing device according to claim 15,
wherein the measurement index is a photosynthetic photon flux density (PPFD), and
the effective index is an effective PPFD value representing a PPFD value contributing to growth of the plant among the PPFD values.

17. An information processing method for an information processing device, the information processing method comprising:
calculating an effective index representing a degree of light effectively utilized for a measurement target in light incident on the measurement target, as an index regarding the light incident on the measurement target on a basis of a measured value of the measurement target obtained by sensing performed by a sensor, wherein the measurement target is a plant; and
calculating a transport ETR on a basis of a photochemical system reaction maximum ETR and a carbon reduction reaction maximum ETR, wherein the effective index is an index obtained by converting the transport Electron Transport Rate (ETR) of the plant into an amount of emission of light incident on the plant.

18. A non-transitory computer-readable medium storing a program, the program being executable by a computer to perform operations comprising:
- calculating an effective index representing a degree of light effectively utilized for a measurement target in light incident on the measurement target, as an index regarding the light incident on the measurement target on a basis of a measured value of the measurement target obtained by sensing performed by a sensor, wherein the measurement target is a plant; and
- calculating a transport ETR on a basis of a photochemical system reaction maximum ETR and a carbon reduction reaction maximum ETR, wherein the effective index is an index obtained by converting the transport Electron Transport Rate (ETR) of the plant into an amount of emission of light incident on the plant.

* * * * *